US010471231B2

(12) United States Patent
Moore-Ede et al.

(10) Patent No.: US 10,471,231 B2
(45) Date of Patent: Nov. 12, 2019

(54) SYSTEMS AND METHODS FOR CONTROLLING ENVIRONMENTAL ILLUMINATION

(71) Applicant: Circadian Zirclight Inc., Stoneham, MA (US)

(72) Inventors: Martin Moore-Ede, Wellesley, MA (US); Doros Platika, Charleston, MA (US); Irene Fassler, Lexington, MA (US); Ken Appleman, Troy, NY (US); Harish Rao, Lexington, MA (US); Anneke Heitmann, Arlington, MA (US); Udo Trutschel, Tabarz (DE); Mark Smith, Fort Collins, CO (US); John Luciani, Wakefield, MA (US)

(73) Assignee: CIRCADIAN ZIRCLIGHT INC., Stoneham, MA (US)

( * ) Notice: Subject to any disclaimer, the term of this patent is extended or adjusted under 35 U.S.C. 154(b) by 0 days.

(21) Appl. No.: 15/556,793

(22) PCT Filed: Mar. 9, 2016

(86) PCT No.: PCT/US2016/021530
§ 371 (c)(1),
(2) Date: Sep. 8, 2017

(87) PCT Pub. No.: WO2016/145059
PCT Pub. Date: Sep. 15, 2016

(65) Prior Publication Data
US 2018/0043130 A1 Feb. 15, 2018

Related U.S. Application Data

(60) Provisional application No. 62/130,406, filed on Mar. 9, 2015, provisional application No. 62/130,382, filed
(Continued)

(51) Int. Cl.
A61M 21/00 (2006.01)
A61M 21/02 (2006.01)
(Continued)

(52) U.S. Cl.
CPC ........ A61M 21/02 (2013.01); A61M 21/0094 (2013.01); A61N 5/0618 (2013.01);
(Continued)

(58) Field of Classification Search
CPC ... A61M 21/00; A61M 21/02; A61M 21/0094
(Continued)

(56) References Cited

U.S. PATENT DOCUMENTS

2009/0174658 A1 7/2009 Blatchley et al.
2012/0001555 A1 1/2012 Tu et al.

FOREIGN PATENT DOCUMENTS

WO WO 2013/184627 12/2013
WO WO 2013/186665 12/2013
WO WO 2014/165692 10/2014

OTHER PUBLICATIONS

Supplementary European Search Report Issued in Corresponding European Application No. EP16762412, dated Sep. 21, 2018.
(Continued)

Primary Examiner — John P Lacyk
(74) Attorney, Agent, or Firm — Norton Rose Fulbright US LLP

(57) ABSTRACT

Systems and methods for controlling environmental illumination relative to circadian function of individuals are provided. A method is provided for controlling the operation of light sources by assigning a circadian state to the individual based on received electronic information, extrapolating future circadian states based on the assigned circadian state, the assigned circadian state or the extrapolated future circadian states including at least a biological night state, and
(Continued)

encoding machine-level control commands that control the operation of the light source for transmission to the light sources adapted for the biological night state by having circadian-significant attenuation along the circadian active wavelength range.

14 Claims, 19 Drawing Sheets

Related U.S. Application Data on Mar. 9, 2015, provisional application No. 62/130, 402, filed on Mar. 9, 2015.

(51) Int. Cl.
*H05B 37/02* (2006.01)
*A61N 5/06* (2006.01)
*G16H 20/30* (2018.01)

(52) U.S. Cl.
CPC ......... *G16H 20/30* (2018.01); *H05B 37/0218* (2013.01); *H05B 37/0227* (2013.01); *H05B 37/0272* (2013.01); *H05B 37/0281* (2013.01); *A61M 2021/0044* (2013.01); *A61M 2205/3306* (2013.01); *A61M 2205/3368* (2013.01); *A61M 2205/3569* (2013.01); *A61M 2205/3592* (2013.01); *A61M 2205/50* (2013.01); *A61M 2205/584* (2013.01); *A61N 2005/0626* (2013.01); *A61N 2005/0636* (2013.01); *A61N 2005/0638* (2013.01); *A61N 2005/0663* (2013.01); *Y02B 20/42* (2013.01); *Y02B 20/46* (2013.01)

(58) Field of Classification Search
USPC ...................................................... 600/26–28
See application file for complete search history.

(56) References Cited

OTHER PUBLICATIONS

International Search Report issued in Application No. PCT/US2016/021530, dated May 17, 2016.
International Preliminary Report on Patentability issued in Application No. PCT/US2016/021530, dated Sep. 12, 2017.

| Label | 400-429nm [%] | 430-480 nm [%] | 481-700nm [%] | CS [%] | x (CIE 1931) | y (CIE 1931) | CCT [K] |
|---|---|---|---|---|---|---|---|
| Circadian Day | 0.28 | 4.78 | 94.94 | 9.9 | 0.5 | 0.415 | 2300 |
| Circadian Night | 24.11 | 0.27 | 75.62 | 10 | 0.5 | 0.415 | 2300 |
| Circadian Day | 0.35 | 6.24 | 93.41 | 12 | 0.485 | 0.415 | 2500 |
| Circadian Night | 28.48 | 0.33 | 71.19 | 11 | 0.485 | 0.415 | 2500 |
| Circadian Day | 0.7 | 12.2 | 87.1 | 19 | 0.443 | 0.406 | 3000 |
| Circadian Night | 37.3 | 0.96 | 61.74 | 14 | 0.443 | 0.402 | 3000 |
| Circadian Day | 0.62 | 16.45 | 82.93 | 25 | 0.405 | 0.399 | 3500 |
| Circadian Night | 42.34 | 1.79 | 55.87 | 17 | 0.405 | 0.39 | 3500 |
| Circadian Day | 1.04 | 18.97 | 79.99 | 29 | 0.381 | 0.38 | 4000 |
| Circadian Night | 46.93 | 2.05 | 51.02 | 18 | 0.381 | 0.38 | 4000 |
| Circadian Day | 1.2 | 21.5 | 77.3 | 33 | 0.36 | 0.368 | 4500 |
| Circadian Night | 50.72 | 2.32 | 46.96 | 19 | 0.36 | 0.37 | 4500 |
| Circadian Day | 1.15 | 24.11 | 74.74 | 36 | 0.346 | 0.355 | 5000 |
| Circadian Night | 54.38 | 2.43 | 43.19 | 19 | 0.346 | 0.355 | 5000 |
| Circadian Day | 1.25 | 26.34 | 72.41 | 38 | 0.34 | 0.34 | 5500 |
| Circadian Night | 57.1 | 2.43 | 40.47 | 19 | 0.34 | 0.34 | 5500 |
| Circadian Day | 1.58 | 28.07 | 70.35 | 40 | 0.33 | 0.33 | 6000 |
| Circadian Night | 55.56 | 3.4 | 41.04 | 20 | 0.33 | 0.33 | 6000 |

FIG. 12

SYSTEMS AND METHODS FOR CONTROLLING ENVIRONMENTAL ILLUMINATION

CROSS REFERENCE

This application is a national phase application under 35 U.S.C.§ 371 of International Application No. PCT/US 2016/021530 filed Mar. 9, 2016, which claims all benefits, including priority, of U.S. Provisional Patent Application Nos. 62/130,382, 62/130,402, and 62/130,406 filed on Mar. 9, 2015. The entire contents of each of the above-referenced disclosure disclosures are specifically incorporated herein by reference without disclaimer.

FIELD

Some embodiments relate generally to the field of lighting, and more particularly to the control of lighting adapted to maintain or otherwise affect the circadian rhythms of one or more individuals.

INTRODUCTION

Lighting may involve the use of light to illuminate various objects and environments so that individuals are able to visually perceive their surroundings. Light may be in various wavelengths and intensities, and have various characteristics, such as color, spread, polarization, correlated color temperature (CCT), color rendering index (CRI), etc.

Light sources may include both natural lighting (e.g., sunlight) and artificial light sources (e.g., light fixtures, emergency lighting, floodlights). Artificial light may be provided by various technologies, such as light-emitting diodes (LEDs), incandescent lights, tungsten lights, etc.

Artificial light sources are often used to illuminate areas and/or objects where natural light is not readily available. For example, artificial light sources may be used in workplaces, schools, homes, devices, stores, entertainment venues, etc.

Conventional lighting sources provide lighting in various environments; however, conventional lighting sources may have some deficiencies related to potential impacts on the natural circadian cycles of individuals exposed to the light provided by these sources.

For example, the use of conventional lighting sources may interrupt the natural circadian cycle of an individual.

Interruption of the circadian cycle and can be associated with both short and long term health effects.

A new, improved, and/or alternate solution may be desirable.

SUMMARY

In an aspect, there is provided a system for operating one or more light sources providing illumination to an individual, the system including: a data receiver unit configured to receive electronic information indicative of a circadian state of an individual from one or more data sources; a circadian state association unit configured to assign a circadian state to the individual based on the received electronic information, configured to extrapolate future circadian states based on the assigned circadian state, and configured to update a profile corresponding to the individual with the assigned circadian state and the extrapolated future circadian states, the assigned circadian state or the extrapolated future circadian states including at least a biological night state; a lighting command encoding unit receiving the profile corresponding to the individual and encoding machine-level control commands that control the operation of the one or more light sources; and a lighting command unit configured to transmit the machine-level control commands to the one or more light sources, the machine-level control commands adapted such that the aggregate incident lighting provided by the one or more light sources provides light with a spectral power distribution having circadian-significant attenuation along a circadian active wavelength range during durations of time when the individual is in the biological night state, and the aggregate incident lighting provided by the one or more light sources has overall lighting characteristics within a pre-determined comparable range relative to the aggregate incident lighting provided by the one or more light sources when the one or more light sources are activated but not controlled to have circadian-significant attenuation along the circadian active wavelength range.

In an aspect, the electronic information is set by default to be time of day information where information is not received from the one or more data sources.

In an aspect, the one or more light sources include at least one of LED light sources, lasers, and quantum dots.

In an aspect, light emitted in the circadian active wavelength range affects melatonin secretion in the individual.

In an aspect, the one or more light sources emit white or substantially near white light.

In an aspect, the overall lighting characteristics include at least (i) a spectral power distribution in human-visible wavelengths, (ii) a correlated color temperature, and (iii) a color rendering index score, (iv) a Planckian curve offset, and (v) a Duv.

In an aspect, the circadian active wavelength range includes wavelengths of blue light.

In an aspect, the circadian active wavelength range includes wavelengths of blue light provided between about 430 nm to about 490 nm.

In an aspect, the circadian active wavelength range includes wavelengths of blue light selected from a group consisting of wavelength band ranges of: about 430 nm to about 500 nm, about 430 nm to about 490 nm, about 430 nm to about 480 nm, about 430 nm to about 470 nm, about 435 nm to about 500 nm, about 435 nm to about 490 nm, about 435 nm to about 480 nm, about 435 nm to about 470 nm, about 440 nm to about 500 nm, about 440 nm to about 490 nm, about 440 nm to about 480 nm, about 440 nm to about 470 nm, about 450 nm to about 500 nm, about 450 nm to about 490 nm, and about 460 nm to about 500 nm.

In an aspect, the aggregate incident lighting provided in the circadian active wavelength range is attenuated to a percentage of an overall spectral power in a visible light wavelength range, selected from the group of percentages consisting of equal to or less than 10%, equal to or less than 5%, equal to or less than 3%, equal to or less than 1%, equal to or less than 0.5% and equal to or less than 0.1%.

In an aspect, the circadian active wavelength range includes wavelengths of blue light and green light.

In an aspect, the circadian active wavelength range includes wavelengths of blue light provided between about 430 nm to about 490 nm and wavelengths of green light provided between about 490 nm to about 550 nm.

In an aspect, the circadian active wavelength range includes wavelengths of green light selected from a group consisting of wavelength band ranges of: about 470 nm to about 560 nm, about 480 nm to about 550 nm, about 490 nm to about 555 nm, about 490 nm to about 560 nm, about 490 nm to about 565 nm, and about 490 nm to about 570 nm.

In an aspect, the aggregate incident lighting provided in the about 490 nm to about 550 nm wavelength range is attenuated to one percentage of an overall spectral power in a visible light wavelength range, selected from the group of percentages consisting of equal to or less than 10%, equal to or less than 5%, equal to or less than 3%, equal to or less than 1%, equal to or less than 0.5% and equal to or less than 0.1%.

In an aspect, the biological night state further includes (i) a biological early night state, and (ii) a biological late night state.

In an aspect, the biological early night state begins about 3 hours before an expected night sleep onset of the individual.

In an aspect, the biological early night state ends about 3 hours after an expected night sleep onset of the individual.

In an aspect, the biological late night state begins after the biological early night state and ends before a biological day state.

In an aspect, for the biological early night state, the lighting command encoding unit encodes machine-level control commands such that the aggregate incident lighting provided by the one or more light sources provides light with a spectral power distribution having circadian-significant attenuation along both the blue and green wavelength ranges during durations of time when the individual is in the at least one biological early night state; and for the biological late night state the lighting command encoding unit encodes machine-level control commands such that the aggregate incident lighting provided by the one or more light sources provides light with a spectral power distribution having circadian-significant attenuation only along the blue wavelength range during durations of time when the individual is in the at least one biological late night state, while providing substantial transmission along the green wavelength range.

In an aspect, the one or more light sources include a plurality of light sources, the plurality of light sources each provide illumination to the individual, and the lighting command unit is configured to track characteristics of the aggregate incident lighting provided by the plurality of light sources to the individual.

In an aspect, the data receiver unit is further configured to receive electronic information indicative of positions of at least one light source of the plurality of light sources.

In an aspect, the electronic information indicative of positions includes at least height information.

In an aspect, the lighting command encoding unit is configured to classify each light source of the plurality of light sources as being above an eye level of the individual or below the eye level of the individual, the eye level of the individual being a horizontal cross-section if the individual is upright or a vertical cross-section if the individual is in a supine or prone position.

In an aspect, the lighting command unit is configured to only transmit the machine-level control commands to the one or more light sources that are classified as being above the eye level of the individual.

In an aspect, the lighting command unit is configured to apply scored weighting to individual contributions of light by each light source of the plurality of light sources when tracking the characteristics of the aggregate incident lighting.

In an aspect, a first set of weights is applied to the one or more light sources that are classified as being above the eye level of the individual, and a second set of weights is applied to the one or more light sources that are classified as being below the eye level of the individual.

In an aspect, different weighting is applied to each light source of the plurality of light sources, the weighting differing based at least on height information associated with each light source.

In an aspect, varying weights are applied to each light source of the plurality of light sources, the weights varying based at least on one of: height information, position information, distance information, and intensity of light provided from each light source.

In an aspect, the one or more light sources provides illumination to a plurality of individuals.

In an aspect, the lighting command encoding unit is further configured to encode the machine-level control commands based on a plurality of current circadian states, each of the current circadian states corresponding to an individual of the plurality of individuals, and to periodically or continuously determine whether any individual of the plurality of individuals is in a biological night state; and the encoded machine-level control commands are configured to command the one or more light sources such that the aggregate incident lighting provided by the one or more light sources provides light with a spectral power distribution having circadian-significant attenuation along a circadian active wavelength range during durations of time when any individual of the plurality of individuals is in the biological night state.

In an aspect, the data receiver unit is further configured to receive electronic information indicative of positions of at least one light source of the plurality of light sources; the data receiver unit is further configured to receive information relating to an average height of the plurality of individuals; and the lighting command unit is configured to only transmit the machine-level control commands to the one or more light sources that are being above an average eye level determined based on the average height of the plurality of individuals.

In an aspect, the aggregate incident lighting is tracked based on a sensor worn by the individual; the data receiver unit is configured to receive electronic information from the sensor; and the lighting command encoding unit utilizes tracked sensor information in a feedback loop when encoding the machine-level control commands to control the one or more light sources.

In an aspect, the data receiver unit is configured to receive electronic information from a biochemical sensor monitoring one or more biological response cues from the individual indicative of a presence of circadian stimulation effects; and the lighting command encoding unit utilizes tracked sensor information in a feedback loop when encoding the machine-level control commands to control to the one or more light sources.

In an aspect, the combined incident light has at least one of a correlated color temperature between approximately 2600K and approximately 6500K, a color rendering index of at least approximately 70, an illumination level of approximately 100 lux to approximately 500 lux, and a chromaticity tolerance range within a fourteen step MacAdam ellipse between the one or more light sources when controlled for circadian-significant attenuation and the one or more light sources when not controlled for circadian-significant attenuation.

In an aspect, the circadian state association unit is configured to entrain circadian functioning of the individual by determining future circadian states based on one or more desired parameters of a circadian rhythm including at least one of amplitude, phase and periodicity rather than the current state circadian information.

In an aspect, at least one of the at least one light sources utilizes at least one of filters, LED chips, quantum dots, plasma, and phosphors to attenuate light.

In an aspect, the data receiver unit is configured to receive information from at least one of (i) one or more facility access databases, (ii) electronic calendar databases, (iii) tracked light exposure databases, (iv) location information databases, (v) work scheduling databases, (vi) indoor lighting schedules, (vi) outdoor lighting schedules, (vii) facial recognition platforms, (vii) travel record database, (viii) health records databases, (ix) fitness tracker databases and (x) outdoor light condition databases.

In an aspect, information from different data sources are weighted depending at least on data relevance scores, each data relevance score associated with each of the different data sources.

In an aspect, violet light emitting sources are provided for compensating for the attenuated circadian active wavelengths such that the aggregate incident lighting provided by the one or more light sources has overall lighting characteristics within a pre-determined comparable range relative to the aggregate incident lighting provided by the one or more light sources when the one or more light sources are not controlled to have circadian-significant attenuation along the circadian active wavelength range.

In an aspect, the violet light emitting sources emit light in a wavelength band selected from a group consisting of: between about 400 and about 440 nm, between about 400 and about 435 nm, between about 400 and about 430 nm, between about 400 and about 425 nm, and between about 400 and about 415 nm.

In an aspect, the violet light emitting sources emit light that, in respect of the aggregate incident lighting provided by the one or more light sources, provides an average irradiance greater than about four percent (4%), of the total irradiance from the light source in the visible light range.

In an aspect, the violet light emitting sources emit light that, in respect of the aggregate incident lighting provided by the one or more light sources, provides an average irradiance selected from one of a group of percentage ranges including 10-15%, 15-20%, and 20-25% of the total irradiance from the light source in the visible light range.

In an aspect, the one or more violet light emitting sources emit light in a first average irradiance during the biological night state and one or more blue light emitting sources emit light in a second average irradiance during states other than the biological night state.

In an aspect, the lighting command encoding unit further encodes machine-readable instructions to attenuate non-circadian active wavelengths such that a comparable average spectral power distribution in the visible wavelengths is maintained before and after attenuation of the circadian active wavelengths.

In an aspect, non-circadian active wavelengths that are also attenuated include at least selected wavelengths between 490 nm and 700 nm.

In an aspect, non-circadian active wavelengths that are also attenuated include at least selected wavelengths between 560 nm and 700 nm.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 12 is a chart providing sample values that may be used for the spectral power distribution of various lights, according to some embodiments.

DETAILED DESCRIPTION

Figure 1:
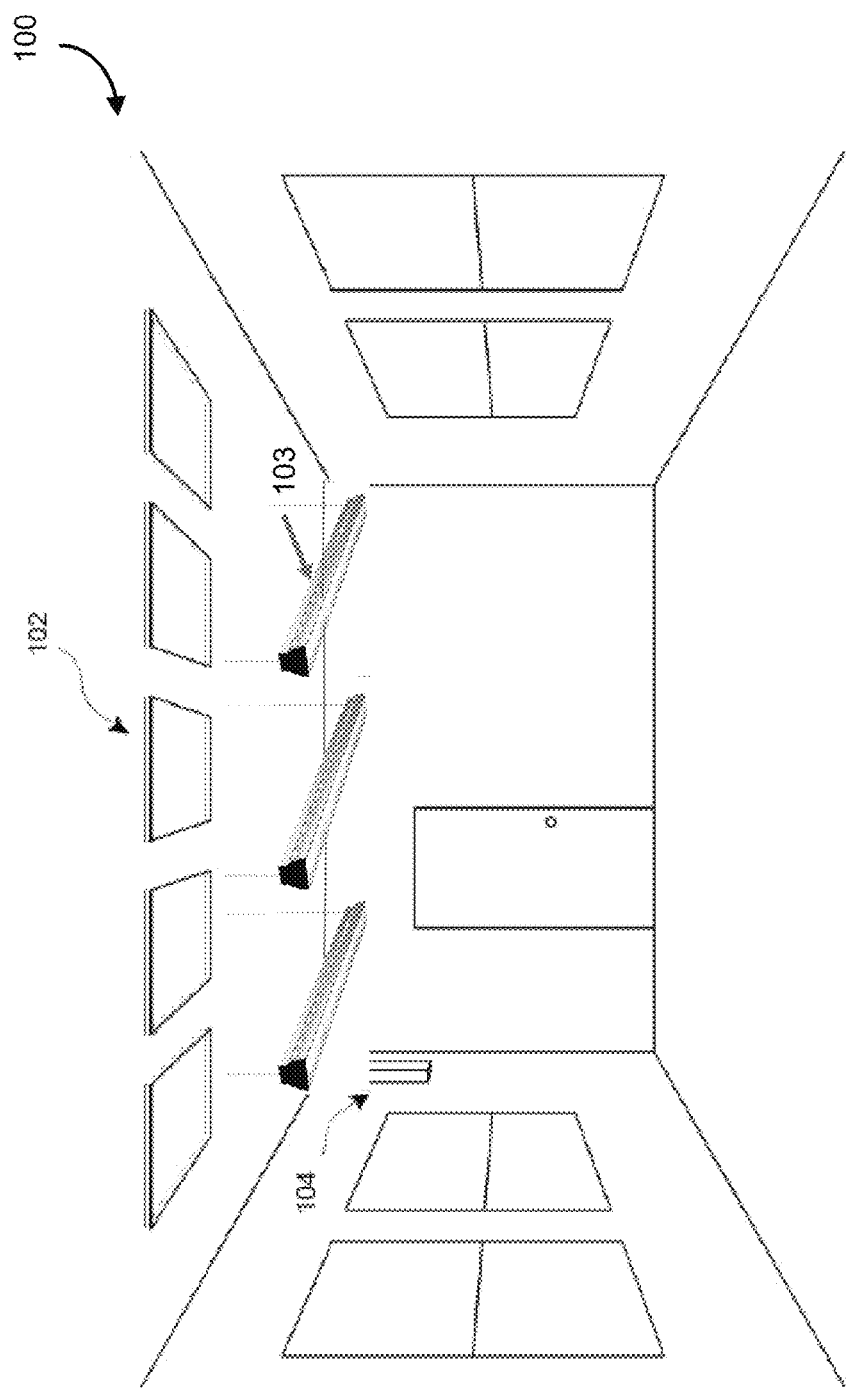
FIG. 1 illustrates one example of an indoor environment, having artificial lighting provided by ceiling troffer panels, pendant light fixtures and wall sconces, according to some embodiments.

Embodiments of methods, systems, and apparatus are described through reference to the drawings.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Lighting Effects on Circadian Processes

The maintenance of proper human circadian function has adapted over time as until the implementation of electric lighting, most people were exposed to bright natural light (e.g., 1,000-100,000 lux) during the daylight hours and to darkness or very dim light (e.g., 0 to 10 lux) during the night.

The regularly timed cycle of day and night resulting from the earth's rotation on its axis, and the seasonal modulation in day and night duration as the earth rotated around the sun, provided a predictably timed substantial contrast in light exposure intensity during day as compared to the night.

Human physiology, and the body systems that promote health and survival, were optimized over the course of evolution to operate most effectively under this high-contrast day-night light exposure cycle using an internal circadian timing system of biological clocks (circadian pacemakers) which oscillate with a near 24-hour periodicity and which are normally synchronized by the timing of light detected by a specialized set of photoreceptors in the eyes.

This circadian timing system enables the body to predict the onset of dawn and dusk and adjust physiological and behavioral systems to more effective states for the day or night ahead.

The circadian timing system is regulated by the master circadian clock located in the Suprachiasmatic Nuclei (SCN), a cluster of cells in the hypothalamus which receives transduced light-dark time cue signals via the retino-hypothamic tract from the retinal ganglion cells, and distributes timing signals via endocrine and neural pathways to the various systems of the body to ensure they are kept in synchronicity with day and night.

Circadian rhythms may be observed in various physiological functions including, but not limited to, sleep/wake cycle, feeding times, mood, alertness, cognitive function, cell proliferation and gene expression in various tissue types.

Various tissues and cell types contain independently oscillating cellular clocks, such as the liver, kidney and pancreas, among others, and are able to function autonomously through circadian expression of their "clock genes", although they are normally modulated and synchronized by the central SCN clock.

In the absence of environmental light cues, the SCN, and the circadian oscillators it synchronizes, will continue to generate a regularly timed circadian cycle but will drift in phase and become desynchronized from the external daynight cycle, and may become internally desynchronized from each other.

Among the key endocrine regulators used by the SCN to transmit transduced light-dark and circadian phase information to the systems of the body and initiate reparative and other protective functions at night are the neurohormone melatonin and the adrenal hormone cortisol.

Melatonin (N-acetyl-5-methoxytryptamine) is the principal hormone of the pineal gland, and mediates many biological functions, particularly the timing of those physiological functions that are controlled by the duration of light and darkness. Melatonin is synthesized from tryptophan through serotonin, which is N-acetylated by the enzyme n-acetyl transferase or NAT, and then methylated by hydroxyindol-O-methyl transferase.

The enzyme NAT is the rate-limiting enzyme for the synthesis of melatonin, and is increased by norepinephrine at the sympathetic nerve endings in the pineal gland. Norepinephrine is released at night or in the dark phase from these nerve endings. Thus, melatonin secretion may be strongly influenced by the daily pattern of light and dark exposure.

The release of high levels of melatonin during darkness at night is essential to healthy body functions. Melatonin has been shown to have various functions such as chronobiotic regulation, immunomodulation, antioxidant effects, regulation of the timing of seasonal breeding and oncostatic effects.

Evidence of oncostatic effects of melatonin that have been shown in vitro, and in animal studies, suggest a key role in suppressing tumors and protecting against the proliferation of cancer cells, including human breast and prostate cancer.

Low levels of nocturnal melatonin release may be associated with breast cancer, prostate cancer, type 2 diabetes, metabolic syndrome, insulin resistance, diabetic retinopathy, macular degeneration, hypertension, coronary artery disease, congestive heart failure, depression, anxiety, migraines and other life threatening or debilitating conditions.

In recent years, there has been an increasing recognition that melatonin may confer protection from disease, and lower levels of melatonin have been associated with a wide variety of diseases and chronic conditions. The scope of this relationship may be potentially far-reaching, and may include cancers, cardiovascular disorders such as hypertension and coronary artery disease, metabolic disorders such as insulin resistance and type II diabetes, Huntington's disease, multiple sclerosis, Alzheimer's disease, migraine headaches, and psychiatric disorders such as depression and anxiety, etc. In some diseases, such as cancer, there appears to be an inverse linear relationship between melatonin levels and disease risk, such that lower melatonin levels are associated with a significant increase in disease risk. Furthermore, there is no clear "threshold" for this relationship, suggesting that any loss of endogenous melatonin due to light exposure at night would be associated with relatively increased disease risk.

For this reason, there may be a need to minimize circadian disruption due to light at night, and protect neuroendocrine rhythms such as melatonin. The directionality of light may also be a consideration in determining the effects of light on the SCN.

The introduction of artificial lighting (e.g., electric lighting), and the transition from a primarily outdoor agricultural economy to an indoor industrial and information economy has created a world where people may be exposed to biologically-significant levels of light at various hours of day and night, and to relatively reduced illumination during the daylight hours. In some embodiments, lighting systems and lighting devices may be adapted such that differences in directionality of light as it is received by the eyes of individuals are taken into consideration.

FIG. 1 illustrates one example of an indoor environment 100, having artificial lighting provided by ceiling troffer panels 102, pendant light fixtures 103 and wall sconces 104, according to some embodiments.

The indoor environment 100 may be, for example, various locations where individuals are exposed to light from artificial lighting sources, such as workplaces, hospitals, schools, homes, etc., and in these environments 100, there may be light that is provided by a variety of sources. While ceiling troffer panels 102, pendant light fixtures 103 and wall sconces 104 are illustrated by way of example, the lighting sources may include any object that emits light, such as lighting strips, device screens, bioluminescent objects, etc.

In these environments 100, there may be various individuals present who may be exposed to light from the various light sources, such as ceiling troffer panels 102 pendant light fixtures 103 and wall sconces 104. Often, white light is provided from lights utilizing conventional technologies (e.g., incandescent lights, LED lights, tungsten lights, fluorescent lights, neon lights) that provide light that comprises light in a variety of wavelengths. Accordingly, individuals may be exposed to particular wavelengths of light that may have various impacts on circadian function, such as the suppression of various natural functions, etc.

The exposure of the individuals to these wavelengths of light may lead to potentially significant adverse effects on human health, safety and performance as there may be disruption of the circadian timing system by evening, nocturnal or irregularly timed light exposure.

For example, melatonin release at night may be disrupted by a number of mechanisms related to the disruption of the natural day-night cycle of light exposure. Bright daylight exposure (such as in the range of 10,000-100,000 lux) promotes high levels of melatonin release during nocturnal darkness, but spending daytime indoors at reduced level of lights (such as in a range of 100-500 lux) or in dim light or darkness results in suppressed levels of nocturnal melatonin.

Nocturnal light exposure whether it be from electric lights, computer, tablet or smart phone display screens may significantly suppress melatonin secretion. Reduced levels of light or darkness during the day may increase the sensitivity of melatonin to nocturnal light exposure and may increase the suppression of melatonin.

Light exposure during the night may create phase shifts and internal desynchronization of the multioscillator circadian timing system. Reduced light exposure during the day may create increased sensitivity to the phase-shifting and internal desynchronization effects of light exposure at night.

Accordingly, individuals working and/or living on schedules that expose them to increased light at night and reduced light during the day may have suppressed levels of melatonin with flattened amplitudes and/or disrupted circadian timing of melatonin release.

These adverse effects of light at night are primarily mediated by the non-image forming (NIF) visual pathways involving the melanopsin containing retina ganglion cells, the retino-hypothamic tract, the SCN and the pineal gland. Melatonin suppression is one of several diverse NIF physiological responses to light.

Other NIF responses include the pupillary light reflex, the acute effects of light on core body temperature and alertness, and resetting ("shifting") the phase of the master circadian SCN pacemaker.

The NIF system is light intensity dependent and light pulse duration dependent. Under normal day-night cycles, dim white light at night (e.g., below 20 lux) does not significantly suppress nocturnal melatonin levels or phase shift the circadian timing system.

Increasing levels of illumination, and/or durations of light exposure, at night results in greater suppression of nocturnal melatonin, and/or larger phase shifts of the circadian system (such as when the light pulses are delivered at the same phase of the circadian phase response curve).

Human NIF responses to light may also be dependent on light wavelength as responses may differ depending on the particular wavelengths of light contained within light provided from a particular light source.

Short wavelength blue light can suppress endogenous melatonin production and may trigger other NIF responses, including circadian phase shifting during dusk, dawn and nocturnal hours, and promote circadian timing system entrainment during daytime hours and achieving increased levels of human alertness and performance.

The sensitivity of NIF responses to blue light may be due to the presence of a type of photoreceptor in the retina. These photoreceptors, named intrinsically sensitive retinal ganglion cells (ipRGCs), contain a photopigment named melanopsin, which has a peak spectral sensitivity in the blue portion of the visible light spectrum with evidence of peak sensitivity at approximately 480 nm. These ipRGCs are directly connected to central nervous system targets, including the SCN and other targets in the hypothalamus, which may control diverse NIF behaviors.

A number of studies further indicate that, in scenarios comparable to real-world light-dark exposure, blue light sensitivity may exist in the NIF responses of individuals exposed to polychromatic "white" lights with different spectral composition, as measured by correlated color temperature (CCT).

CCT is a metric derived by comparing the appearance of a light source to that of a hypothetical black body heated to incandescence. A black body is an object that absorbs all electromagnetic radiation, and because of this it appears black. When a black body object gets hotter, it changes color: from red to orange, then to yellow, white and finally blue. The temperature of a black body object is measured on the thermodynamic temperature scale in degrees Kelvin (K). The CCT of a particular light source is the temperature (in K) of a heated black body object that most closely resembles the color of that particular light source.

The conventional understanding of the relationship between CCT and spectral power of a light source is that light sources with low CCTs, typically described as "warm", emit a relatively greater proportion of longer wavelength visible light, and are yellowish in appearance. As CCT increases, it becomes more "cool", the relative amount of short wavelength light emitted by the light source increases, and the light appears more bluish. Light sources most commonly used for applications range from ~1700 to ~6500 K, and a CCT of 6500 K represents sunlight.

Because of this relationship between CCT and spectral power of a light, and the sensitivity of the human NIF responses to short wavelength light, lights with a higher CCT (i.e. containing more short wavelength blue light) would be expected, and have been shown to, have a relatively larger impact on melatonin suppression and other NIF responses.

This impact can be beneficial when used during the daytime, when human circadian clocks normally receive light exposure. For example, high CCT blue-enriched lamps may potentially improve mood, alertness, and performance in an office setting during the daytime, compared to lamps of a lower CCT. High CCT lamps may also be more effective than those of a lower CCT for promoting circadian synchronization with the day/night cycle in the Antarctic winter, where the natural light/dark cycle is absent.

However, exposure to lamps with a higher CCT during the night would be expected, and may potentially cause greater melatonin suppression and circadian disruption.

Further, the United States Department of Energy (DOE) published in 2014 a fact sheet describing the impacts of various light sources on several aspects of human physiology, including the NIF responses of the circadian system. The fact sheet reiterates the generally accepted view that the impact of a light source on human NIF responses is dependent upon the CCT of the light source, rather than the type of light itself (e.g., incandescent, fluorescent, LED, etc.). The conclusion was that ". . . CCT can be used as an effective predictor of short-wavelength content across various light source types, and specifically as a predictor of . . . circadian stimulation."

Despite the established relationship between short wavelength light, CCT, and stimulation of the circadian system, most night shift workers work under light levels that will suppress melatonin regardless of CCT. Although lamps with a higher CCT may predictably cause more melatonin suppression and circadian disruption, at light levels commonly used in most night work settings (100-300 lux), even lamps with low CCT may emit sufficient short wavelength light to suppress melatonin and cause circadian disruption. The implication of this finding is that preventing circadian disruption and melatonin suppression may require substantial alterations of the CCT of the light night shift workers are exposed to.

One of alternative approaches to preventing light-induced circadian disruption has been to filter out all short wavelengths below a certain threshold, thus eliminating the wavelengths of light that most effectively suppress melatonin and stimulate other NIF responses. For example, studies have been conducted that may indicate that wearing non-prescription glasses or ophthalmic eyewear that filter out wavelengths shorter than 540 nm, 530 nm, or 480 nm prevents significant melatonin suppression during nocturnal light exposure. Likewise, studies show that light-induced melatonin can potentially be significantly reduced by wrapping a filter around a fluorescent lamp tube to eliminate wavelengths <530 nm at the light source.

Although effective for protecting melatonin and other circadian rhythms, the practical utility of these methods may be limited as the complete absence of short wavelength light may lead to poor color contrast, which presents safety concerns for some night workers.

Removing all short wavelength (blue) light from our color vision may also have the effect of providing a markedly yellow hue, which may be unacceptable in some scenarios and/or applications. Workers may be reliant on their visual acuity in engaging in manual labor, operating machinery and/or in occupations requiring manual dexterity. Further, workers may also rely on their visual acuity for color discrimination to visually distinguish between various objects or parts of objects.

For example, a surgeon's ability to perform surgery may be adversely impacted if the lights being utilized in the operation room have certain wavelengths removed, as the contrast between organs and bodily fluids may be reduced. Similarly, a factory worker may find the experience of working in an environment having lighting that appears to be different from what the worker considers normal lighting uncomfortable and/or confusing.

Accordingly, the lighting industry has sought to provide high quality "white light" with high color rendering to provide the visual acuity and color discrimination necessary for performing indoor tasks at any hour of day or night when they wish to work or undertake other activities utilizing visual perception.

Most lighting installations in the workplace specify a correlated color temperature (CCT, typically in the 3,000 to 5000K range), a color rendering index (CRI of approximately 80 or above) and an illumination level at the work surface of approximately 100-500 lux. Further, high quality white light may be defined as light having light falling within a particular chromaticity tolerance range (e.g., close to the Planckian loci).

There may be various ergonomic, safety, and/or regulatory requirements related to the characteristics of lights provided in some environments, such as workplaces, factories, hospitals, manufacturing facilities, etc.

Further, there may be government energy policies driving the replacement of traditional light sources such as incandescent light bulbs and fluorescent lighting fixtures with energy-efficient light sources.

The energy-efficient light sources, which because of various technological and manufacturing limitations (e.g., such as those experienced in LED production) may potentially increase the risk of blue light exposure.

The residential, industrial and commercial lighting market may further be transitioning from incandescent, halogen and fluorescent lighting to LED lighting, driven by the potential improvements in energy efficiency (lumens per watt), the reduced lifetime cost of LED lighting (LCOL), and the opportunity to integrate smart lighting controls. For example, by 2020, some projections indicate that LED lighting may achieve a 46% penetration of the market for industrial and commercial lamps increasing to 75% by 2030. Government energy conservation policy, rebates and business economics may drive the replacement of current lighting by LED sources. Many of these LED luminaires and bulbs, because of manufacturing limitation and cost considerations in a very competitive market, utilize LED chips which pump blue light that contains light in various wavelength ranges that may impact circadian function (e.g., blue light in the 430-490 nm spectral wavelength range) and hence may potentially induce harmful effects of light at night.

There are two conventional approaches currently offered to reduce the harmful biological effects of blue wavelength light exposure at night and to entrain the human circadian systems to the diurnal phase of the 24-hour environmental light-dark cycle and promote alertness and performance during the day and sleep at night.

The first is to vary illumination level and provide dim light at night and bright light during the day.

The second is to reduce CCT during nocturnal hours and increase it during the day.

There appear to be some deficiencies with both of these approaches to address human circadian system sensitivity to certain wavelengths of light (e.g., blue wavelength (420-520 nm) light) as the approaches appear to compromise some of the purposes for which people use electric light, such as the expectation and need of individuals of high quality light with sufficient color rendering and color temperature for accomplishing their indoor and/or night time tasks.

Accordingly, there may be various limitations to these approaches of relying on varying light intensity and/or color temperature to manage the circadian timing system, and these limitations may have limited the adoption and/or implementation of circadian-healthy lighting applications.

A PCT application (PCT/US2014/032858) has a common assignee and is incorporated by reference, describing an unexpected relative insensitivity of the NIF system to violet light that was not predicted by conventional models of melanopic flux and NIF system spectral sensitivity. The PCT application described that the combination between very low levels of light irradiance in the 430-480 nm (and 430-500 and other variants claimed) wavelength range and a violet light pump with peak emissions between 400 nm and 420 nm (and other variants claimed) could be used to potentially improve the quality of light at night while protecting the circadian timing system from phase disruption and desynchronization, and preventing melatonin suppression and other neuroendocrine disruption and their potentially significant health consequences.

Another significant limitation of current lighting systems is that they are agnostic to the individuals being illuminated by them. At the same geophysical time of day different individuals exposed to illumination from a lighting system (luminaire, lamp or bulb) may have markedly different circadian phases, depending on their prior history of work-rest schedules, and/or sleep-wake schedules as a result of working rotating shift work schedules, recent trans-meridian time zone travel, or their individual orientation to the day night cycle. Individuals vary considerably in their orientation to day and night on a morningness-eveningness scale. Morning types tend to rise early and they feel and perform best during the morning hours. Evening types tend to rise late in the morning and they feel at their best late in the evening. It has recently been shown that these characteristics are genetic in nature, manifested in differences in circadian periodicity and entrainment that are independent of age, sex and ethnic heritage.

Some individuals may also be unavoidably exposed to light. For example, an individual may have limited mobility and may, by reason of physical disability, injury, or due to the nature of their work or activity being performed, be unable to move sufficiently to avoid exposure from one or more light sources. For these individuals, there may be potential detrimental impacts resultant from exposure to light from conventional lighting systems as the light may impact their circadian functioning and, for example, cause irregular sleeping/waking schedules.

For example, a patient disposed on a bed at a hospital may not be able to move sufficiently to avoid exposure to light from one or more light sources present in a hospital room.

Recent studies have also pointed to a significant contribution by green light wavelengths to melatonin suppression and circadian phase-shifting, suggesting that exposure to these wavelengths should be controlled in addition, to or independently from controlling blue wavelength exposure.

A study indicated that monochromatic green light (555 nm) during the first 2 hours of a 6.25 hour period of exposure starting approximately 2 hours before a person's habitual bedtime was almost as effective as blue light exposure (460 nm) in suppressing melatonin.

However, the study also indicated that the effectiveness of green light in suppressing melatonin appeared to decay exponentially over the six hours of exposure, whereas the effectiveness of blue light remained constant. The study speculated that this rapid decay was due to the temporal response properties of the medium and long wavelength cone photoreceptors that the study authors suggested were driving the response.

Rather than a duration-dependent decay in the effectiveness of green light to suppress melatonin, this observed decline may instead represent a circadian variation in the spectral sensitivity of melatonin suppression. With this alternative interpretation of the data, light-induced melatonin suppression and circadian phase-resetting may be especially sensitive to green light in the early biological evening, with a decline in this sensitivity across the biological night-time.

The suppressive effects of green light may therefore be a transient result, and systems and/or methods for protecting individuals from circadian suppressive effects may be tuned and/or adapted such that these circadian suppressive effects are avoided or reduced. As the effects may be transient (e.g., during only a portion of a "night" period), in some embodiments, these wavelengths are only attenuated to reduce evening light exposure (e.g., a first half of night period).

Further studies have indicated that under naturalistic conditions (e.g., where pupils are not pharmacologically dilated, etc.), green light in the evening and early biological night-time may be as effective or, in some scenarios, more effective than blue light and that the relative effectiveness of green light decreases across a night, such that blue light is relatively more effective than green light for influencing circadian responses in the late night and early morning hours.

Accordingly, light sources and/or lighting systems may also need to be adapted and/or configured to not only protect for blue evening light exposure, but also protect from certain green wavelengths that may be biologically active at specific evening and early night-time hours. For the remainder of the biological night-time, protecting from blue light exposure only may be sufficient for reliable protection of circadian rhythms.

In some embodiments, a light source may be provided for evening and early night-time use only (the "evening" light source) which may be adapted to provide a peak in the intensity of emitted light at approximately 415 nm and very low levels of light emission in the 430-520 nm wavelength range, produced by a light source with a spectral power distribution alone or in conjunction with the use of a filter to attenuate wavelengths between 430-520 nm, and which provides potential protection from the disruption of the circadian timing system by evening and early night-time light and which may reduce the suppression of melatonin release while providing a high quality white light suitable for work and other tasks.

In some embodiments, the wavelength range for the low levels of light emission may instead be 430 nm-560 nm; 430 nm-540 nm and among others.

In some embodiments, a light source may be provided for evening use during the time interval ranging from 3 hours before to 3 hours after an individual's habitual bedtime, which provides a portion (e.g., approximately 15%, 20%, 25%, 30%) of the total visible (400-700 nm) spectral power in the 400 nm-430 nm wavelength range and less than 3% in the 430 nm-525 nm range, which provides potential protection from the disruption of the circadian timing system and may reduce the suppression of melatonin release specifically during these evening hours, while providing a quality white light suitable for work and other tasks.

In some embodiments, the evening light source may be provided from sunset until 3 hours after habitual bedtime, or, the time of the dim light melatonin onset (DLMO) until habitual bedtime.

In some embodiments, the evening light source may provide a spectral power distribution of <0.1%, <1%, <2% <3%, <5% or <8% in the 430-525 nm range.

In some embodiments, the evening light source may provide a percentage of light between 400-430 nm equal or greater than 15%, equal or greater than 20%, equal or greater than 25%, or equal or greater than 30%.

In some embodiments, the evening light source may be provided for use during the time interval ranging from 3 hours before to 3 hours after an individual's habitual bedtime, which provides a portion (e.g., approximately 15%, 20%, 25%, 30%) of the total visible (400 nm-700 nm) spectral power in the 400 nm-430 nm wavelength range and a blue depleted window with less than 3% of total visible power in the 430 nm-490 nm range, and a green-depleted window of less than 3% of total visible power in the 520 nm-560 nm range designed to provide protection from the disruption of the circadian timing system and may reduce the suppression of melatonin release specifically during these evening hours, while providing a quality white light suitable for work and other tasks. In some embodiments, the evening is considered a "biological early night" as distinguished from a "biological late night". During a "biological late night", there may be transmission and/or emission in the green light wavelengths.

In some embodiments, the green-depleted window may be the range of wavelengths between approximately 490 nm-560 nm, 520 nm-570 nm, 510 nm-560 nm, etc. A light may be adapted for suppression of the green-depleted window, for example, blocking and/or attenuating the range of green wavelengths which are active in transient melatonin suppression from approximately 490 nm to 560 nm, or any of the other ranges shown above.

In some embodiments, a light source for late night time use only (described as an "night" light source) may be provided producing a peak in the intensity of emitted light at approximately 415 nm and very low levels of light emission in the 430 nm-490 nm wavelength range which provides potential protection from the disruption of the circadian timing system by late night time light exposure and may reduce the suppression of melatonin release while providing a high quality white light source compatible with the preservation of circadian rhythms, and delivered at a CCT and/or CRI suitable for work and other tasks.

In some embodiments, a night light source may be provided for use during the time interval ranging from 3 hours after an individual's habitual bedtime until habitual wake time, which provides approximately 20% of the total visible (400-700 nm) spectral power in the 400-430 nm wavelength range and less than 3% in the 430-490 nm range which provides potential protection from the disruption of the circadian timing system and may reduce the suppression of melatonin release while providing a quality white light source with a CCT and CRI suitable for work and other tasks.

In some embodiments, the night light source may be configured for use during time interval from 3 hours after a person's habitual bedtime until sunrise.

In some embodiments, a lighting system may be provided, the lighting system comprised of three independently controlled light sources including an evening light source, a night light source, and day light source where the evening light source is as described in some of the above embodiments, and the night light source is as described in some of the above embodiments and the day light source provides an increased level of light between 430-490 nm wavelengths to provide a strong entraining signal to the circadian clock during the daytime hours, and to thereby promote circadian entrainment of circadian rhythms.

Lighting Devices and/or Systems Adapted for Circadian States

Some embodiments described herein provide devices, systems and methods related to lighting systems, light sources, control systems and/or illumination sources. More specifically, some embodiments relate to lighting systems, illumination sources and/or light sources that may be configured to illuminate having particular characteristics favorable for various circadian states. In some embodiments, the lighting systems and/or light sources can be used for periods of time (e.g., on a 24 hour shift) without producing significant circadian disruption. There may be advantages, such as improvements in alertness and performance the potential for long-term improvements in shift worker health, and accordingly, the embodiments may have potential application in the large and growing segment of the modern economy that requires night work, shift work and/or work under artificially lit conditions.

Some embodiments described herein are directed to the protecting and/or entrainment of circadian patterns and/or rhythms, adapting the spectral characteristics and composition of light provided by the light sources to facilitate exposure patterns suitable for the appropriate times of day and night so that an individual's circadian rhythm may be corrected and/or modified. In some embodiments, exposure patterns are also adapted in relation to evening and/or interim durations between day and night (e.g., to take into consideration green light exposure, and saturation/limited effects thereof).

In some embodiments, the devices, systems and methods described provide illumination configured for various circadian states wherein the illumination maintains a correlated color temperature (CCT), color rendering index (CRI) and/or a light intensity comparable or equal to other illumination in a particular environment. In some embodiments, the devices, systems and methods are matched with one another so that in a particular lighting system, the illumination is maintained at a CCT, CRI and a light intensity even when light sources related to the lighting system are varied (e.g., complementarily switched on and off, the relative proportion of intensities between a plurality of lights varied).

In some embodiments, the illumination between one or more light sources is matched such that an individual of average visual acuity would not be able to perceive a difference in the illumination provided by the light sources (e.g., during the switch from a night-configured light source to a day-configured light source, or vice versa). Such illumination may be controlled, for example, by balancing the SPD of light through increasing/decreasing light output in various ranges (e.g., purple, orange) to compensate for light reduction in circadian active wavelength ranges (e.g., blue, green). There may be a plurality of lights and/or lighting devices, and these lights may be adapted such that on balance, the difference in SPD and illumination is difficult and/or impossible to perceive. Ratios of lighting, intensity, modified directionality, reflectors, etc., may be utilized.

For example, the light sources may be matched such that their CIE 1931 chromaticity coordinates are approximately within a 2 step MacAdam ellipse of each other and/or the difference between their CCT values is less than 5%. In some embodiments, the matching may include an approximately matching that may not be entirely white, but close enough such that an individual is less perturbed by the change or unable to perceive the change (even if the change does bring the light outside of a strict definition of white light).

In some embodiments, the difference between their CCT values is 500K, 200K, 100K, 50K or 25K.

In some embodiments, the light sources may be matched such that their CIE 1931 chromaticity coordinates are within a 2 step MacAdam ellipse of each other and the difference between their CRI values is less than 5%.

In some embodiments, the light sources may be matched at least a 14 step MacAdam ellipse of each other. In some embodiments, the light sources may be matched at least a 12 step MacAdam ellipse of each other.

In some embodiments, the light sources may be matched such that the difference between their CIE 1931 chromaticity coordinates are within a 2 step MacAdam ellipse of each other and the difference between their light intensity values is less than 10%.

In some embodiments, at least one of the CCT, CRI and light intensity are matched, and the other two values may be the same or within an acceptable range. For example, two light sources operating complementarily may be matched in terms of CCT, and the differences in CRI and light intensity may be within an acceptable range.

In some embodiments, the composition (e.g., the spectral power distribution) of illumination provided may be configured and/or adapted such that the illumination is adapted for a particular circadian state. For example, the illumination may be adapted for reduced impact on circadian state (e.g., significantly attenuating/filtering out particular ranges of wavelengths) or, in some embodiments, the illumination may be adapted to impact the circadian state (e.g., to entrain the circadian rhythm of an individual).

The attenuation of wavelengths may be provided through various apparatuses and/or methods. For example, filter elements may be employed to attenuate and/or remove various wavelengths from incident light. Other means may also be used, such as specially configured light sources providing light having a particular spectral power distribution (e.g., using phosphors on an LED), attenuating films, translucent materials, etc.

The spectral power distribution is the distribution of spectral power across various wavelength ranges of visible light. For example, the spectral power distribution for a particular spectral power window is the percentage of visible wavelength (approximately 400-700 nm) light spectral power in that particular range of wavelengths.

The illumination from the light source may be composed with light such that the spectral power distribution of the emitted light is varied according to a desired circadian state (e.g., time of day), so as to have/avoid various effects on an individual's circadian system (e.g., regulating and synchronizing the human circadian timing system and/or protecting against the harmful effects of specific spectral wavelengths between a time range, such as night time).

Devices, systems and methods configured to reduce the impact of illumination on circadian states while maintaining a constant and/or suitable CCT, CRI and/or light intensity may be useful in situations where, for example, individuals are performing work and/or other human activities during periods of time where illumination from artificial light sources is required. During these periods of time, the light from the artificial light sources, if not properly composed, may be disruptive to an individual's circadian state.

Further, there may be various advantages associated with maintaining a CCT, CRI and/or a light intensity comparable or equal with other illumination, such as consistency and/or continuity in the experience of an individual, maintaining color differentiation, maintaining contrast, etc. For example, it may be desirable that individuals are not able to perceive a change in the composition of the illumination provided by a light source. Such changes may be disruptive and/or distracting to an individual and may impact the ability of an individual to carry out tasks and/or activities.

Figure 2:
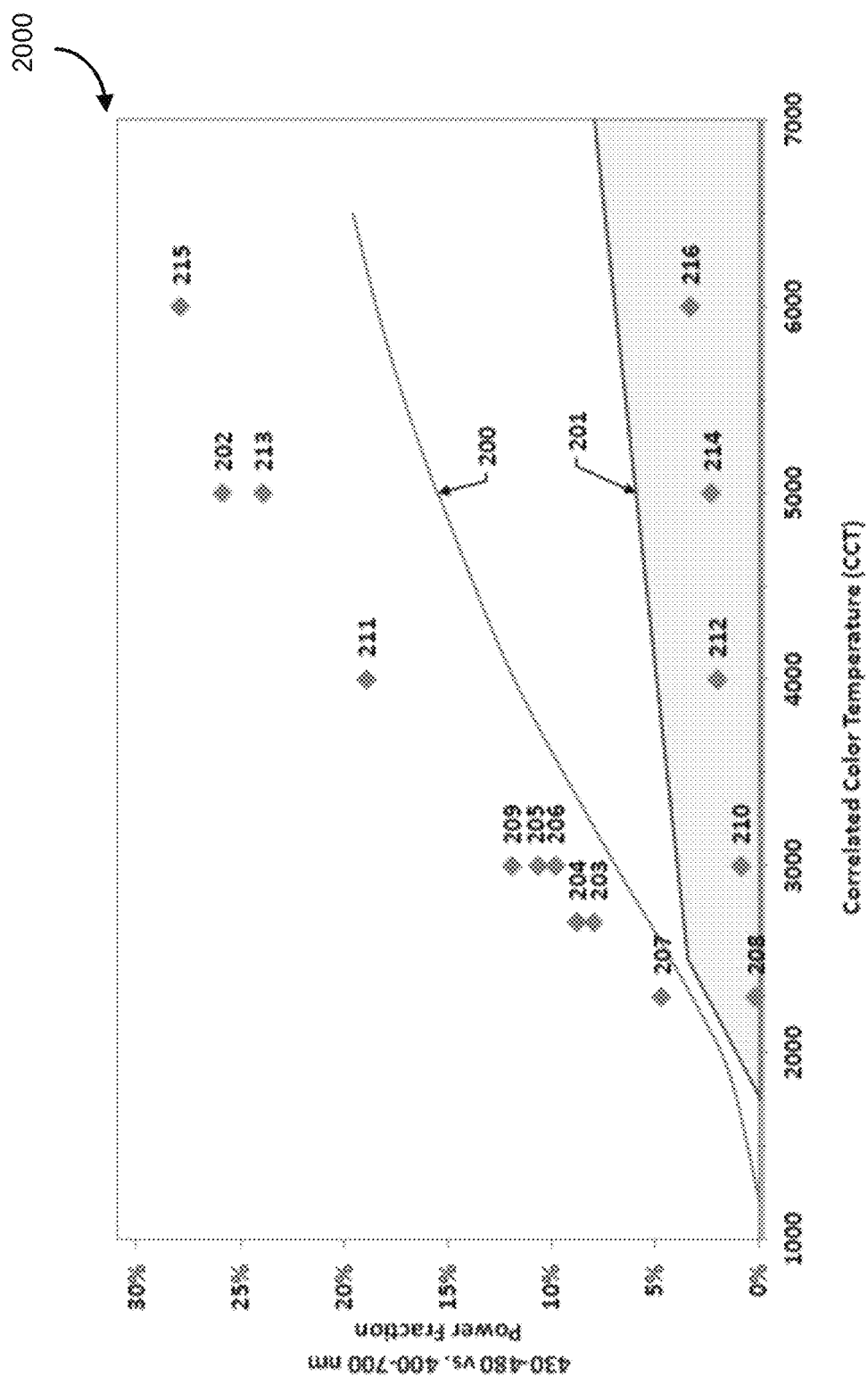
FIG. 2 is a graph depicting a relationship between the power of light delivered in the circadian active blue wavelength range relative to the total power of visible light between 400 and 700 nm and the CCT of conventional lighting systems, as well as some of the lighting systems described in this specification, according to some embodiments.

FIG. 2 is a graph 2000 depicting a relationship between the power of light delivered in the circadian active blue wavelength range relative to the total power of visible light between 400 and 700 nm and the CCT of conventional lighting systems, as well as some of the lighting systems described in this specification, according to some embodiments.

The Y-axis is indicative of the percentage of spectral power of the visible light (400-700) that is directed at wavelengths within the 430 nm-480 nm wavelength range. The X-axis is indicative of the CCT. Shown in FIG. 2 is a line representing the relative percentage of 430-480 nm light in the 400 nm-700 nm visible spectrum at each point of the black body radiator curve as CCT is increased 200 and a shaded area representing an effective zone for night luminaires which may minimize the disruption of melatonin or circadian function 201.

Various points 202-216 were mapped to the axes based on conventional lighting systems and these are indicated as points on the graph representing the color temperature and the relative irradiance between 430-480 nm for some commercially available lighting products.

It is important to note that these commercial available lights all have significant percentages of spectral power in the 430 nm-480 nm wavelength range, and are mostly above the line representing the relative power of the 430 nm-480 nm wavelength range of the black body curve 201 and trend upwards as the CCT increases. For example, FIG. 2 indicates that standard commercially available LED lighting generally provides 6-25% visible irradiance in the 430 nm-480 nm window.

The examples of existing commercially available LED luminaires are indicated by diamonds including a Cree™ 4Flow2700K lamp 203; a Philips™ Slim Style Dimmable Soft White 2700K lamp 204; a Philips™ Par30 Bright White 3000K lamp 205; and a GE™ Lumination Luminaire 3000K lamp 206. In addition the pairs of day and night luminaires that are embodiments are plotted in which each member of the pair has the same color temperature and provide indistinguishable white light while providing light which with the day lamp either stimulates or with the night lamp protects the circadian system. These include a 2300K Day lamp 207; a 2300K Night lamp 208; a 3000K Day lamp 209; a 3000K Night lamp 210; a 4000K Day lamp 211; a 4000K Night lamp 212; a 5000K Day lamp 213; a 5000K Night lamp 214; a 6000K Day lamp 215; and a 6000K Night lamp 216.

It is conventionally assumed, including by the US Department of Energy, that the relative spectral power in within the 430-480 nm wavelength range is largely determined by the CCT.

The applicants have demonstrated that light sources which emit less than 4%, 3%, 2% 1% 0.1% of total visible spectral power in the 430 nm-490 nm range have protective circadian effects including the restoration of nocturnal melatonin levels. The light sources may be adapted for and/or configured for various types of applications, such as for night time use, day time use, and/or for various transition states between night and day time use. Various technologies, structural elements and/or physical elements may be utilized to cause the variation of the spectral power distribution of the lights, such as the application of various filters or design choices that influence the composition of light emitted by the light sources shown in FIG. 3 in system 300, such as 302, 304 and/or 306.

Various types of light sources may be provided, including a light source for night time use which provides a peak in intensity of emitted light at approximately 415 nm and very low levels of light emission in the 430 nm-490 nm wavelength range. The light source for night time use may also be configured to provide a light source, such as a white light source, having particular characteristics, such as suitable CCT, CRI and/or light intensity for use in various environments such as workplaces, homes and hospitals. For example, suitable characteristics may include, for example, a CCT in the 3,000 to 5000K range, a CRI of approximately 80 or above and/or an illumination level at a work surface of approximately 100-500 lux.

The low and/or very low levels of light emission in the 430 nm-490 nm range may be caused through the use of various means and/or structural elements, such as a LED and/or phosphor designed for reduced generation of light within the wavelength band. Further, additional filter elements, etc., can be applied to a lighting source to filter out particular wavelengths of light. For example, a filter may be applied to reduce the spectral power of visible light in the 430 nm-490 nm wavelength range to levels below 1%. Other techniques and/or structural elements may be considered.

In the example of a night light, the night light may require a reduction in light in the blue wavelength ranges. However, the night light may need to increase the light provided in the violet wavelength ranges to compensate for this reduction in blue light so that the light produced is not overly yellow/orange.

Further, the low levels of light emission provided by the light source for night time use in the 430 nm-490 nm wavelength range may help reduce the disruption of the circadian timing system of light at night and potentially reduce the suppression of melatonin release, while providing a high quality light source at a color temperature and color rendering index suitable for work and other tasks.

In order to maintain a particular CCT, CRI and/or light intensity, the light source is balanced between various spectral power distributions across spectral power windows outside of a spectral power window whose power has been depleted (e.g., the blue wavelength window).

As described above, various studies have indicated that there may a need for light sources having spectral power distributions where spectral power provided in particular wavelength ranges are significantly increased, attenuated and/or reduced. Accordingly, to maintain particular light characteristics, such as a comparable CCT, CRI and/or light intensity, the power distributed to the other wavelengths ranges can be increased to compensate for the reduced power distributed to the particular wavelength ranges (e.g., the blue wavelength range).

In some embodiments, the light source for night time use may be adapted to and/or configured to provide approximately 15-60% of the total visible (400-700 nm) spectral power in the 400-430 nm wavelength range and less than 3% (or, in some embodiments, 4, 2, 1, 0.1%) in the 430-490 nm range, while providing a quality light source with a CCT, CRI and/or light intensity suitable for work and other tasks. In other embodiments, the light source for night time use provides approximately 20-60%, 25-55%, 25-60%, 15-55%, and/or 20-55% of the total visible power in the 400-430 nm wavelength range.

In some embodiments, the light source for night time use may be adapted to and/or configured to provide approximately 15-60% of the total visible (400-700 nm) spectral power in the 400-430 nm wavelength range and less than 0.1% in the 430-490 nm range while providing a quality light source with a CCT, CRI and/or light intensity suitable for work and other tasks. The light source for night time use may be also be referred to as a 430-490 nm depleted light source.

In some embodiments, a light source for day time use may be provided. The light source for day time use may adapted to and/or configured to provide approximately 0-10% (in other embodiments, 0-5%, 0-2%, etc.) of the total visible (400-700 nm) spectral power in the 400-430 nm range and approximately 4-30% (in other embodiments, approximately 5-30%) in the 430-490 nm range while providing a quality light source with a CCT, CRI and/or light intensity suitable for work and other tasks. The light source for day time use may also be referred to as a 430-490 nm enriched and/or non-depleted light source.

In a preferred embodiment, the light sources described throughout this specification may provide, for example, a high quality white light. Other types, colors and/or characteristics of emitted light may also be contemplated in some embodiments, such as a red light (e.g., for some types of greenhouses), yellow/orange light (e.g., for semiconductor fabrication), etc. For these environments, lighting sources adapted in embodiments described may be matched to have acceptable CCT, CRI, light intensity and/or other characteristics suitable for the particular environment that the lighting sources are operating in.

Further, the light sources described may also be adapted and/or configured to maintain a constant or near-constant CCT, CRI and/or light intensity (e.g., lux or foot candles) on a task or individual in conjunction with other lighting present and/or experienced by an individual. For example, the light sources may be adapted and/or configured to match other lighting in a workspace, a factory, etc., so that an individual is not disrupted by (or, in some cases, even perceive) the change in lighting.

In some embodiments, two or more light sources may be used in conjunction to provide a lighting system that may be adapted and/or configured to maintain a constant or near constant CCT, CRI and/or light intensity (e.g., lux or foot candles) on a task or individual for a period of time (e.g., 24 hours a day), while varying the spectral power distribution of the light wavelengths according to human circadian timing system requirements. It is understood that the two or more light sources may be provided in the same housing, and may operate complementarily to one another.

In some embodiments, various combinations of night-adapted and day-adapted LEDs may be used in connection with dawn and dusk transition. Some further embodiments include the use of a boost in power of the blue-enriched light or an extra set of day-adapted LEDs in the morning for the entrainment of circadian rhythms. In some embodiments, combinations are provided that are adapted for evening LEDS that may operate in conjunction with a combination of some or all of the night-adapted and day-adapted LEDs.

In some embodiments, the light sources are adapted such that overall lighting characteristics are provided within a pre-determined comparable range (e.g., CCT, CRI, light intensity, chromaticity ranges) relative to the aggregate incident lighting provided by the light sources when the light sources are activated but not controlled to have circadian-significant attenuation along the circadian active wavelength range. For example, the light sources may be configured and controlled such that the lighting conditions provided are not perceptibly different than conventional lights (e.g., so that an individual does not notice or at least is not perturbed by any changes in lighting conditions).

For example, as described further in this specification, various compensation techniques may be applied (e.g., the use of compensation across various wavelengths through actively increasing or decreasing the prevalence of light in particular wavelength ranges), and various light sources may be controlled in relation to their operating parameters (e.g., dimmed, turned on and/or off).

Figure 3:
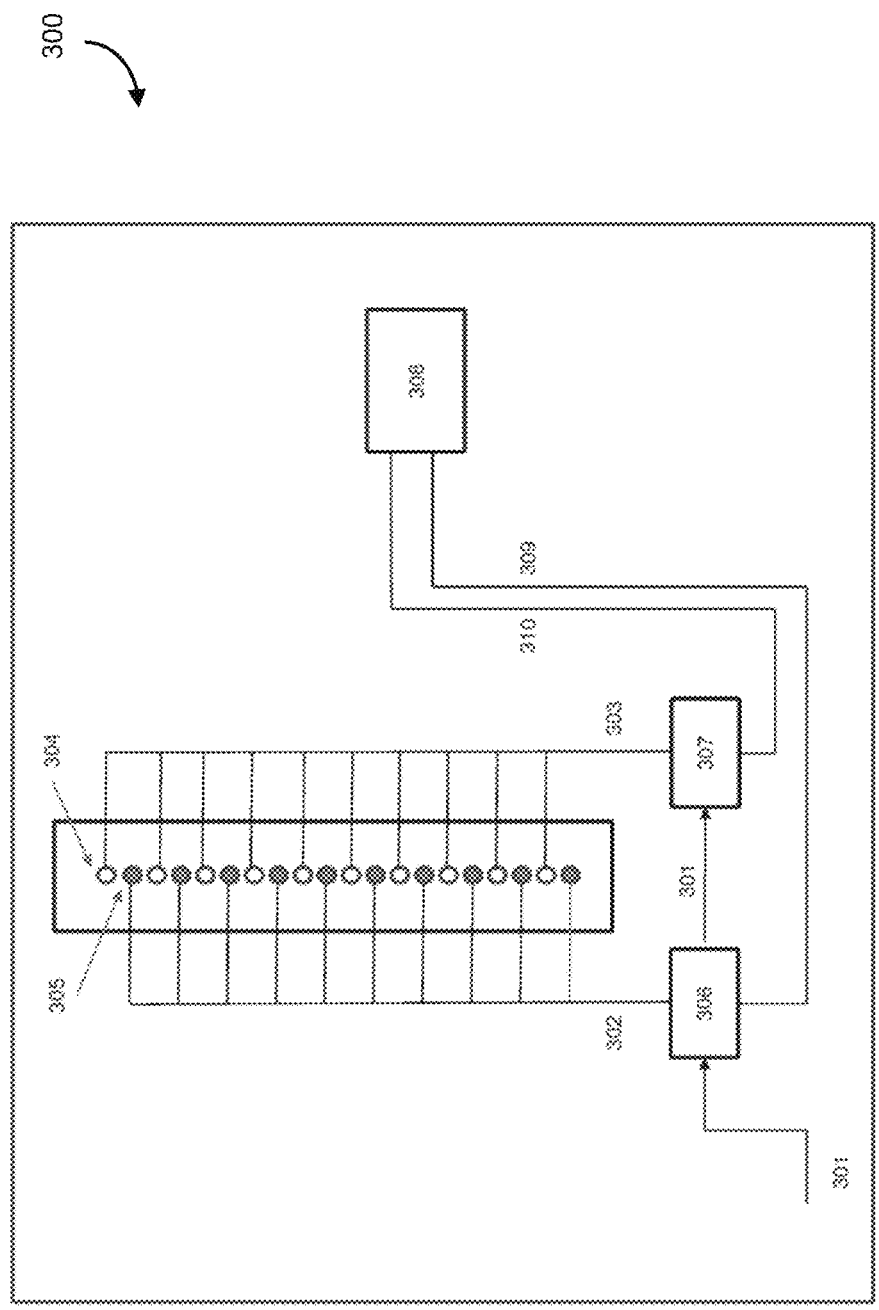
FIG. 3 is a schematic diagram of a lighting system that may be configured in relation to one or more circadian states, according to some embodiments.

FIG. 3 is a schematic diagram of a lighting system 300 that may be configured in relation to one or more circadian states, according to some embodiments.

Lighting system 300 may be comprised of a first light source 304 and a second light source 305, as well as a control system 308.

The first light source 304 may be configured to operate as a night light source as described above, and the second light source 305 may be configured to operate as a day light source as described above.

The first light source 304 may be driven by a connection 302 to a driver 306, which may in turn supply control voltage and current to the first light source 304 in such a manner that light source 304 may be dimmed and brightened in accordance with instructions which may be sent via a connection 309 that carries dimming or brightening instructions from a controller 308.

The second light source 305 may be driven by a connection 303 to a driver 307, which may in turn supply control voltage and current to the second light source 305 in such a manner that light source 305 may be dimmed and brightened in accordance with instructions which may be sent via a connection 310 that carries dimming or brightening instructions from a controller 308.

The first light source 304 may be matched with the second light source 305 such that their CIE 1931 chromaticity coordinates are within a 2 step MacAdam ellipse of each other and the difference between their CCT and/or CRI values is less than 5%. A MacAdam ellipse refers to the region on a chromaticity diagram which contains colors which are indistinguishable to the average human eye from the color at the center of the ellipse.

In some embodiments, the CCT may be the 3000 to 5000K range, a CRI may be provided at approximately 80 CRI or above and/or an illumination level may be provided at a work surface of approximately 100-500 lux.

Potential advantages of having matched light sources may be the ability to switch from one light source to another with potentially reduced and/or minimal disruption to the circadian rhythm of one or more individuals exposed to the light from the light sources.

Other values and/or ranges of CCT, CRI and/or illumination levels may be contemplated, and may vary, for example, depending on the particular environment in which the lighting sources may be operating in. In some embodiments, the CCT may be in the 1000K-16000K range (or preferably 1900-7000K or 2600-4000K), a CRI may be approximately 60 or above, and an illumination level may be approximately 10-750 lux.

The control system 308 may be configured for interconnection and/or communication with the first light source 304 and the second light source 305. The control system 308 may control various characteristics associated with the operation of the first light source 304 and/or the second light source 305, such as determining whether a light source should be turned on, the power level at which a light source should be actuated, the application of various filters, the balance of power between a plurality of light sources, etc.

The control system 308 may be adapted such that there may be various subunits and components provided that receive various types of high-level instructions that are then encoded and/or transcoded into machine-interpretable instructions that may be transmitted to the various light sources 304 and 305.

The lighting system 300 is provided by way of example, and other embodiments may be contemplated. For example, the first light source 304 may not necessarily be in the same housing as second light source 305, and, for example, may be provided from a different type of light fixture (e.g., the first light source 304 may be a wall sconce, and the second light source 305 may be a ceiling light). There may be more than two light sources and the control system 308 may be configured to interoperate with a plurality of light sources greater than two.

The control system 308 may be adapted such that an overall and/or aggregate incident lighting from all of the light sources (e.g., 304 305) may be controlled to effect various circadian-related outcomes. For example, the machine-level control commands may be adapted and encapsulated to control the light sources 304 and 305. The machine-level control commands may include specific machine-instructions (e.g., to control voltages, the presence of filters, the use of phosphors) that are adapted such that the aggregate incident lighting provided by the light sources provides light with a spectral power distribution having circadian-significant attenuation along a circadian active wavelength range during durations of time when the individual is in a biological night state, while providing overall lighting characteristics within the pre-determined comparable range relative to the aggregate incident lighting provided by the one or more light sources when the one or more light sources are activated but not controlled to have circadian-significant attenuation along the circadian active wavelength range.

In some embodiments, a lighting system may be provided that combines a night light source and a day light source, as described in embodiments above. The night light source and the day light source may be configured for cycling, by a control system (e.g., a timer) between the night light source and day light source depending on the particular target circadian state for a given time (e.g., the day light source during daytime hours and the night light source during night time hours). The night light source and the day light source may be matched such that the same CCT, CRI and/or illumination intensity as the night light source, and whereby the CCT, CRI and illumination intensity can remain unchanged during a period of operation (e.g., 24 hours a day). Accordingly, the exposure of an individual to light wavelengths in the range between 430-490 nm may be varied depending on various factors (e.g., time of day), and the particular circadian rhythms of one or more individuals.

In some embodiments, a lighting system may be provided that combines a night light source and a day light source, where the night light source provides approximately 15-60% of the total visible (400-700 nm) spectral power in the 400-430 nm wavelength range and less than 3% (or 4%, or preferably less than 1%) in the 430-490 nm range, and the day light source provides approximately 0-10% of the total visible (400-700 nm) spectral power in the 400-430 nm range and approximately 4-30% in the 430-490 nm range while providing the same CCT, CRI and illumination intensity as the night light source, and whereby the CCT, CRI and illumination intensity can remain unchanged for a period of time (e.g., 24 hours a day) while cycling between the day light source during the daytime hours and the night light source during the night time hours thereby varying the exposure of an individual to light wavelengths between 430-490 nm.

In some embodiments, a lighting system may be provided that combines a 430-490 nm depleted light source and a 430-490 nm enriched light source, where the 430-490 nm depleted light source and the 430-490 nm enriched light source can be independently controlled so that whatever percentage of the total light (0-100%) is emitted by the 430-490 nm depleted light source or the 430-490 nm enriched light source the same CCT, CRI and illumination intensity are provided by substantially varying the exposure of an individual to light wavelengths between 430-490 nm.

In some embodiments, the light sources may be provided as two LED strips and/or or clusters of LEDs (or alternate types of LED on the same board). One LED associated with a phosphor may provide the day configuration of the light, and the other is adapted to provide the night light. The day light can be a standard LED+phosphor which provides a spike in the biologically significant blue wavelengths.

Figure 4:
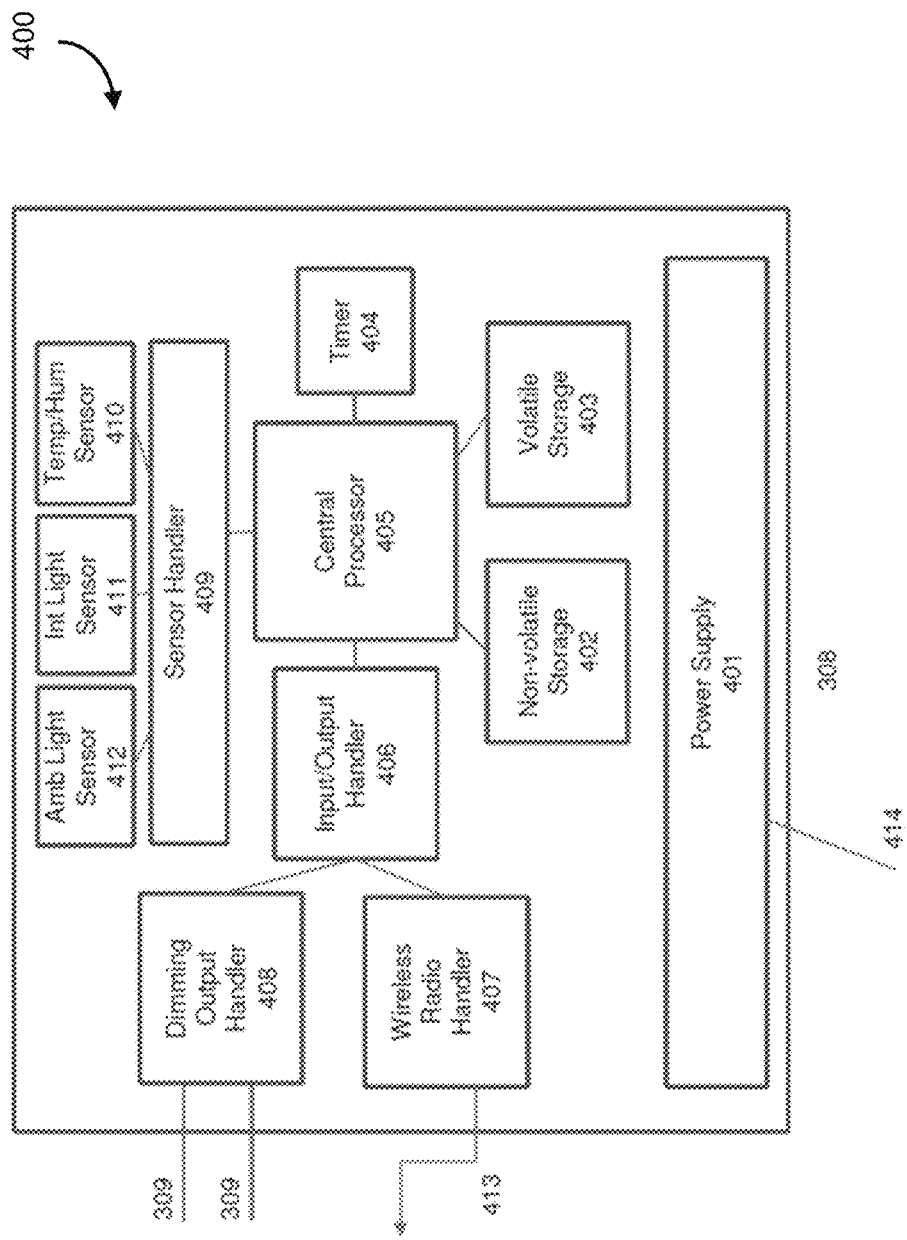
FIG. 4 is a block schematic diagram of a control system, according to some embodiments.

FIG. 4 is a block schematic diagram 400 of a control system 308, according to some embodiments. The control system 308 may be comprised of a power supply 401, a central processor 405, non-volatile storage 402, volatile storage 403, a timer 404, an input/output handler 406, a wireless radio handler 407, a dimming output handler 408, and a sensor handler 409 with various sensors which may include a temperature/humidity sensor 410, an interior light sensor 411, and an ambient light sensor 412. The dimming output handler 408 provides a dimming or brightening signal 408 and 409 to first light 304 and second light 305 (shown in FIG. 3) respectively. The wireless radio handler may receive control and configuration information via wireless signal 413.

The central processor 405 may be utilized for controlling the other components, issuing control commands and machine-interpretable instructions.

For example, control commands may include signals configured for toggling the operational state of a light, to dim the light, to modify characteristics of the light output (e.g., turn on a violet light emitting source, add a filter, power a particular LED), among others. Such control commands may be transferred over various frequencies, and instructions may be adapted at various levels of abstraction, such as application level commands, networking packets, and/or physical layer communications.

For example, instructions may be sent over a Zigbee™ standard light link, and the control system 308 could be utilized as a controller node, sending instructions to one or more controlled nodes. In some embodiments, the lights may create their own mesh network, especially if the lights are placed at a distance to one another, and commands may be relayed through the mesh network rather than originating at a centralized source for each light.

The control system 308 may be implemented using software, hardware and/or a combination of software and/or hardware components. In some embodiments, the control system 308 may be implemented using various computing devices, field-programmable gate arrays (FPGAs), logic gates, chipsets, etc. In some embodiments, the control system 308 may be a timer and/or physical on/off/dim switches.

Program code may be applied to data elements to perform the functions described herein and to generate output information. The output information may be applied to one or more output devices. In some embodiments, the wireless radio handler 407 may be a wired external data interface. In embodiments in which elements may be combined, the external data interface may be a software communication interface, such as those for inter-device or inter-process communication. In still other embodiments, there may be a combination of communication interfaces implemented as hardware, software, and combination thereof.

The control system 308 may be configured for various types of circadian programs, such as a timed program, or various entraining programs. These circadian programs may be based, for example, on an individual's desired circadian state adjustment (e.g., to adjust for jet lag, upcoming shift work), and may be set on various timers and/or durations. The circadian programs may be determined to take into consideration night, day, evening, and/or other types of circadian requirements.

In some embodiments, the circadian programs also track total light exposure in the designated evening periods such that the total exposure may be monitored to determine when the total exposure saturates a pre-defined evening period exposure level (e.g., established using one or more data processing logical rules, or empirically determined through measurements of activity levels, biological feedback, and/or human provided feedback). In some embodiments, the circadian programs are context or activity-specific, establishing different values dependent on a scheduled activity (e.g., extracted from a person's calendar or work schedule data).

For example, total irradiance in the 430-490 nm window that may be required to entrain the circadian system may be approximately 8 $\mu W/cm^2/sec$. or 10 $\mu W/cm^2/sec$ or 20 $\mu W/cm^2/sec$ or more Conversely, to avoid circadian phase shifting or melatonin suppression, the total irradiance in the 430 nm-490 nm window may need to be reduced to less than 3 $\mu W/cm^2/sec$ or less than 1 $\mu W/cm^2/sec$ or less than 0.1 $\mu W/cm^2/sec$.

The circadian programs may be provided through external systems providing data through an interface 413.

In some embodiments, the control system 308 controls a plurality of light sources to implement one or more circadian timed programs. An example circadian timed program, for example, may include the activation of 100% emission by the 430-490 nm enriched light source to provide a strong entraining signal for the circadian timing system that would normally be applied within an hour (or two hours before or after dawn) so as to help ensure and/or implement entrainment of the circadian timing system to the natural environmental day-night cycle even if the individual remains indoors. In this program, a 50% contribution of the 430-490 nm depleted light source and 50% contribution of the 430 nm-490 nm enriched light source may be combined to provide lighting for regular daytime use, and the 430 nm-490 nm depleted light source may be utilized as the 100% source of emitted light during nocturnal hours. Other proportions may be considered, such as 45%/55%, 55%/45%, 60%/40%,40%/60%, 30%/70%, etc.

Further, during the course of the circadian timed program, the CIE 1931 chromaticity coordinates, CCT, CRI and illumination intensity can remain constant or near-constant (e.g., unchanged for 24 hours a day) while providing a strong circadian entrainment signal configured to potentially boost circadian rhythm amplitude, stabilize circadian entrainment and/or promote performance and health of individuals exposed to the light from the lighting system.

In some embodiments, a lighting system is provided which combines a 430-490 nm depleted light source and a 430-490 nm enriched light source, where the night light source provides approximately 15-60% of the total visible (400-700 nm) spectral power in the 400-430 range and less than 3% in the 430-490 nm range, and the day light source provides approximately 0-10%of the total visible (400-700 nm) spectral power in the 400-430 nm range and approximately 4-28% (preferably greater than 8%) in the 430-490 nm range while providing the same or similar CIE 1931 chromaticity coordinates, CCT, CRI and illumination intensity as the night light source, and whereby the CIE 1931 chromaticity coordinates, CCT, CRI and illumination intensity can remain unchanged for a period of time (e.g., 24 hours a day) while cycling between the day light source during the daytime hours and the night light source during the night time hours thereby varying the exposure of an individual to light having wavelengths between 430 nm-490 nm.

As described in some embodiments, various lighting sources having features directed towards maintaining circadian rhythms can be utilized for various purposes, such as circadian timing system entrainment, including circadian phase, amplitude and periodicity regulation. The use of the lighting systems and/or light sources described above may potentially reduce some of the harmful effects of light at night, including the flattening and disruption of neuroendocrine functions such as melatonin.

In contrast to currently available solutions, lighting systems and/or light sources described above do not require variations in light intensity or CCT to manage human circadian rhythms and provide potential health and performance benefits for the illuminated individuals.

Further, the lighting systems and/or light sources described above may be manufactured and/or adapted such that they do not emit or emit a substantially reduced amount of the wavelength ranges of light (e.g., short wavelength blue light) that may have disruptive effects on the circadian system, while still emitting a combination of wavelengths that may provide good color rendering for various reasons, such as safety and aesthetics.

Some embodiments described within the specification provide an approach to lighting systems that challenges the conventionally-assumed relationship between CCT and spectral content of a light source, in that there is no longer a necessary relationship between the CCT of a light or its illumination intensity, and the relative amount of short or long wavelength light emitted by that light.

Figure 5:
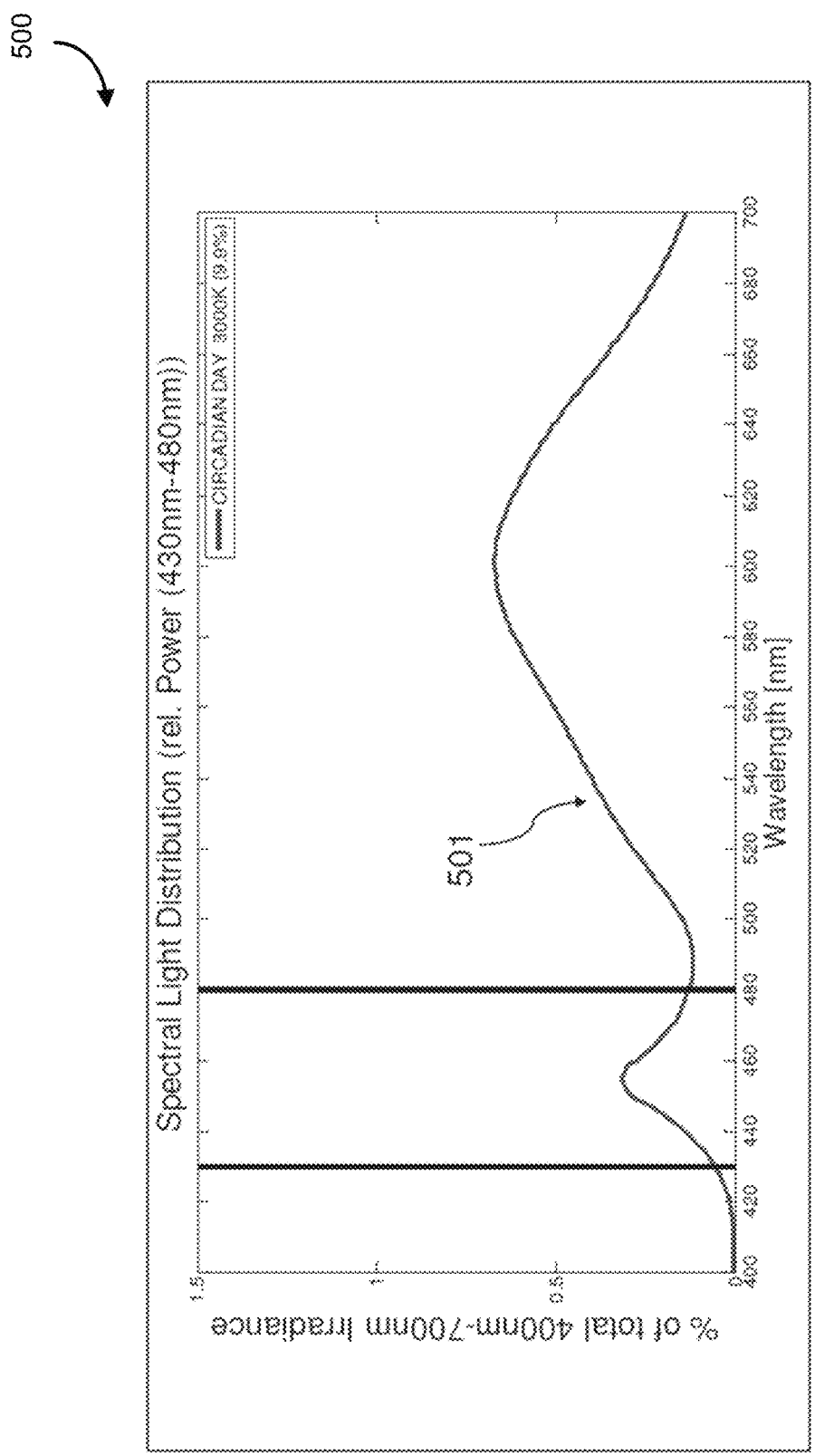
FIG. 5 is a chart depicting a normalized irradiance for wavelengths in the visual wavelength range (400 nm-700 nm) for a commercially available LED lighting source which could be adapted as or configured for operation as a day light source because it has 9.9% of the irradiance in the 430-480 nm wavelength band and would have entraining effects on the circadian system when provided during daytime hours and would promote alertness and improved performance, but because of this level of irradiance in the 430-480 nm wavelength band would be harmful or inappropriate for use during nocturnal hours.

FIG. 5 is a chart 500 depicting a normalized irradiance for wavelengths in the visual wavelength range (400 nm-700 nm) for a commercially available LED lighting source (#206 in FIG. 2) which could be adapted as or configured for operation as a day light source because it has 9.9% of the irradiance in the 430-480 nm wavelength band and would have entraining effects on the circadian system when provided during daytime hours and would promote alertness and improved performance, but because of this level of irradiance in the 430-480 nm wavelength band would be harmful or inappropriate for use during nocturnal hours, according to some embodiments. The line 501 is illustrative of the percentage of 400-700 nm radiance at specific wavelengths between 400 and 700 nm.

Figure 6:
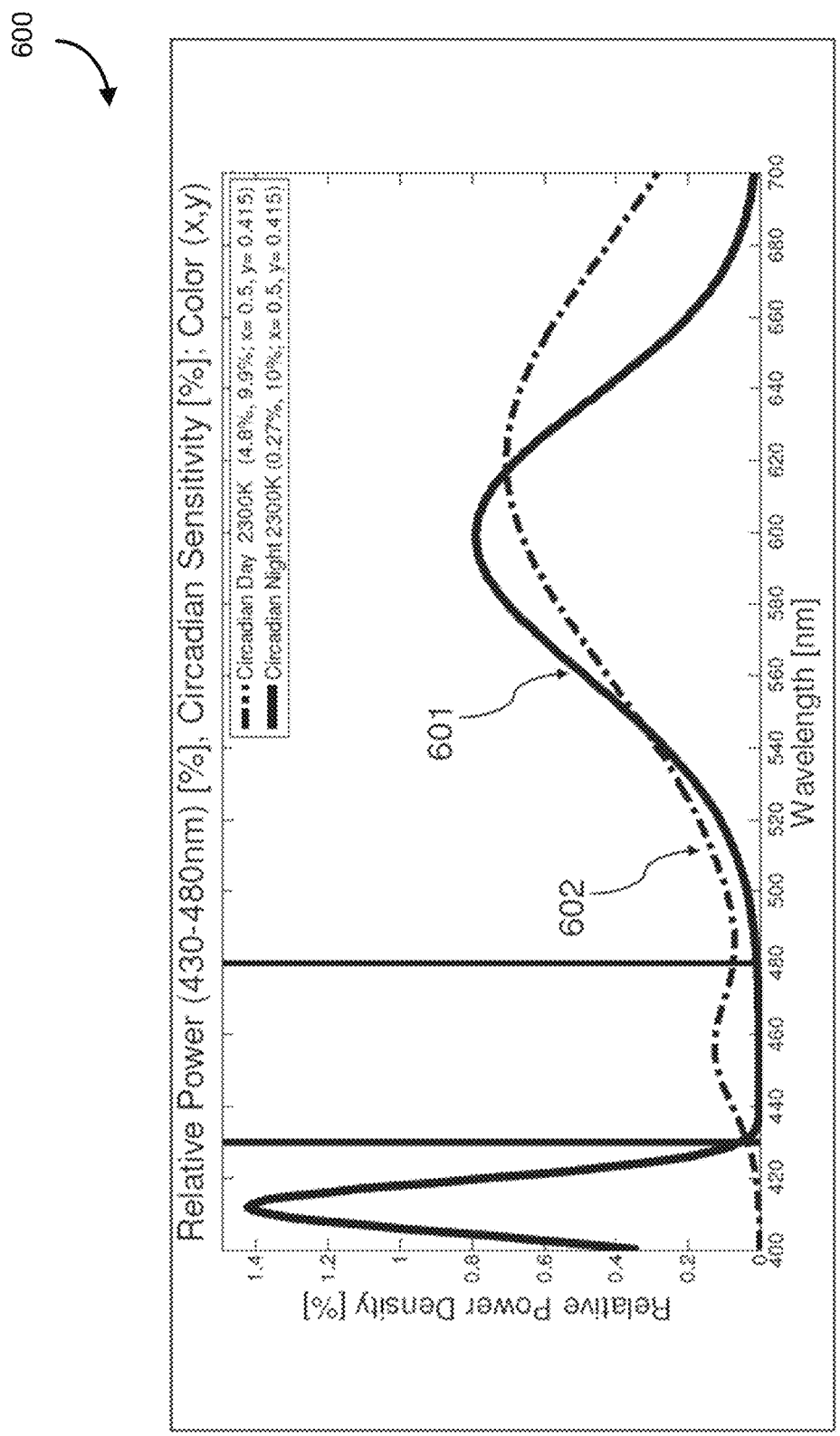
FIG. 6 is a chart depicting a normalized irradiance for wavelengths in the visual wavelength range (400 nm-700 nm) for two lighting sources, each with a CCT of 2300K, the first adapted as or configured for operation as a night light source for reduced impact on circadian states, according to some embodiments, and the second adapted or configured for operation as a day light source for stimulation of the circadian functions or entrainment of circadian rhythms.

FIG. 6 is a chart 600 depicting a normalized irradiance for wavelengths in the visual wavelength range (400 nm-700 nm) for two lighting sources, each with a CCT of 2300K, the first (601) adapted as or configured for operation as a night light source for reduced impact on circadian states, according to some embodiments, and the second (602) adapted or configured for operation as a day light source for stimulation of the circadian functions or entrainment of circadian rhythms. Note in the night light source output 601 the significant reduction of energy emitted in the 430-480 nm wavelength range, and the corresponding peak in the 400-430 nm wavelength band that compensates in order to maintain an overall white color of light provided by the lighting source.

Figure 7:
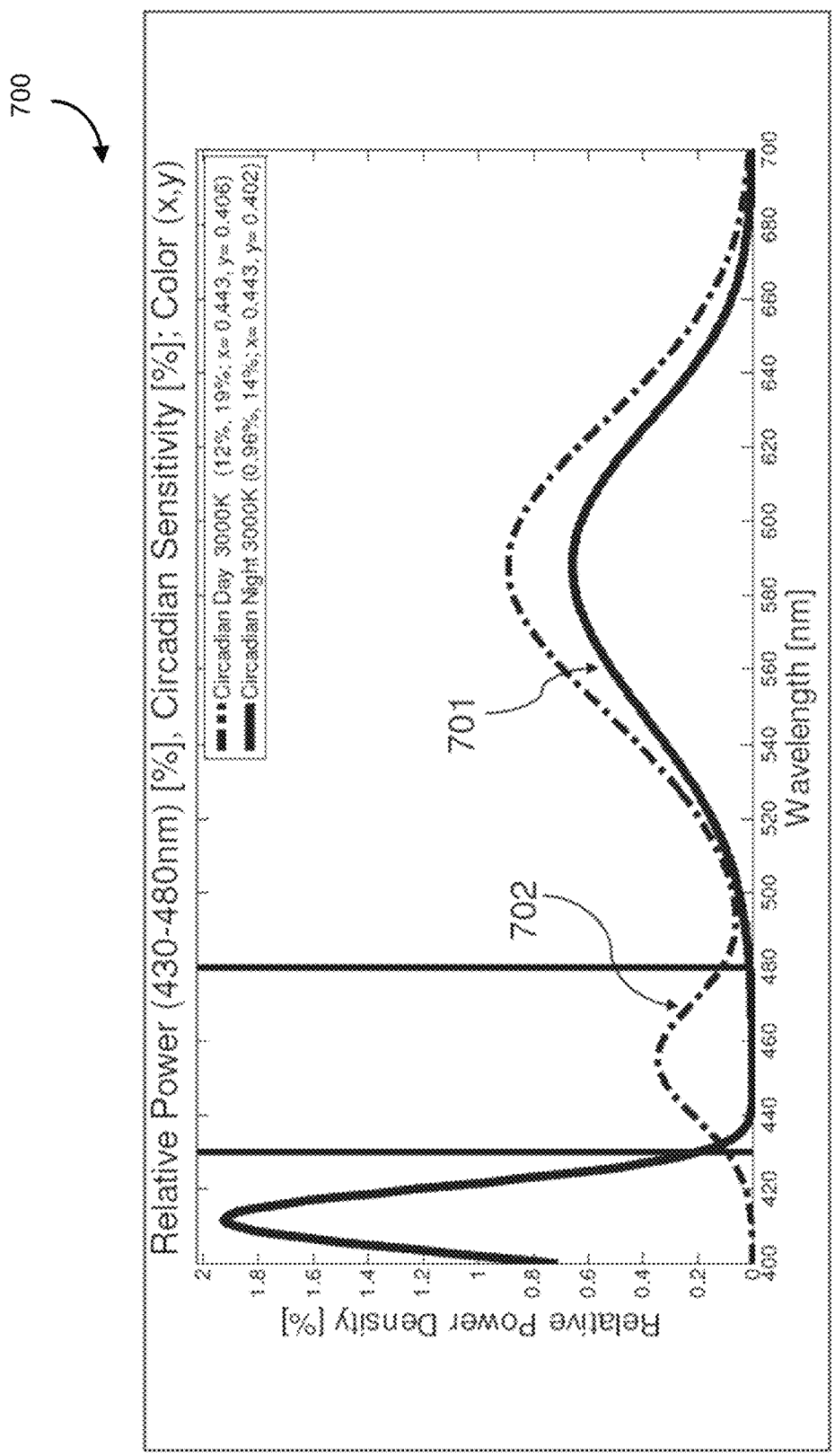
FIG. 7 is a chart depicting a normalized irradiance for wavelengths in the visual wavelength range (400 nm-700 nm) for two lighting sources, each with a CCT of 3000K, the first adapted as or configured for operation as a night light source for reduced impact on circadian states, according to some embodiments, and the second adapted or configured for operation as a day light source for stimulation of the circadian functions or entrainment of circadian rhythms.

FIG. 7 is a chart 700 depicting a normalized irradiance for wavelengths in the visual wavelength range (400 nm-700 nm) for two lighting sources, each with a CCT of 3000K, the first (701) adapted as or configured for operation as a night light source for reduced impact on circadian states, according to some embodiments, and the second (702) adapted or configured for operation as a day light source for stimulation of the circadian functions or entrainment of circadian rhythms. Note in the night light source the significant reduction of energy emitted in the 430-490 nm wavelength range, and the corresponding peak in the 400-430 nm wavelength band that compensates in order to maintain an overall white color of light provided by the lighting source.

Figure 8:
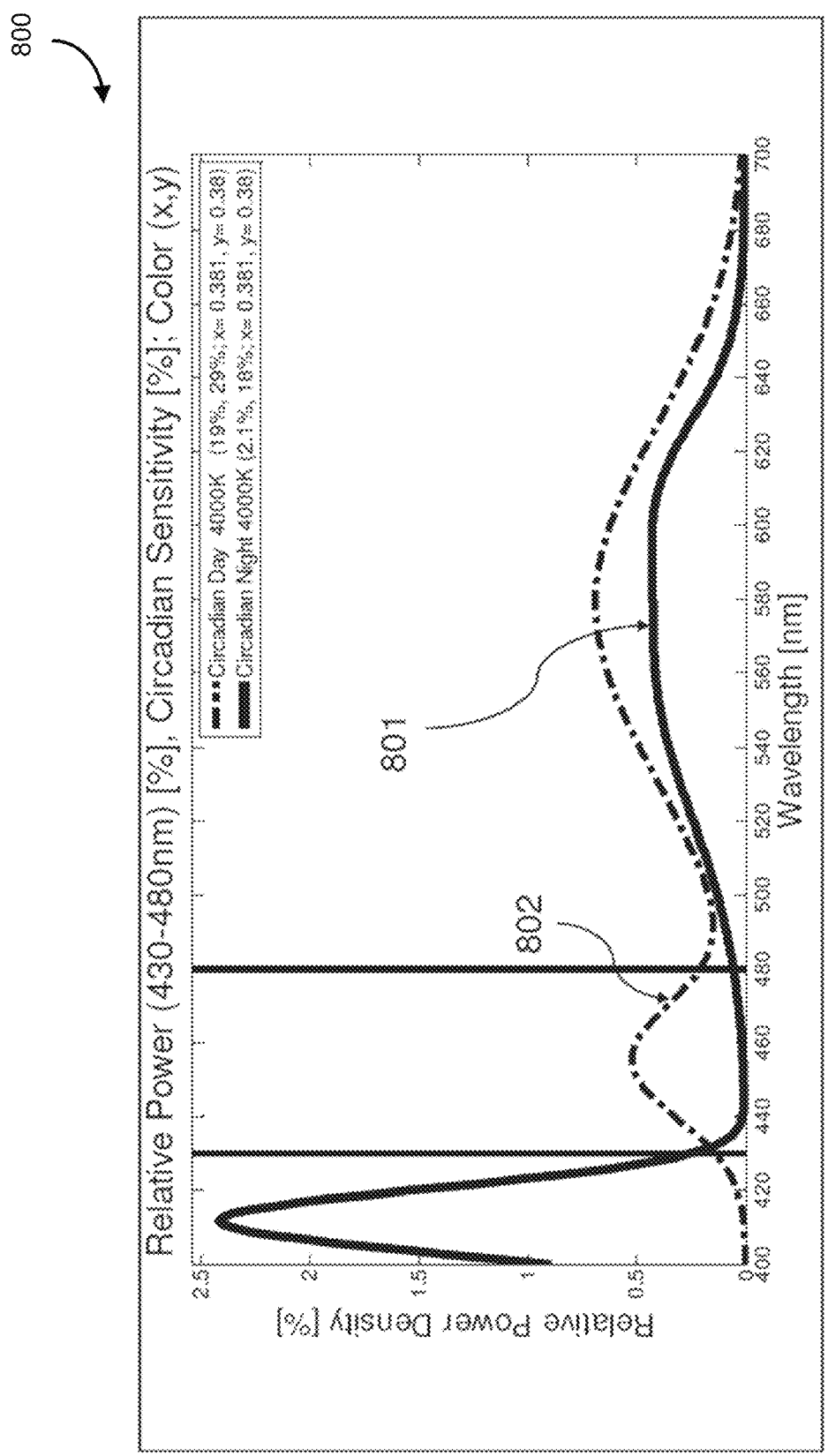
FIG. 8 is a chart depicting a normalized irradiance for wavelengths in the visual wavelength range (400 nm-700 nm) for two lighting sources, each with a CCT of 4000K, the first adapted as or configured for operation as a night light source for reduced impact on circadian states, according to some embodiments, and the second adapted or configured for operation as a day light source for stimulation of the circadian functions or entrainment of circadian rhythms.

FIG. 8 is a chart 800 depicting a normalized irradiance for wavelengths in the visual wavelength range (400 nm-700 nm) for two lighting sources, each with a CCT of 4000K, the first (801) adapted as or configured for operation as a night light source for reduced impact on circadian states, according to some embodiments, and the second (802) adapted or configured for operation as a day light source for stimulation of the circadian functions or entrainment of circadian rhythms. Note in the night light source the significant reduction of energy emitted in the 430-490 nm wavelength range, and the corresponding peak in the 400-430 nm wavelength band that compensates in order to maintain an overall white color of light provided by the lighting source.

Figure 9:
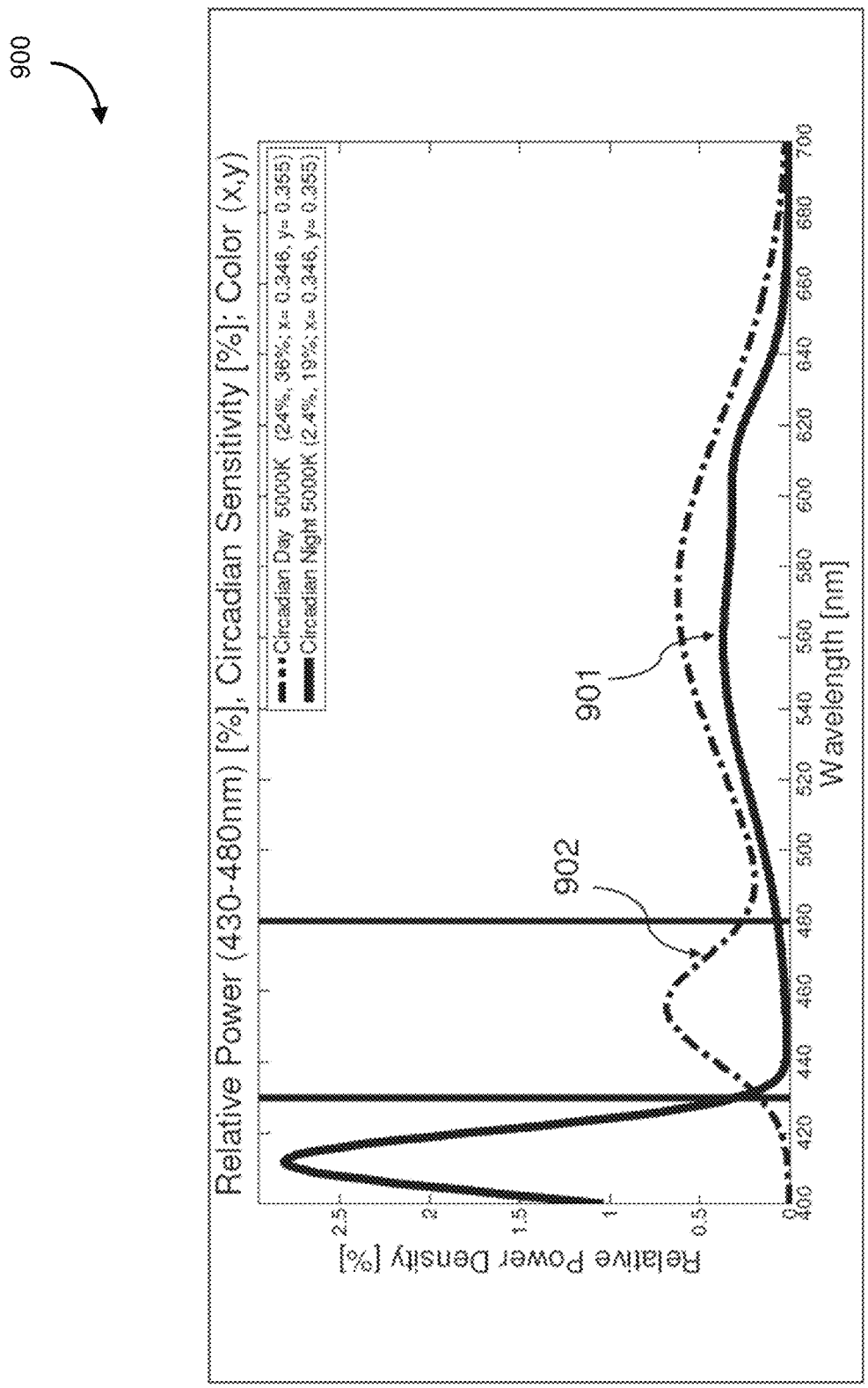
FIG. 9 is a chart depicting a normalized irradiance for wavelengths in the visual wavelength range (400 nm-700 nm) for two lighting sources, each with a CCT of 5,000K, the first adapted as or configured for operation as a night light source for reduced impact on circadian states, according to some embodiments, and the second adapted or configured for operation as a day light source for stimulation of the circadian functions or entrainment of circadian rhythms.

FIG. 9 is a chart 900 depicting a normalized irradiance for wavelengths in the visual wavelength range (400 nm-700 nm) for two lighting sources, each with a CCT of 5,000K, the first (901) adapted as or configured for operation as a night light source for reduced impact on circadian states, according to some embodiments, and the second (902) adapted or configured for operation as a day light source for stimulation of the circadian functions or entrainment of circadian rhythms. Note in the night light source the significant reduction of energy emitted in the 430-490 nm wavelength range, and the corresponding peak in the 400-

430 nm wavelength band that compensates in order to maintain an overall white color of light provided by the lighting source.

Figure 10:
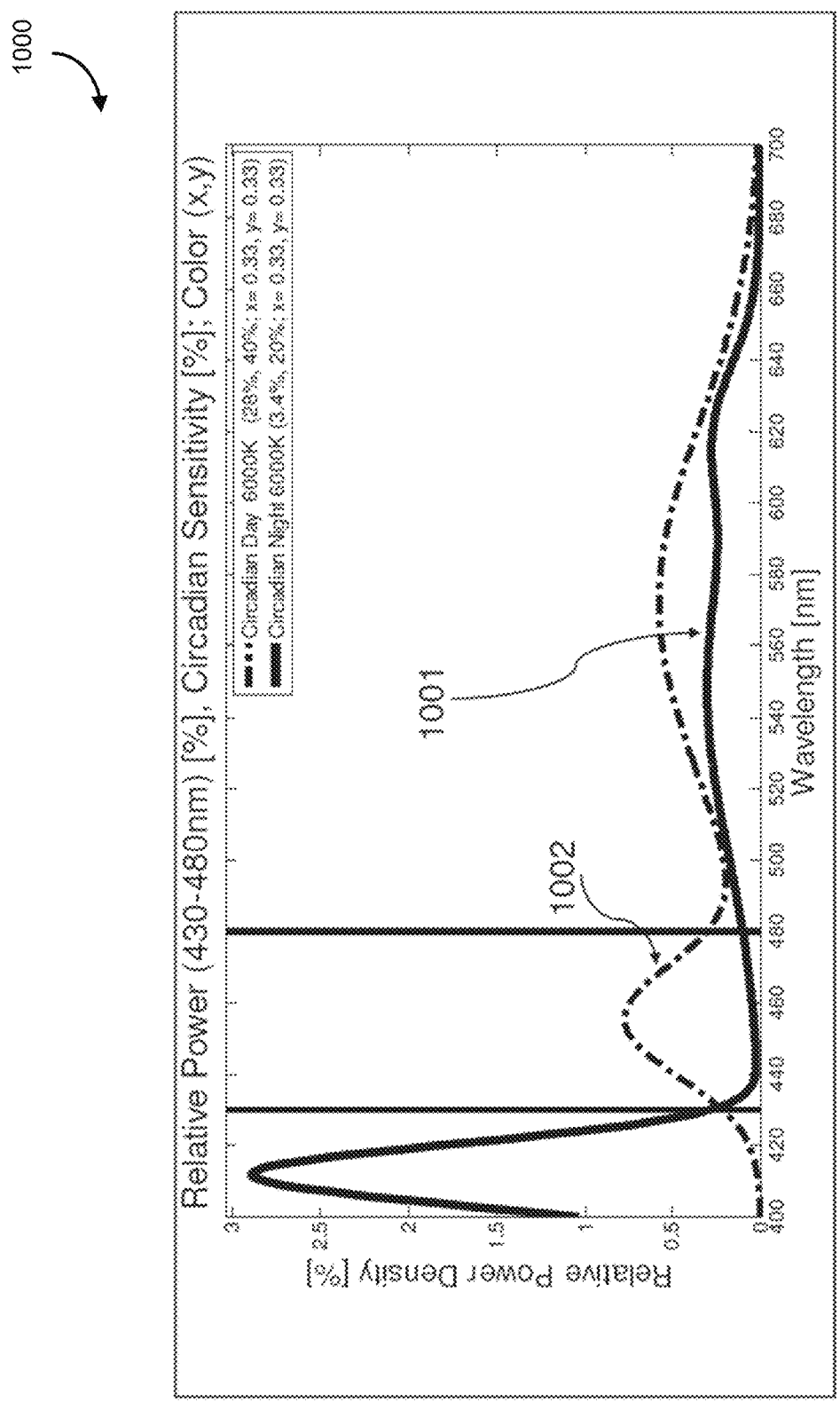
FIG. 10 is a chart depicting a normalized irradiance for wavelengths in the visual wavelength range (400 nm-700 nm) for two lighting sources, each with a CCT of 6000K, the first adapted as or configured for operation as a night light source for reduced impact on circadian states, according to some embodiments, and the second adapted or configured for operation as a day light source for stimulation of the circadian functions or entrainment of circadian rhythms.

FIG. 10 is a chart 1000 depicting a normalized irradiance for wavelengths in the visual wavelength range (400 nm-700 nm) for two lighting sources, each with a CCT of 6000K, the first (1001) adapted as or configured for operation as a night light source for reduced impact on circadian states, according to some embodiments, and the second (1002) adapted or configured for operation as a day light source for stimulation of the circadian functions or entrainment of circadian rhythms. Note in the night light source the significant reduction of energy emitted in the 430-490 nm wavelength range, and the corresponding peak in the 400-430 nm wavelength band that compensates in order to maintain an overall white color of light provided by the lighting source.

Figure 11:
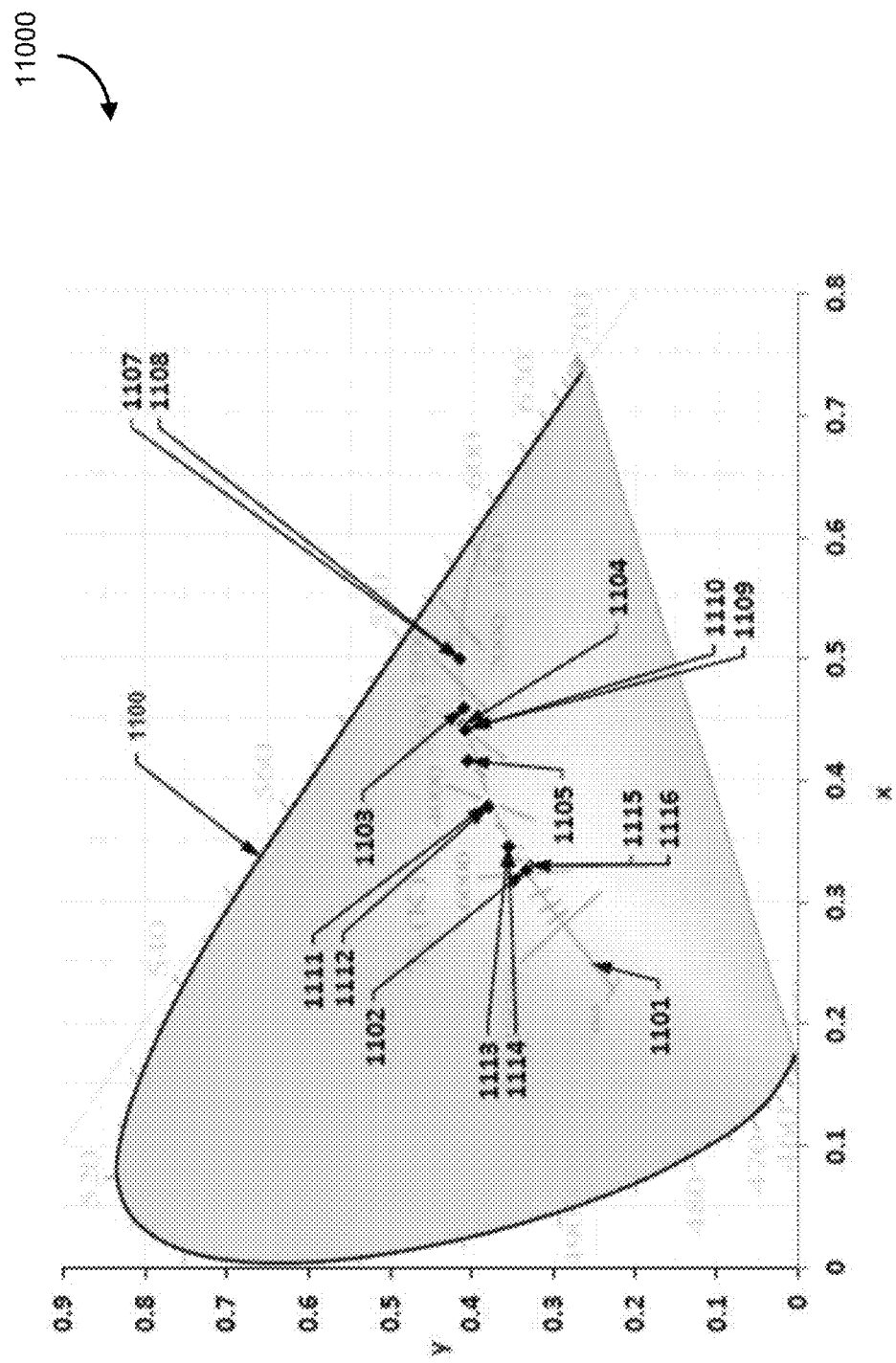
FIG. 11 is a graph depicting CIE 1931 color coordinate chart, a standard chart for depicting the perceived color of light sources.

FIG. 11 is a graph 11000 depicting CIE 1931 color coordinate chart, a standard chart for depicting the perceived color of light sources. Shown on the chart is a line representing the CIE 1931 color coordinate system boundary 1100, a line representing the black body radiator 1101, and diamonds representing the color coordinates of the examples of day and night lights described as embodiments. The graph shows the relative irradiance between 430-480 nm for a Cree™ 4Flow 2700K lamp 1103; a Philips™ Slim Style Dimmable Soft White 2700K lamp 1104; a Philips™ Par30 Bright White 3000K lamp 1105; and a GE™ Lumination Luminaire 3000K lamp 1106. Also plotted are a 2300K Day lamp 1107; a 2300K Night lamp 1108; a 3000K Day lamp 1109; a 3000K Night lamp 1110; a 4000K Day lamp 1111; a 4000K Night lamp 1112; a 5000K Day lamp 1113; a 5000K Night lamp 1114; a 6000K Day lamp 1115; and a 6000K Night lamp 1116.

FIG. 12 is a chart 1200 providing sample values that may be used for the spectral power distribution of various lights, according to some embodiments. As indicated, all of the lights provided in the sample chart have a matched CCT values (e.g., 2300, 2500, 3000).

As indicated in FIG. 12, there may be a variety of different configurations of lighting available at different CCT values. In some embodiments, lighting may be provided having CCT values from 2000-6500K.

In some embodiments, lighting configured for night usage may have approximately 15-60% of visible power in the approximately 400-430 nm range, approximately 0-5% in the approximately 430-490 nm range, and approximately 40-75% in the 490-700 nm range.

In some embodiments, lighting configured for day usage may have approximately 0-10% of visible power in the approximately 400-430 nm range, approximately 5-30% in the approximately 430-490 nm range, and approximately 70-95% in the 490-700 nm range.

Example Methods for Providing a Lighting System or a Series of Lighting Devices for Circadian Causing or Mitigating Circadian Effects The following section describes some example methods for designing, configuring, adapting, manufacturing and/or selecting components in providing a lighting system or a series of lighting devices, according to some embodiments. Other methods may be contemplated, provided, or variations of the methods below may be provided.

First, a desired CCT and light intensity may be specified (e.g., 3000K, 500 lux). Optionally, a desired CRI may be specified (e.g., a CRI of >80). In some embodiments, ranges of desired CCT, light intensity and/or CRI may be identified. For example, the ranges may be determined so that an individual with average visual acuity may be unable to distinguish between light emitted from two or more different lighting sources.

Second, a light source may be provided/selected having wavelengths in a range (e.g., blue wavelengths in the 430 nm-490 nm range) attenuated below a particular threshold. The attenuation of the wavelengths may, for example, be important for the protection of circadian function and/or melatonin secretion. The threshold may be identified, for example, at 3% of total spectral power distribution in the visible light wavelengths, 1% or 0.1% of the total spectral power distribution. In some embodiments, the wavelengths for attenuation identified are in the blue wavelength ranges, and in some embodiments, the wavelengths identified for attenuation are in the green wavelength ranges, or both blue and green wavelength ranges).

Third, the amount of compensation required in the 400-430 nm wavelengths may be identified. With higher CCT, more compensation may be required than for lower CCT lights. For example, for 6000K day lights approximately 55% of the irradiance falls between 400-430 nm, for 5000K, approximately 54% of the irradiance falls between 400-430 nm for 4000K, approximately 47% of the irradiance falls between 400 nm-430 nm, for 3000K, approximately 37% of the irradiance falls between 400-430 nm for 2300K, approximately 24% of the irradiance falls between 400-430 nm.

Compensation may be required, for example, to cause the light source to emit a particular color of light (e.g., white or substantially white) having the desired characteristics as identified in step 1. In some embodiments, compensation may be provided by a violet light emitting source. Substantially white, for example, may be established using distance to a Planckian locus, CCT, a minimum/maximum Duv and/or under various specifications (e.g., +/−0.0001-0.01), such as ANSI specifications. Duv, for example, may be indicative of variations perpendicular to the black-body curve. At least one, at least two, or at least three, at least four, or all of these characteristics may be provided in various embodiments.

Figure 13:
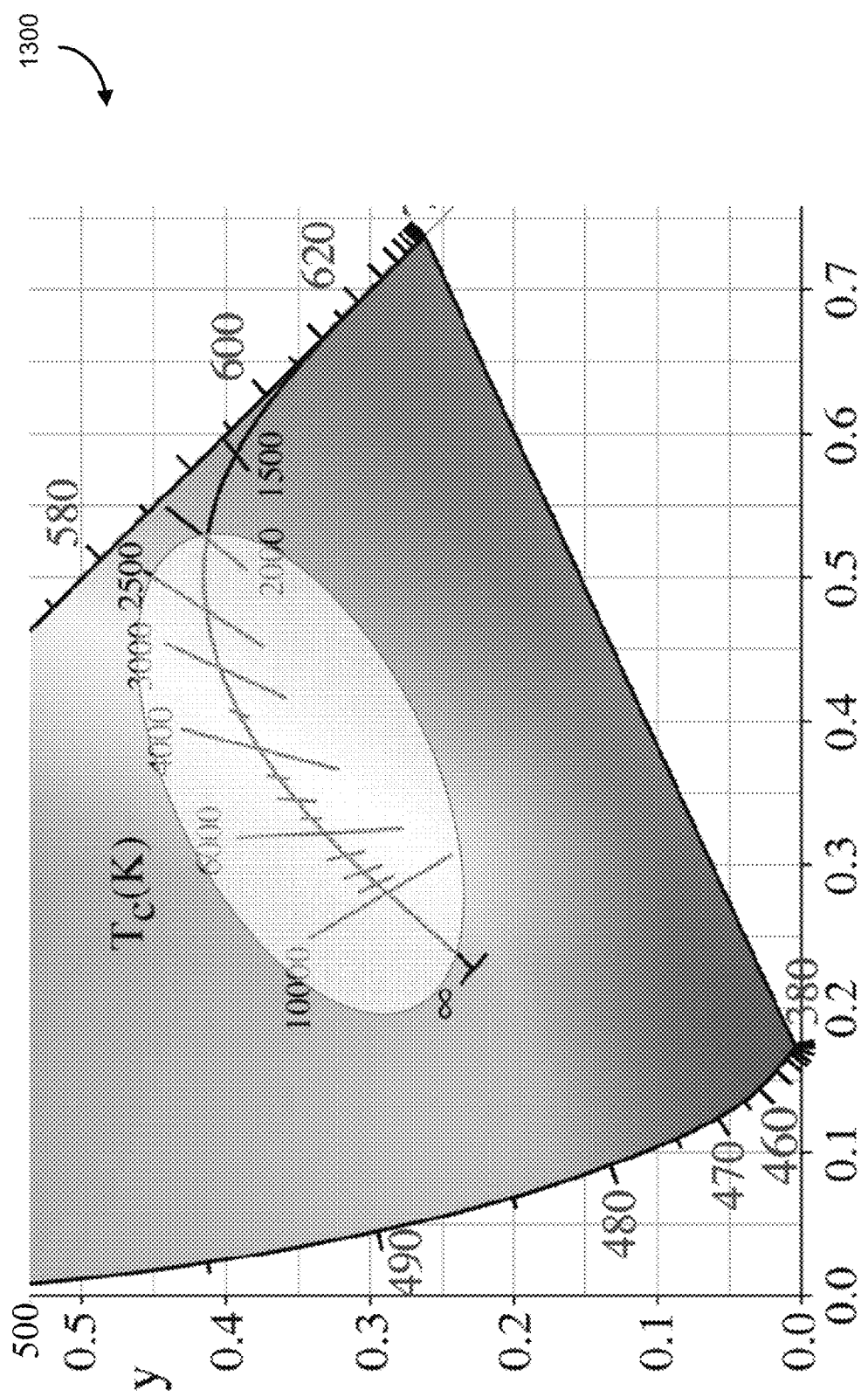
FIG. 13 is an annotated 1931 CIE chart having a white oval indicating a preferred bound of points where white or nearly white light may be provided, according to some embodiments.

White or near-white, in some embodiments, may be defined as any point within the oval as provided in FIG. 13.

FIG. 13 is an annotated 1931 CIE chart 1300 having a white oval indicating a preferred bound of points where white or nearly white light may be provided, according to some embodiments. As indicated in FIG. 13, the area is between approximate X coordinates of 0.18-0.54, and approximate Y coordinates of 0.23-0.48. This may be the boundaries where an individual may perceive that light is "white" or near "white".

Fourth, a matching complementary light source may be identified having a differing spectral power distribution in the 430-490 nm range (e.g., a day-configured light having 10% of the visible power distributed in the 430-490 nm range). The matching complementary light source may also have the same or similar (e.g., within an identified or visually indistinguishable range) characteristics as identified in step 1. In some embodiments, the matching complementary light source may be configured for the causing of circadian effects, such as a day light configured for entraining a circadian system and/or to supress melatonin expression/secretion.

Fifth, the light source and the matching complementary light source may be controlled and/or operated together such that a lighting system may be provided that is able to protect, engage, and/or entrain circadian rhythms of one or more individuals exposed to light emitted from the lighting system. In some embodiments, the light sources may be alternatively turned on and off (e.g., either a night-configured light is on, or a day-configured light is on), or the relative proportion of light provided by each of the light sources may be varied (e.g., from 100:0-0:100 and various proportions in between).

Sixth, the lighting system may be configured for and/or programmed such that a specific cycle of operation between the light sources may be implemented. For example, the lighting system may be configured based on a timing cycle, a shift work cycle, designed to entrain individuals having irregular circadian rhythms, etc.

Seventh, the lighting system may be accompanied by a controlling system comprised of computing devices and automated switching mechanism, such that the computing device would execute various programs, which programs would then control the switching mechanisms, such that the lights comprising the lighting system would be turned on, off, or any condition in between, in order to control and attenuate the circadian impact of the lights on an individual illuminated by those lights.

Eight, various circadian effects that might be produced by the controlling system would include: Circadian Phase Advance, which would advance the timing of the individual's circadian system relative to the natural day; Circadian Phase Delay, which would delay the timing of the individual's circadian system relative to the natural day; and Circadian Entrainment, which would entrain the individual's circadian system to the natural day. These various effects are all achieved through the controlled activation of the appropriate lighting condition at the appropriate time, i.e. providing a light source without attenuated light in the 430-490 nm range during the advance phase of an individual's Phase Response Curve (PRC), and a light source with attenuated light in the 430-490 nm range during other phases of an individual's PRC if circadian advance is desired; providing a light source without attenuated light in the 430-490 nm range during the delay phase of an individual's PRC), and a light source with attenuated light in the 430-490 nm range during other phases of an individual's PRC if circadian delay is desired; and providing a light source without attenuated light in the 430-490 nm range during the early part of the advance phase and the early part of the delay phase of an individual's PRC, and a light source with attenuated light in the 430-490 nm range during other phases of an individual's PRC if maintenance of entrainment to the individual's current circadian timing is desired.

Environmental Lighting Control

Some embodiments described relate to devices and systems for detecting the presence of individuals who are in the vicinity of light sources, and utilizing information about the work-rest schedule and/or circadian sleep-wake cycle of those individuals to adapt the spectral power distribution of the light emitted from the light sources by time of day so as to regulate and synchronize each individual's human circadian timing system and protect them against the harmful effects of specific spectral wavelengths at night.

These systems may, for example, receive various aspects of information indicative of a circadian state of individuals from various data sources. This information may be used to assign a circadian state to the individual based on the received electronic information, extrapolate future circadian states based on the assigned circadian state, and to update a profile corresponding to the individual with the assigned circadian state and the extrapolated future circadian states. Where there is no information or incomplete information, time of day information may be used as a default (e.g., in a particular time zone, the evening is set to 9:00 PM, the night at midnight, based on local time settings).

The profile of the individual may track the profile's circadian states, and control lighting accordingly to effect circadian outcomes (e.g., protection of a circadian rhythm, entrainment of a circadian rhythm in anticipation of travel or changed work schedule), etc.

Such systems may further utilize external information to extrapolate and determine information indirectly through estimations. For example, a system may be able to connect and/or interact with wireless information stored on wireless access points that track wireless signals associated with mobile devices of individuals. These signals may be used, for example, to triangulate the positions of the individuals as they move around an environment, and various lighting sources that are in proximity or provide light incident to the individuals. For example, as the individual moves around into various rooms, the light sources may be controlled in accordance with the individual's circadian state (e.g., day state, night state, evening state) and the individual's progress into a circadian state (e.g., if an individual is 4-5 hours into the night state and transitioning to the day state) so that the individual's circadian rhythm is not disrupted.

The systems may be provided for a single light source or more than one light source, in an environment with a single region or multiple regions, for an individual or for more than one individuals. Control logic and circuitry is used to modify the operation and/or transform various operating characteristics based on tracked circadian states (e.g., as provided in user profiles stored on a database). Light sources may include various different types of lights. For example, controlled light sources may be LED light sources, lasers, incandescent lights, fluorescent lights, halogen lights, and quantum dots, among others. The light sources may have different dispersion properties, CCT, spectral distribution, CRI, and may have different controllable features. For example, some lights may be controllable to turn on and off only, other lights may be controllable for dimming, some lights may have movable and/or otherwise adjustable filters that modify spectral distribution of light emitted, etc. In some embodiments, lights may be movable (e.g., along a track or a guide), rotatable (e.g., to change orientation), etc.

An individual may be exposed to light from a number of different lighting sources as the individual interacts and/or moves within an environment. The combined exposure from one or more light sources may need to be controlled and/or otherwise adapted in relation to the circadian needs of the individual. The individual may not always be moving around within the environment. For example, the individual may be immobile, and light sources may be moved in relation to the individual depending on the individual's circadian needs and/or desired impacts on the individual's circadian functioning.

There may also be more than one individual in a particular section of an environment at a given time, and there may be a need to coordinate the lighting in a manner that balances the needs of a group of individuals. In some embodiments, compromises may need to be made where the needs differ between individuals. For example, the individuals may not have the same current or desired circadian states. In these situations, the control system may need to cater to the individual whose circadian-protective needs are the greatest. For example, in a hypothetical situation where there is are three individuals, one in a biological late night state, one in a biological day state, and one in a biological early night (e.g., evening) state, all three of the individuals have differing circadian protective requirements. However, the system may identify that based on determinations from their respective electronic profiles, the biological early night individual will require the greatest level of attenuation. In this situation, the system may control the lighting provided to the individuals so that all three of the individuals are provided with light that is significantly attenuated in both green and blue wavelength ranges, despite such protection not necessarily being required for two of the individuals. These situations may be provided for through logical circuitry (e.g., physical logic gates on a chip implementing a maximum or minimum attenuation control logic) or software (e.g., an encoder that utilizes software based logical rules when encoding specific machine-readable commands for transmission to control the light sources). A combination of hardware and software controllers may also be utilized.

In some embodiments, the circadian control system may be provided in the form of an integrated circuit or a chip that may be plugged into a light controller. Such an integrated circuit or chip design may contain electronic circuitry to receive and process information through logical gates and to transform and/or encode control signals accordingly. For example, a number of pins of the integrated circuit or chip may be used for data receipt, a number of pins for power transmission, and the integrated circuit or chip may process the data to provide control outputs through a set of output pins. In such an implementation, the integrated circuit or chip may be sold as a standalone unit to be used in conjunction with the one or more lights and/or a controller that may track and/or transmit control commands to the lights. For example, a circadian control integrated circuit or chip may be plugged into the lighting controls of a vehicle (e.g., airplane, train, car), a facility (e.g., a stadium, an office, a warehouse, a factory), among others.

Light sources may, for example, include various devices that emit light within a given space, including, for example, ceiling luminaires which may be, for example, troffers and/or downlights, desk lamps, focused work area lighting, computer screens, television screens, indicator lights, electronic tablet and/or mobile phone screens.

Light may be provided using various technologies, such as light emitting diodes (LEDs), incandescent lights, neon lights, fluorescent lights, tungsten lights, high intensity discharge (HIDs) lights, etc. The lighting sources and/or lights may have various characteristics, such as spread, spectral power distribution, light intensity, correlated color temperature (CCT), color rendering index (CRI), etc.

The light sources may be controlled and/or operated through various components and/or systems that may range from fully automated digital systems to analog systems controlling the light sources through the control of power provided to the light sources. In some embodiments, the lights sources may be controlled through the use of one or more control systems, which may send instructions and/or other command signals to the light sources. The one or more control systems may be implemented using, for example, computing devices having non-transitory computer readable media and/or various data interfaces. The one or more control systems may include servers, and may be implemented on various technologies and platforms.

In some embodiments, the control system may be configured to receive information associated with one or more individuals, and configured to control/operate the light sources in view of the circadian functioning of the one or more individuals.

In particular, some embodiments may include one or more systems configured to receive information related to individuals exposed to or potentially exposed to light from one or more controlled light sources. The systems may be configured to utilize various elements of information, such as presence/position information, schedule information, etc., to control various characteristics (e.g., spectral power distribution, light intensity, CCT, CRI, Duv, color spectrum and timing) of light emitted by environmental lighting systems and light-emitting devices to address the circadian needs of the individuals being illuminated.

The control elements may, for example, control the application of structural, chemical and/or mechanical features associated with the lighting elements. In some embodiments, lights may have filters applied, filters modified (e.g., electro chromatic filters), phosphors activated, lights switched on/off, dimmed, moved (e.g., along a track so that, for example, the light is above or below an eye level), rotated (e.g., changing orientation and/or angle), different illuminating elements within a light turned on/off, colors modified, CCTs modified, light intensity modified), etc.

The presence detection systems may be deployed with lighting systems which provide light (e.g., white, or near-white light) at a constant, near-constant, visually indistinguishable or comparable color temperature and illumination intensity at various hours of day and night while varying the spectral power distribution of the light emitted. The presence detection systems may include various biometric recognition (for example, facial recognition).

The spectral power distribution of light may be varied based at least one of the presence, location and/or characteristics of an individual. The presence, location and/or characteristics may be determined through the use of wearable devices, biometric information (e.g., facial recognition), security system logs, and expected schedules.

For example, the control system may be configured to interoperate with a health records database, for example, in the context of a hospital, a care facility, a hospice, a rehabilitation centre, a sleep clinic, among others. The electronic health records of various individuals may be posted to their profiles and may potentially have information related to the circadian schedules of the individuals, the light exposure records of the individuals, or information from which such schedules and circadian probative information may be gleaned, estimated, and/or extracted. For example, for a given individual having an electronic health record indicative of issues with or related to circadian processing, such as insomnia, micro-sleeps, etc., or a profession related to circadian rhythm issues, the control system may be adapted to receive this information and process it to extract circadian related information. Circadian related information may be estimated from addresses, work schedules, occupations, health logs, etc., if not explicitly provided. In some embodiments, circadian state information may also be obtained indirectly through biological or biochemical sampling (e.g., composition of tears, sweat).

This circadian related information may be transformed and/or otherwise processed to determine an exposure schedule prescribed for the individual, which may be associated with the current circadian state of an individual or a desired circadian state.

In some embodiments, databases storing other types of information, such as historical time, and/or attendance data and past work/rest periods records may be accessed or used to determine a timing sequence and/or a schedule in which the operation of the lights may be controlled. In some embodiments, self-reported logs may be utilized.

Further, the system may be configured to associate different weightings to different elements of data, for example, providing more relevance to data that was collected more recently, less relevance to outdated data, weighting data from different sources differently (e.g., due to relevance, reliability), etc. For example, in one embodiment, the period of the data may not restricted by time. In some embodiments, the period of time may be a week, biweekly, a month, any interval there between or any other suitable period, etc.

The system may be configured to generate, modify maintain and/or apply one or more logical rules governing how data is processed and/or weighted, how characteristics of lighting elements may be controlled, how one or more characteristics associated with one or more individuals' circadian rhythms are generated/updated/maintained, etc.

For example, there may be logical rules that govern that data from a work schedule may be more relevant than self-reported data. There further may be logical rules that determine that in accordance with a particular circadian rhythm, how lighting sources should be operated and/or controlled. These rules may be configured to take into consideration the number of individuals in an area, the prioritization between data elements, the prioritization of the needs of individuals in an area if the light from the lighting systems affecting the area may affect more than one individual at a time.

The system may be configured for the determination of various characteristics associated with the circadian processes/rhythms/states of various individuals who are or may be exposed to light from any of the lighting sources. For example, the particular circadian rhythm of one or more individuals may be mapped to one or more states, and in some embodiments, a schedule may be generated for one or more individuals that may indicate, for example, their preferred, target and/or optimal circadian state at particular periods of time.

The system may be configured to use information provided regarding the preferred, target and/or optimal circadian state of one or more individuals in determining and/or controlling how the light provided by the various lighting sources should vary in the presence of the one or more individuals. A schedule may be determined, for example, for generating a schedule of an individual's exposure to light having particular characteristics (e.g., blue/green wavelength enriched and/or depleted lights).

In accordance with the schedule, the light may be controlled, for example, by modifying the spectral power distribution, the CCT, the CRI, the light intensity, the on-off state of the lights, the proportion of light provided by one or more light sources relative to other light sources in a lighting system, etc.

Overall lighting characteristics of the lights for control may include, for example, at least (i) a spectral power distribution in human-visible wavelengths, (ii) a correlated color temperature, and (iii) a color rendering index score, (iv) a Planckian curve offset, and (v) a Duv. One, two, three, four, or all of the above characteristics may be controlled for.

In some embodiments, the light is controlled such that the spectral power distribution may be varied in one or more target wavelength ranges (e.g., blue and/or green light wavelength ranges where disruptive circadian effects may potentially result when individuals are exposed to light having spectral power in those wavelength ranges above a particular threshold power). Accordingly, in some embodiments, one or more light sources may have characteristics configured for the promotion of various circadian outcomes.

The spectral power distribution of power in the wavelength ranges may be increased (e.g., for a blue and/or green 'enriched' light source), attenuated (e.g., for a blue and/or green 'depleted' light source), etc.

The particular wavelength ranges may, for example, be wavelengths from about 430 nm to 480 nm, 430 nm-490 nm, 415 nm to 495 nm, 435 nm to 475 nm, and various other suitable wavelength ranges of blue light.

In some embodiments, the particular wavelength ranges may be associated with green light, such as in a range between 520 nm to 560 nm, 520 nm to 570 nm, 510 nm to 560 nm.

The wavelength ranges provided above are examples and any ranges in between and other ranges may also be used, in some embodiments.

A blue 'enriched' light source may be useful for causing circadian effects on an individual exposed to light from the source, such as to entrain the individual's circadian rhythm during a circadian day time period. In some embodiments, a green 'enriched' light source may be used.

A blue 'depleted' light source may be useful for avoiding and/or reducing potential circadian effects on an individual exposed to light from the source. Such a source may be used to protect and/or maintain circadian functioning of an individual, who may, for example, be exposed to light from the blue 'depleted' light source during a circadian night time period.

In some embodiments, light may also be 'green' depleted, and/or both 'blue and green' depleted. The aspects of a light may be controlled to obtain the depletion, or in the case where there are multiple lights, a combination of operating (e.g., including, for example, changing the relative intensities and/or ratios of contribution) the various lights may be used to obtain the depletion. In some embodiments, some lights may simply be switched off and only lights having the depletion may be used during periods in which depletion is desired.

Not all the lights have to be controllable in the same ways. In some embodiments, as the lights register with a control system, each of the lights may be associated with a profile that tracks the controllability of the light, as well as specific light output parameters that are associated with the light as it is controlled. For example, these light output parameters may include a spectral distribution, directionality, coherence (e.g., spread lighting, specific lighting), etc. These light output parameters may also be dependent and/or variable depending on environmental factors, such as temperature (e.g., the output of some LEDs may be affected in the heat or the cold), humidity, etc.

As described above, the depletion of 'green' wavelength ranges may be beneficial during an evening (e.g., an early night state) period, but then as the effect may be transient, such depletion may not be necessary later in the night (e.g., a late night state). In some embodiments, the early night state may be considered the 'evening' (e.g., a few hours before or after a typical night onset of sleep), and the 'late night state' may be considered the 'night' (e.g., following the evening period). For example, if an individual has a night onset of sleep period typically at 10 PM, the system may control the lights and their emitted incident light on the individual such that the individual is not exposed to both blue and green light from 7 PM-1 AM, and then only avoiding exposure to blue light from 1 AM-9 AM. Other times and variations may be possible.

In implementation, a control system may be provided that is configured to control three sets of light sources independently, for example, (1) blue and green depleted light sources (low/attenuated emission in the about 430-560 nm wavelength range), (2) blue-only depleted light sources (low/attenuated emission in the about 430-490 nm wavelength range) and (3) blue-rich light sources. In some embodiments, there may only be the first and second sets of light sources. For example, from 7 AM to 8 PM, the provided light may be blue rich. From 8 PM to 2 AM, the light would be blue & green depleted. From 2 AM-7 AM, the light would be blue only depleted. Attenuation, for example, may be, in accordance with some embodiments, may be selected from the group of percentages consisting of 3%, 1%, 0.5% and 0.1%. Attenuation, for example, may include using filters and/or otherwise controlling the light output (e.g., by switching lights on/off, dimming lights, activating various phosphors) to reduce the light in specific wavelength ranges. While some wavelength ranges are attenuated, others may be allowed to have various levels of transmission. Further, some wavelength ranges may further be augmented through the use of mechanisms such as violet light emitting sources.

In some embodiments, the sets of light sources may be segmented in various ways, for example, based on physical location, height, a weighted impact score on an individual's eyes, the controllability of the light sources, etc., and specific sets of light sources may be controlled differently to complementarily or in combination provide a specific light outcome.

The specific properties (or profiles) of transmission, attenuation, and augmentation may be provided in relation to a color correction element that is configured to ensure that the aggregate incident lighting provided by the one or more light sources has overall lighting characteristics within a pre-determined comparable range relative to the aggregate incident lighting provided by the one or more light sources when the one or more light sources are activated but not controlled to have circadian-significant attenuation along the circadian active wavelength range.

Such color correction and control may be utilized to help solve various technical problems associated with the attenuation of light in particular wavelengths, for example, including, but not limited to, issues related to color (e.g., attenuation may cause off-color effects), a lack of CCT, a lack of CRI (e.g., which may cause difficulties in workplaces where color discrimination is important for work requiring a level of dexterity), among others.

Further, the color correction element may help ensure that when lighting conditions are changed as a result of varied control of the light sources (e.g., to effect various circadian outcomes), the lighting does not appear to significantly change (e.g., perceivably change) to an individual who is exposed to the lights as they change. Such changes may, for example, prove distracting in a workplace and may be undesirable, especially in workplaces where intense levels of concentration are required).

The specific timing may be varied according to a circadian schedule developed for the individual. The circadian schedule may not necessarily need to be timed to the individual's current circadian state. For example, the system may be configured to extract (e.g., from calendar information) and/or otherwise ascertain what the individual's desired circadian state may be, and apply the schedule in the form of data processing and/or logical rules such that over a period of time, the person's schedule is slowly entrained to move towards a particular circadian schedule through the control of various sets of light sources. The timing and/or duration of the day, "evening"/early night, and "late night" periods may be modified, etc.

In some embodiments, the periods of night may be segregated to differentiate between the early night and late night so that differing levels of circadian protection may be provided during these timeframes. For example, circadian protection requirements may be differing in a biological early night (e.g., evening) as compared to a biological late night (e.g., night), and accordingly, lights may be controlled differently during these periods, attenuating different wavelengths and providing different compensation effects. These differences may provide for reduced power consumption, increased circadian protection/entrainment, or a more granular and/or tuned approach for a particular individual's circadian state.

For example, if an individual is seeking to move to a region having a different time zone, the individual may seek to pre-emptively address jet lag issues by inputting a desired circadian state into the lighting system, the lighting system analyzing and generating a schedule by comparing the desired circadian state with the current circadian state. Representative electronic information in the form of high level scheduling and/or exposure related commands may be provided to a control system, which then encodes the desired outcomes in the form of machine-readable inputs that may be provided and/or transmitted to the various light sources such that the operation of the light sources is controlled accordingly (e.g., dimmed, moved, oriented, switched on and/or off, filters being turned on, phosphors activated, different sets of lights activated).

Figure 14:
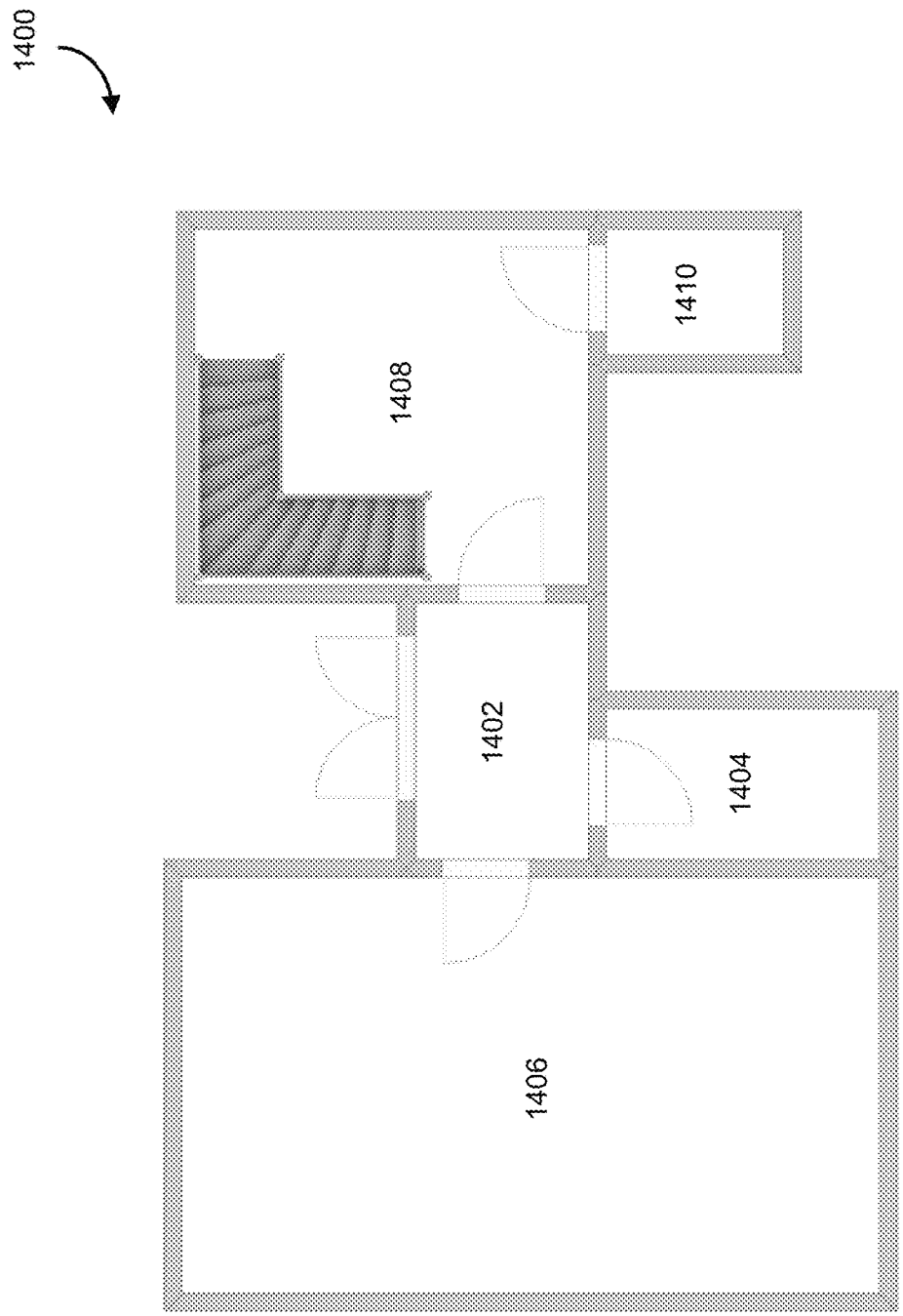
FIG. 14 is an example environment having a number of different sections (e.g., portions of rooms, rooms, hallways, multiple levels), according to some embodiments.

FIG. 14 is an example environment 1400 having a number of different sections (e.g., portions of rooms, rooms, hallways, multiple levels), according to some embodiments.

The sections may be indoor, outdoor, multi-level, etc., and the word "sections" is broadly meant to cover any area where light produced by one or more light sources is able to illuminate and potentially impact the circadian functioning of one or more individuals who may be in and/or near a section and exposed to the light. It would be apparent to someone skilled in the art that the environment may be mobile, such as a mobile home, a vehicle, etc.

There may be various rooms 1402, 1404, 1406, 1408, and 1410, the rooms including, for example, hallways, bedrooms, meeting rooms, conference rooms, and there may be various artificial and/or natural light sources that provide light into the rooms.

Each of the sections of the environment may have different lighting sources, positioned at various heights, positions, having various characteristics, including spread, directionality, spectral power distribution, light intensity, etc. The directionality of the light relative to the eyes of an individual (e.g., the angle of incidence of the light provided by the light) may be an important consideration in determining the circadian impact of light provided by the sources.

The light sources may be individual or grouped together. For example, a plurality of light sources may be combined together so that where the plurality of light sources may be operated in various complementary ways to provide illumination. For example, there may be two light sources that, in combination, form one lighting unit that may be operated in either a night-mode (e.g., with particular wavelength ranges attenuated), or in a day-mode (e.g., with a power of the particular wavelength ranges similar to conventional lights and/or the particular wavelength ranges enriched). There may also be combinations where there may be more than two light sources, such as a combination with three light sources (e.g., one for a day-mode, one for a night-mode, and one for an evening-mode). The light sources may include a combination of specifically circadian-adapted lighting and conventional lighting, which may be controlled and operated in various combinations together such that the overall aggregate incident lighting provided is adapted towards a particular circadian outcome of one or more individuals who are exposed to the light.

In some embodiments, the light sources may be controllable such that a light source may transform for use from one mode to another through the applications of components such as light light emitting sources, filters, phosphors, etc. Such transformation may be initiated through the provisioning of a specific set of machine-interpretable control commands that are adapted for activating and/or deactivating components of the light sources.

The various light sources may be controllable in relation to where they are positioned and their impact on individuals at various locations and/or positions. The light sources may also be associated with desks, walls, ceilings, floors, devices, etc. The light sources may be movable along guides, tracks, etc.

The control of the lighting provided by the light sources may, for example, be controllable to vary the spectral power distribution of the light wavelengths emitted, according to human circadian timing system requirements of those individuals who are in the proximity of the light emitted and receiving illumination delivered by one or more particular light sources. In some embodiments, the light sources may be independently controlled.

Further, the control of lighting may be used in relation to various objectives related to circadian functioning, such as protecting circadian rhythms from disruption, entraining circadian timing systems (e.g., helping promote a healthy circadian rhythm), etc. Effecting circadian functioning, for example, may include the maintenance and/or modification of circadian phase, amplitude and periodicity regulation of individuals.

For example, the lighting may be controlled to reduce and/or prevent the harmful effects of light at night, including the flattening, suppression and/or disruption of neuroendocrine functions such as melatonin.

In some embodiments, the lighting may also be controlled to provide a variation of spectral power distribution while maintaining a same, similar and/or comparable CCT and/or light intensity to another light and/or various conventional lighting sources. In some embodiments, a same, similar and/or comparable CRI may be maintained. For example, the power distribution in blue/green wavelength ranges may be actively reduced relative to the overall power in the visible light wavelength range while the CCT and light intensity provided are the same, similar and/or comparable with the light prior to variation and/or other conventional light sources. The variation of the power distribution in blue/green wavelength ranges may aid in the protection of an individual's circadian functioning or aid in the entrainment of an individual's circadian functioning.

In some embodiments, the lighting is controlled to maintain overall lighting characteristics within a pre-determined comparable range relative to the aggregate incident lighting provided by the one or more light sources when the one or more light sources are activated but not controlled to have circadian-significant attenuation along the circadian active wavelength range.

Example Embodiments—Environmental Lighting Control

In some embodiments, light sources capable of varying their spectral power distribution in one or more wavelength ranges while maintaining and/or emitting light having a fixed, comparable or visually indistinguishable color temperature (CCT) and color rendering index (CRI) may be provided having the ability to detect, through a variety of means, methods and techniques, individuals who may be exposed from the light sources, and to determine and/or set the spectral power distribution in the particular wavelength ranges (e.g., approximately 430 to approximately 490 nm spectral window) based at least in part on the circadian functioning of the individual.

Differing spectral windows may be provided. For example, circadian active wavelength ranges may include wavelengths of blue light selected from a group consisting of wavelength band ranges of: about 430 nm to about 500 nm, about 430 nm to about 490 nm, about 430 nm to about 480 nm, about 430 nm to about 470 nm, about 435 nm to about 500 nm, about 435 nm to about 490 nm, about 435 nm to about 480 nm, about 435 nm to about 470 nm, about 440 nm to about 500 nm, about 440 nm to about 490 nm, about 440 nm to about 480 nm, about 440 nm to about 470 nm, about 450 nm to about 500 nm, about 450 nm to about 490 nm, and about 460 nm to about 500 nm, among others.

In another example, the circadian active wavelength range may also include wavelengths of green light selected from a group consisting of wavelength band ranges of: about 470 nm to about 560 nm, about 480 nm to about 550 nm, about 490 nm to about 555 nm, about 490 nm to about 560 nm, about 490 nm to about 565 nm, about 490 nm to about 570 nm, about 435 nm to about 490 nm, about 435 nm to about 470 nm.

Depending on the particular type of circadian protection required, sometimes the blue light wavelengths are attenuated. At other times, both the blue and green light wavelengths are attenuated. For example, the spectral power distribution in the particular wavelength ranges may be set according to the particular circadian state (e.g., day, night, evening) and desired circadian effect (e.g., protection or entrainment) of the individuals being illuminated.

In some embodiments, an environmental lighting system may be comprised of devices that emit light within a given space, including, for example, ceiling luminaires which may be, for example, troffers and/or down-lights, and may also include, for example, desk lamps, focused work area lighting, computer screens, television screens, indicator lights, and electronic tablet or cell phone screens.

The devices may be controllable and/or otherwise operable through a centralized control system, said centralized control system being a wireless system accessed via a software program on a computing device (e.g., laptop, tablet, or smartphone), which can instruct the environmental lighting system to adjust the spectral components emitted by the system to include or eliminate wavelengths of light within the range of wavelengths that are known to have a circadian effect (e.g., "blue-enriched" light or "green-enriched" light in particular wavelength ranges). In some embodiments, the centralized control system is a hardware chip that is plugged into existing infrastructure that receives information and encodes output command instructions and signals for transmission to light sources.

In some embodiments, the centralized control system may be controllable to set and/or control the light sources in relation to lighting characteristics, such as CCT, CRI, Duv, and light intensity. For example, the spectral power distribution may be controlled and/or compensated such that the lighting sources maintain a same, comparable and/or visually indistinguishable CCT, CRI, Duv, and/or light intensity (e.g., so that an individual with normal visual acuity may be less disrupted by (or unable to perceive) the variation of characteristics of the light being provided.

In some embodiments, in an environment lit by the environmental lighting system described above, an individual may be provided one or more devices (e.g., wearable devices which may be worn in many different fashions upon the body such as around the wrist, similar to a wristwatch; around the neck, as a pendant; etc.) that may be configured to communicate with a control system. The devices may include one or more sensors, such as light sensors, photodiodes, proximity sensors, location sensors (e.g., wireless triangulation, cellular triangulation, global positioning system sensors, and beacon technology), near-field communication sensors, accelerometers, gyroscopes, etc.

The devices may be configured for communication with the control system of the environmental lighting system in such a manner that provides sufficient information for the lighting system to identify various characteristics, such as the presence, orientation, altitude, and/or location within the area being lit of an individual. In some embodiments, light sensors may be used to determine the lighting conditions that an individual is exposed to. The sensory information may be used also by the system in generating one or more alerts and/or notifications, which, in some embodiments, may be auditory, visual, or vibratory cues that a person may be exposed to too much light in circadian active wavelength ranges (e.g., similar in operation to a radiation sensor that indicates a shriek or a beep when a person has surpassed radiation exposure limits).

In some embodiments, in an environment lit by the environmental lighting system described above, the environmental lighting system comprises one or more facial recognition systems, such as those implemented using video cameras that may be configured to communicate with the control system of the environmental lighting system in such a manner that it provides sufficient information for the lighting system to identify the presence and location within the area being lit of an individual.

In some embodiments, in an environment lit by the environmental lighting system described above, a facility's time-and-attendance system capable of providing sufficiently granular location information (e.g., at the individual room or desk level) is configured so that it communicates with the centralized control system located on a computing device. As an individual utilizes the time-and-attendance system to pass from area to area or room to room, the control system may communicate with the lighting system to identify the presence and location within the area being lit of an individual.

In some embodiments, in an environment lit by the environmental lighting system, the control system may be configured to communicate with an automated access security system that may be capable of providing location information (e.g., at the individual room or desk level). As an individual utilizes the automated access security system to pass from area to area or room to room, the control system may be configured to identify the presence and location within the area being lit of an individual, and control the lighting accordingly. Alternatively or in conjunction, such positional information may be obtained through estimated methods, such as triangulation through wireless network strength between two or more access points.

In some embodiments, in a space or portion of an environment where individuals are sufficiently sparsely distributed, each individual may be illuminated, depending on where they are in a particular environment and as they move around that environment, by lighting adapted to match their particular circadian state (e.g., reducing disruption to their natural circadian state) and/or desired circadian functioning (e.g., entrainment).

In some embodiments, the circadian states and desired circadian effects for one or more individuals in an environment or a portion of an environment may be evaluated and a circadian lighting condition may be established for that space that corresponds to the particular circadian state and/or desired circadian effect for the majority of the one or more individuals in the space.

In some embodiments, where there be no clear circadian lighting condition at the then current clock time for a majority of the individuals in a given area, a default circadian lighting condition, based upon pre-set defaults for the area being illuminated, may be established for that area.

In some embodiments, one or more logical rules may be applied that govern how the control system controls the light sources to adapt for the needs of a plurality of individuals. For example, a rule may be provided to implement one or more algorithms determining the lighting conditions that would have a minimal aggregate impact on circadian functioning of the individuals at a particular location.

For example, in a scenario where individuals are insufficiently sparsely distributed for individualized circadian lighting, the circadian states and desired circadian effects for the individuals in the area may be evaluated and the circadian lighting condition will be established for that space which corresponds to the particular circadian state and desired circadian effect for the majority of individuals in the space.

For example, if, after evaluating the current circadian states and/or desired circadian effects for the individuals in the area, the centralized system determines that a majority of those in the area need the lighting condition to be blue-depleted, the lights in that area will be set to their blue-depleted mode.

If, on the other hand, after evaluating the current circadian states and/or desired circadian effects for all individuals in the area, the centralized system determines that a majority of those in the area should currently be exposed to blue-enhanced lighting, the lights in that area will be set to their blue-enhanced mode.

Should there be no clear circadian lighting condition at the then current clock time for a majority of the individuals in a given area, a default circadian lighting condition, based upon pre-set and/or predetermined defaults for the area being illuminated, may be established for that area.

For example, five individuals are exposed to light from a number of light sources in a particular portion of an environment. The five individuals may be in different circadian states. Accordingly, they may have different circadian needs. The control system may identify these different needs and, in some embodiments, may be configured to conduct a determination of the aggregate impact on circadian functioning (e.g., by attaching one or more weights to various circadian outcomes) and controlling the operation of the light sources to reduce and/or minimize the aggregate impact. In some embodiments, the circuitry may be configured such that individuals requiring light adapted for an "evening" (biological early night) state are prioritized over other individuals.

In some embodiments, a logical rule may be applied such that the control system controls the light sources to provide lighting that has a spectral power distribution in one or more wavelength ranges (e.g., blue or green light) based on the individual requiring the lowest spectral power distribution in the one or more wavelength ranges.

For example, five individuals are exposed to light from a number of light sources in a particular portion of an environment. The five individuals may be in different circadian states. Accordingly, they may have different circadian needs. The control system may identify these different needs and, in some embodiments, may be configured to identify the individual requiring the most attenuation of light in particular wavelength ranges (e.g., a person on a "night" state), and control the lighting such that the light provided suits the individual requiring the most attenuation of light.

In some embodiments, the control system may be configured to customize and/or apply one or more timing sequences and/or timing programs for the delivery of light having various spectral power distributions (e.g., blue enriched, blue depleted) to individuals being illuminated.

In some embodiments, the control system may be configured to receive information from a wearable device, and the information may then be used to control one or more characteristics of light provided to one or more individuals. Information from the wearable device may be used in various manners, such as to where an individual is positioned, what orientation an individual is facing, the trajectory of an individual, the acceleration of an individual, etc.

The various positional elements of information may be used to determine, for example, that an individual is potentially entering/exiting another area, and in some embodiments, the control system may identify such behavior and predictively operate and/or control one or more light sources. Similarly, in some embodiments, the control system may be configured to determine when an individual is transitory and/or simply passing by an area (e.g., while being exposed to light from a particular light source, not staying within the proximity of the light emitted by the light source for a sufficient period of time), and therefore decide not to change the operation of the light source.

In some embodiments, the control system may be configured to receive information from a time-and-attendance system, and the information may then be used to control one or more characteristics of light provided to one or more individuals.

In some embodiments, the control system may be configured to receive information from a facility monitoring system (e.g., a security system, an access system, a credential system), and the information may then be used to control one or more characteristics of light provided to one or more individuals.

In some embodiments, the control system may be configured to receive information from one or more systems having facial recognition capabilities, and the information may then be used to control one or more characteristics of light provided to one or more individuals. Other biometric information aside from facial recognition may also be used.

In some embodiments, the control system may be configured to determine the identity, location, altitude and/or orientation of individuals. As the individuals move around a particular environment the control system may be used to provide lighting that is suitable for their circadian functioning (for example, the light from sources may be adapted as the individuals enter rooms, approach light fixtures). In some embodiments, the control system predictively adapts lighting in anticipation of the movement of an individual into a particular location and/or room. For example, if the control system predicts that an individual will enter a room (e.g., the individual is travelling towards the entrance to the room), the control system may vary the lighting in that particular room prior to the arrival of the individual.

In some embodiments, the control system may be configured to vary and/or customize the timing of the delivery of light having particular characteristics (e.g., blue-enriched and blue-depleted lighting) to individuals being illuminated based upon the metabolic needs (e.g., hunger, satiety) of the individuals being illuminated. There is evidence that exposure to blue light affects appetite and therefore hunger or satiety which may be related to time of day. There may be suppression and/or stimulation of various metabolic processes.

Light Tracking System

For some individuals, the phase of their circadian processes may become out of synchronization from their local natural circadian day, as a result of various factors, such as lifestyle, work schedule, travel across time zones, illness, light exposure, etc. For example, their circadian processes may be impacted by rotating or night shift-work schedules, trans meridian travel, sleep disorders, or being exposed to circadian-active light during the local night.

By using specially timed treatments using lighting systems with light enriched in spectral power in the 430-490 nm wavelengths (e.g., 5%, 10%, 15% of total visible power in the 430-490 nm wavelengths), synchronization issues related to circadian functioning may be treated and managed.

However, to provide treatment, there may be a requirement to determine the current phase of an individual's circadian processes. Some embodiments described within this specification describe devices, systems and/or methods that may be used to determine a current phase of an individual's circadian processes (e.g., a circadian state). This current phase may be used for various purposes, such as provisioning a control system to provide light in accordance with the individual's circadian state, determining the type of entrainment required to cause the individual's circadian state to change towards a desired circadian state, identify phase shifts required to modify a current circadian state, etc.

In some embodiments, information regarding the individual's circadian processes may also be used for other types of analyses and/or uses, such as for research purposes (e.g., population level research where individuals may be filterable and/or analyzable based at least on their circadian state and/or functioning), tailoring advertising relevant to an individual's circadian state, conducting health outcome based analyses, etc.

Biological markers, such as dim-light melatonin onset (DLMO) and/or minimum core body temperature (MCBT) can be used to determine the phase of an individual's clock, however the use of these markers may be impractical for individuals who are otherwise leading normal lives.

A potential alternative, less-invasive system for determining circadian phase where an individual's rest-activity pattern and record of light exposure can be used to generate a useful estimate of that individual's circadian clock phase may be described in embodiments below.

In some embodiments, a system may be provided to collect information associated with an individual's circadian functioning, such as historical light exposure and activity data, location logs (e.g., time spent indoors, outdoors, in which room being exposed to light from light sources located in the room), activity logs, device usage logs, work schedules, sleep times and wake times, etc.

The information may be collected from various sources, such as from records of a control system described in the embodiments described within this specification, self-reported logs, one or more devices (e.g., wearable devices) associated with an individual, use records of devices (e.g., smartphone/tablet usage at night), computer activity, work records, attendance records, etc.

In some embodiments, information may be combined with biological data, such as heart rate, blood pressure, sweat composition, etc.

The information may be used, for example, to estimate an individual's circadian phase and/or other characteristics associated with the circadian functioning of an individual. The information may be used to assess not only a present circadian state of an individual, but also to determine whether the circadian functioning of an individual is consistent, inconsistent, etc.

Accordingly, based on this information, the information may be provided in various forms to one or more systems, or in some embodiments, provided through an interface to the individual or one or more healthcare practitioners associated with the individual. The individual may be able to view and/or identify trends associated with his/her circadian functioning, and in some embodiments, compare his/her circadian functioning to the circadian functioning of others or an optimal circadian reference example. In one embodiment, the information may be provided to an employer or a facility manager, and for example, the information may be used for various purposes, such as to reduce risk to employers and/or to assist people with identified circadian abnormalities.

In some embodiments, the circadian information may be used to develop circadian entrainment programs that may be adapted to help individuals who may be intentionally shifting to a new circadian phase (e.g., switching from a day-shift to a night-shift).

The individual or a healthcare practitioner may then be able to suggest and/or implement various circadian entrainment regimens which may be used to cause various effects on the circadian functioning of the individual in relation to a desired and/or target circadian rhythm. For example, an individual may be transitioning to a shift work role and the individual may wish to entrain his/her circadian system in advance of a shift. Similarly, there may be desired entrainment related to travel, relocation (e.g., moving to a location several time-zones away), modifying irregular sleeping patterns, etc.

The information may be combined with other information associated with the individual, such as the individual's gender, age, ethnicity, genetic information, occupation, etc., for various analyses. This information, for example, may be used by various ways, such as in use for systems configured for entrainment of the circadian system, targeted advertising, the automatic adjustment of lights, reporting, scientific research, etc.

Example Embodiments—Light Tracking System

The information may be automatically generated, retrieved from external systems, provided in the form of self-reporting logs, streamed from one or more wearable devices positioned on and/or in proximity with an individual.

In some embodiments, an environmental lighting system may be configured to collect historical light exposure and activity data for an individual, for use in estimating the individual's circadian phase. For example, the environmental lighting system may be a system that is interconnected to and/or controls one or more light sources, such that various characteristics of the light provided to individuals can be controlled.

In some embodiments, the environmental lighting system may be configured to collect historical light exposure and activity data for an individual through logs kept and provided by the individual. These logs, for example, may include information about times spent indoors and outdoors; the nature of activity at these locations; and sleep times and wake times. The logged information may then be combined by the system with externally collected environmental information obtained from weather records, light-level recordings, work schedules, etc. for some or all locations and occupations identified in the individual's provided record.

In some embodiments, a wearable device collects historical light exposure and activity data for an individual through the use of the wearable device which, when worn by the individual, will record the individual's light exposure and activity data, including specific data about light exposure in the circadian-active wavelengths, and will maintain a log of that data over an extended, multiple-week period of time. The wearable device may, for example, have one or more sensors which may detect and/or estimate the amount of light provided to an individual.

In some embodiments, a lighting system may be configured to collect historical light exposure and activity data for an individual by assembling that data from externally collected environmental information obtained from weather records, light-level recordings, work schedules, etc. for some or all locations and occupations identified by the individual, or from known behavior of a group (e.g., shiftworkers on the same shift) of which the individual is a member.

In some embodiments, subsequent to the collection of the historical light and activity data, a system may be configured to analyze the data for an individual, seeking repeating, periodic patterns of sleep times, active times, and times of circadian light exposure, and from this analysis, produces an estimate of the circadian clock setting of that individual. This circadian clock setting may be used to understand and/or estimate the current circadian phase of the individual and/or whereabouts an individual is within a specific circadian state, and to generate a schedule of light treatment, specifying when one or more lights should expose an individual being illuminated by the lights to circadian-active light (e.g., light that may have effects on the functioning of the circadian system), and when the lights should ensure that an individual being illuminated under the lights is exposed to a minimum of circadian-active light (e.g., lights having particular wavelength ranges attenuated). Where an individual is transitioning between circadian states, the circadian clock setting should track the transition and the system may adjust the lighting that is providing illumination to the individual accordingly (e.g., through control of characteristics of the aggregate light provided to the individual).

In some embodiments, light and activity data will continue to be collected during scheduled light exposure from the light sources. This data will be used for continuing estimation of the circadian phase of individuals being illuminated by the lights, and may be used to provide verification that the lights are having the circadian effect that is desired.

In some embodiments, a light tracking system and an environmental control system may be combined together such that information the light tracking system is used, at least in part, to estimate a circadian state for an individual based on the amount of light exposed to the individual, and that information may be provided to the environmental control system. The environmental control system, having knowledge of an individual's estimated circadian state, may use this information to control/operate light sources to promote various circadian objectives, such as the maintenance/protection of a circadian rhythm, the entrainment of a circadian state (e.g., implementing a phase shift), etc.

Controlling Environmental Illumination Relative to the Angle of Incidence on the Eyes of One or More Individuals Studies have indicated that the directionality (e.g., the angle of incidence) of light provided from various light sources may have an impact on the potential circadian effects on individuals who are exposed to the light.

Light from lighting systems, when delivered from above the plane of visual focus (thus striking the lower retina) may have a greater circadian effect than light from these lighting systems when delivered from below the plane of visual focus (thus striking the upper retina), and/or light from lighting systems at the plane of visual focus. The plane of visual focus may be, for example, at an eye level, etc.

An eye level may be determined by the vertical mid-point of an eye, or any other level based on the positioning and/or orientation of the eye. In some embodiments, an eye level is determined by and extends from the vertical mid-point of an individual's eye when the eye is in the resting position. In some embodiments, an eye level is determined by and extends from the midpoint of an individual's eye in a direction that the eye is aimed towards (e.g., the eye level and/or plane of visual focus may depend on the angle a person's eye is angled towards).

For example, light delivered from above the plane of visual focus may have a greater effect on the circadian functioning of an individual as compared to a similar lighting system delivering light at and/or below the plane of visual focus, even if the light sources have a same and/or identical spectral power distribution.

Light may be provided directly from lighting sources, or in some cases, may be provided as light reflecting from various surfaces, such as mirrors, polished surfaces, etc.

Light that reaches the lower half of the retina (e.g., light that enters the eye from above in a person sitting or standing erect) can produce more circadian stimulus efficacy (in terms of melatonin suppression) than light that reaches the upper half of the retina (e.g., light that enters the eye from below in a person sitting or standing erect).

Without wishing to be bound to a theory, this effect is believed to be related to the topography of ganglion cell distribution in the eye, and may be as a result of human adaptation to the largest naturally-occurring source of circadian-active light, the sky.

In some embodiments, light may be provided where a significant amount of 430-490 nm wavelength blue light (and/or green light) is removed from provided visible light at night while maintaining acceptable levels of whiteness, color temperature (CCT) color rendering index (CRI) and intensity (for visual acuity, color and object discrimination and aesthetic appearance).

Because of the increased lower retinal sensitivity to light from above a plane of visual focus, the removal and/or attenuation of blue and/or green light from overhead applications may be particularly important (e.g., for overhead ceiling lights, troffers, pendants, high bay lights).

Various characteristics associated with a light source may impact the angle of incidence upon the eyes of one or more individuals, such as the positioning and/or orientation of the light, or the directionality, coherence, illumination/beam profile, etc. of the light provided by the light source. For example, a LED flashlight provides different light than an incandescent bulb. Further, a light source may have various features that may change characteristics associated with the light, such as various filters, light blocking and/or attenuating elements, light shades, etc. The features may, for example, attenuate light only in particular spectral wavelength ranges.

These filters and/or light blocking and/or attenuating elements may be disposed relative to a light source such that some or all of the light generated by the light source is affected, blocked and/or otherwise modified.

In some embodiments, the filters and/or light blocking and/or attenuating elements may impact light provided at different angles from the light source differently. A filter, for example, may consist of two parts, a first filter for filtering light being provided in a first set of directions, and a second filter for filtering light being provided in a second set of directions.

A light shade, for example, may be configured and/or positioned relative to a light source to block light in particular directions.

Individuals may be exposed to light from various directions, and from different light sources having different characteristics and/or positions. The orientation, posture, positioning, and/or movement of an individual may impact the directionality of light that the individual is exposed to. As the eyes of an individual are located in the head of the individual, the angling and positioning of the head may also impact the directionality of light that the individual is exposed to.

Where individuals are conducting tasks and/or activities where their movement and/or body posture/orientation is consistent (e.g., walking, conducting desk work, operating machinery, operating vehicles), it may be possible to configure and/or adapt lighting sources based on the predicted and/or real-time directionality of exposure to have various effects on the circadian processes of the individual. In some embodiments, the angle of incidence of light relative to the eye of an individual that is exposed to the light may be predicted based on information indicating that individual's expected tasks/movements, activity schedule, activity type, etc.

Individuals may also have limited mobility, and such individuals may include, for example, disabled individuals, individuals operating machinery, individuals confined to various positions, etc. Mobility may be restricted based on activity, environment, or the individual's physical capabilities. For these individuals, it may be difficult to avoid exposure from one or more light sources, and the positioning and/or control of these light sources may play a role in the circadian functioning of the individual. Light sources providing light from above the visual plane of focus may have greater effects on the circadian functioning of the individual as compared to similar light sources providing light at and/or below the visual plane of focus. For example, an individual may be a patient at a hospital who is being operated upon on an operating surface, a shift worker at a workstation, a worker in a factory, etc.

In some embodiments, devices having various types of sensors (e.g., cameras, proximity sensors, gyroscopes, accelerometers) may be used in determining the angle of incidence of light relative to the eye of an individual that is exposed to the light from one or more light sources. For example, a hard hat, a hat, a helmet (or other type of device associated with, disposed on and/or mounted on the head of an individual), a wearable device, a smart phone, etc. may indicate and/or otherwise provide information associated with the angle of incidence of light relative to the eye of an individual who is exposed to light from one or more light sources. These devices, head wear, etc., may also indicate the positioning and/or orientation of a head, the eyes, etc., which may be used to determine a visual plane of focus and/or an eye level.

Individuals may also be in environments and/or situations where the individual has limited/no mobility. For example, an individual in a hospital bed, a mobility-challenged individual, an individual operating machinery, etc. In these environments, the directionality of light that the individual is exposed to may be determined by characteristics of the various light sources, such as the position and/or orientation of the light source.

There may be situations where there is more than one individual present in an environment and the individuals are positioned and/or oriented differently from one another such that the angle of incidence from light provided from various light sources may be different for each of the individuals. For example, a first individual may be a patient on a hospital bed, and a second individual may be a surgeon operating on the first individual. In the context of this example, the first individual may be lying prone on the bed, while the second individual may be standing over the first individual and performing surgery.

An individual may be associated with and/or positioned near/on an operating surface. The operating surface may include work stations, desks, emergency room tables, hospital beds, etc. The operating surface may be associated with or have one or more sensors for detecting various characteristics of light that the operating surface is exposed to. The one or more sensors, for example, may be able to detect CCT, light intensity, CRI, etc., and provide the information to one or more control systems and/or one or more light sources. Information provided by these one or more sensors may be used to vary the operation of the one or more lights, for example, so that the light sources provide light with various minimum characteristics, such as a minimum CCT, CRI, light intensity, etc. Providing light having various characteristics to an operating surface may be helpful in situations where there may be requirements for lighting having at least certain characteristics, such as a sufficient CRI, CCT, light intensity, etc., so that one or more individuals are able to perform various tasks. For example, the operating surface may be a hospital bed in an emergency room, where a surgeon may be performing surgery and light having sufficient CRI, CCT, light intensity, etc., may be required so that the surgeon is able to visually distinguish between various parts of the patient's body.

The sensors may be able to and/or configured to receive light from a plurality of light sources. For example, there may be two or more light sources that provide light on to the operating surface.

The operating surface may also be associated with and/or may also provide location-based information, such as where the operating surface is located relative to one or more light sources, and/or where a potential eye level for an individual on and/or associated with the operating surface would be located. For example, there may be information indicating that the operating surface is a hospital bed in an emergency room that may have a patient disposed on it such that certain lights will be above the eye level of the patient, and certain lights will be below the eye level of the patient.

The individuals may have different lighting requirements. In an example involving a surgeon and a patient, the surgeon may require light having various characteristics that may be beneficial and/or required for conducting the various activities and/or tasks required for surgery.

The surgeon, for example, may rely on his/her visual acuity and color rendering to identify and/or distinguish between organs, blood vessels, bone, etc. There may be particular wavelengths of light and/or characteristics of light that may be beneficial for this individual that may, however, have deleterious impacts on the circadian functioning of another individual.

The patient, however, may be interested in maintaining and/or protecting his/her circadian functioning and may wish not to be impacted by the light required by the surgeon.

In some embodiments, the light sources may be positioned and/or operated taking these differing needs and requirements into consideration. For example, a light that contains circadian disrupting wavelengths but having characteristics needed for the performance of a task, such as surgery, may be preferably positioned below the eye level of another individual not wishing to have circadian disruption, such as a patient.

In some embodiments, systems, methods, non-transitory computer-readable media and/or computer system products may be provided to consider, modify and/or adapt the angle of incidence of light provided by one or more light sources upon the eyes of individuals exposed to the light in relation to various circadian outcomes, such as protection/maintenance of circadian functioning, entrainment of the circadian system, etc.

In some embodiments, a system may be provided that utilizes the angle of incidence of light upon the eyes to regulate the circadian and neuroendocrine effectiveness of the light being provided by one or more light sources. The angle of incidence may be controlled and/or otherwise detected so that light from the light sources may be controlled in various manners, such as changing the angle of light provided by a light source or identifying the angle of light provided by a light source as a factor to be contemplated in controlling the operation of one or more light sources. Light sources positioned above eye level, as compared with light sources positioned below eye level may be controlled differently given that the light sources positioned above eye level may have a greater potential impact on the circadian functioning of one or more individuals.

In some embodiments, the light sources may be controlled such that the position of the light sources may be changed (e.g., through movement along a track using a motor). In some embodiments, the light provided by the light sources may have various characteristics modified through, for example, the application of shades to shading the light in various directions and/or adding filters that may filter the light in one or more directions.

In some embodiments, a control system may be configured to take into consideration the potential and/or actual angle of incidence of light relative to the eyes of various individuals who may be exposed to the light from one or more light sources controlled by the control the system. The control system may be configured to adapt the light provided by the light sources accordingly in relation to various circadian outcomes (e.g., maintaining particular circadian processes or entraining the circadian system) or activity-based requirements (e.g., light in the blue wavelength range is needed by a particular individual at an angle and intensity sufficient so that individual may conduct an activity requiring light having various characteristics).

In some embodiments, a control system may be configured to determine whether light provided by one or more light sources will be below eye level or above an eye level for one or more individuals. The control system may be configured to control the light provided by the light sources taking into consideration whether the one or more light sources are above or below eye level. Different rules may be associated with above eye level light sources as compared with below eye level light sources, as light sources at different levels may have differing levels of effects on the circadian processes of various individuals.

In some embodiments, lights may be moved and/or positioned (e.g., as a result of an instruction transmitted by a control system) such that a light may be above or below the eye level of one or more individuals who are exposed to light from the light source.

In some embodiments, various apparatuses and/or environments may be provided wherein one or more light source may be positioned and/or otherwise arranged based on the eye level of one or more individuals who are exposed to lights from the one or more light sources. For example, apparatuses and environments may include hospital beds, equipment and/or fixtures in an operating room, working desks, workstations, etc.

In some embodiments, a hospital bed is provided having a first set of light sources positioned above the eye level of a patient with limited mobility, and a second set of light sources below and/or at the eye level of the patient. The first set of light sources may be configured and/or provided so that the light from the first set of light sources may have or may not have various circadian effects on the patient. For example, the first set of light sources may have spectral power in the blue/green wavelengths attenuated so that there is a reduced impact on circadian functioning. As another example, the first set of light sources may have spectral power in the blue/green wavelengths enriched so that there is an increased impact on circadian functioning. In some embodiments, the first set of light sources may be configured with various filters and/or other types of structural elements to vary the spectral power distribution of light in wavelength ranges associated with impacts on circadian functioning.

In some embodiments, the one or more light sources may be designed and/or configured such that despite the varying (enrichment or attenuation) of spectral power distributions in the first set of light sources, the light provided maintains a constant or near constant CCT, CRI and/or light intensity.

In some embodiments, the one or more light sources may be designed and/or configured such that despite the varying (enrichment or attenuation) of spectral power distributions in the first set of light sources, the light provided maintains a visually indistinguishable, comparable and/or similar CCT, CRI and/or light intensity with various types of conventional light sources.

In some embodiments, the hospital bed may have sensors that sense various characteristics of light that the sensors are exposed to. For example, the sensors may sense light intensity, CCT, color, CRI, directionality, etc.

In some embodiments, the hospital bed may have sensors that sense the presence, position and/or orientation of an individual disposed on the hospital bed and/or otherwise proximate the hospital bed.

In some embodiments, a workstation, a desk, a vehicle interior, etc., may be provided instead of a hospital bed.

In the example of a workstation, an individual may be working on a widget and the workstation itself may have various light sources positioned on it such that the individual and/or the widget is illuminated. In some embodiments, light sources positioned above the individual may be configured and/or provided to have/not have various circadian effects on the individual.

In some embodiments, a device may be provided that is positioned on and/or proximate to an individual's head, the device having one or more sensors that sense information associate with the orientation and position of the individual's head, and the device being able to communicate this information to one or more light sources and/or a control system which may then use information associated with the individual's head to predict and/or determine an eye level of the individual. This eye level, for example, may then be used in the control of the one or more light sources so that light sources above the eye level of the individual may be controlled to have or not have various circadian effects on the individual.

Example Control System

Figure 15:
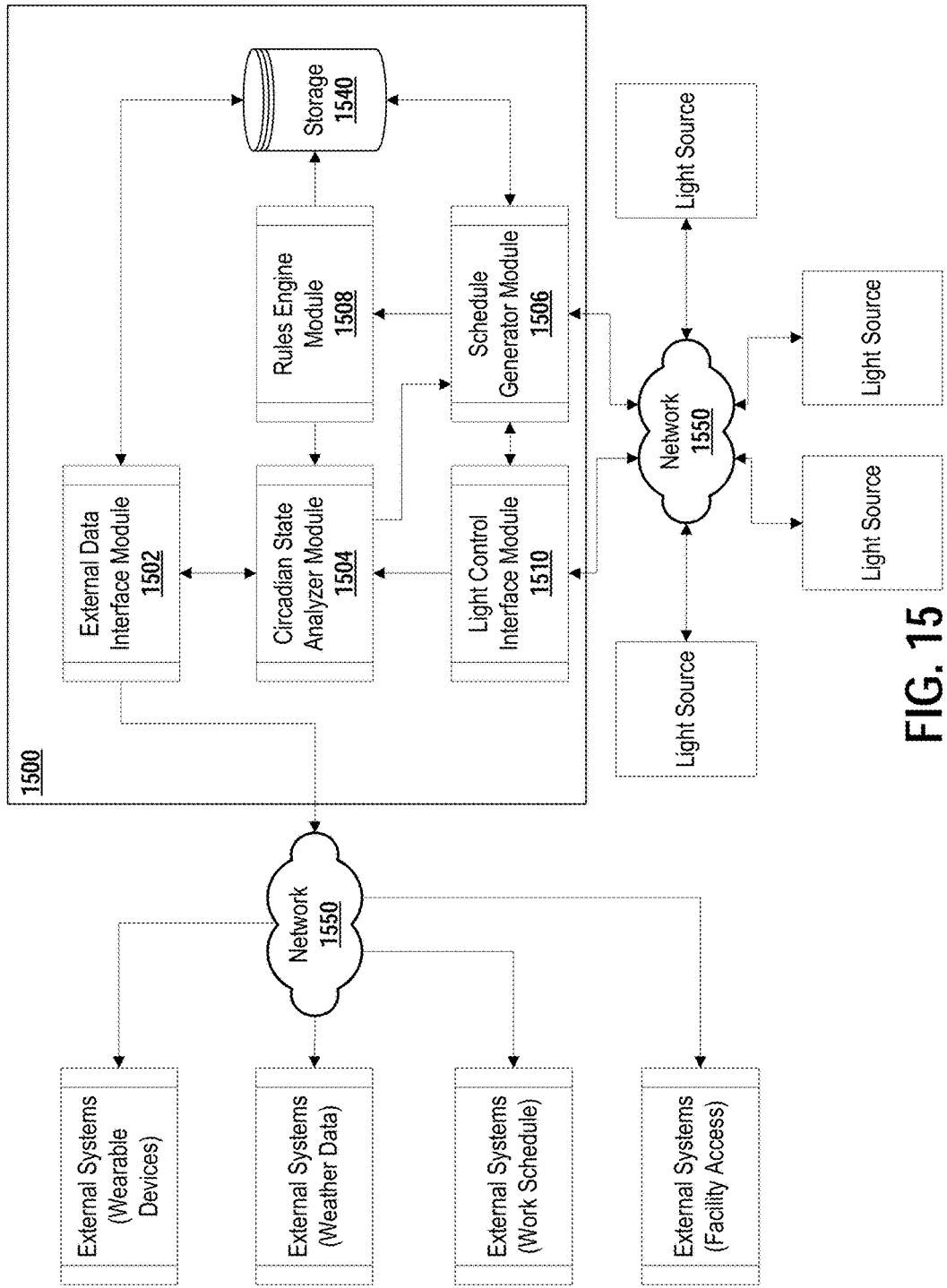
FIG. 15 is a block schematic diagram of a control system, according to some embodiments.

FIG. 15 is a block schematic diagram 1500 of a control system, according to some embodiments.

The control system may be comprised of storage 1540 and one or more units, including an external data interface unit 1502, a circadian state analyzer unit 1504, a schedule generator unit 1506, a rules engine unit 1508, and a light control interface unit 1510.

The storage 1540 may be used to store various elements of information received from external sources, as well as logical rules, historical light control information, etc. The storage 1540 may be implemented using various database technologies, such as relational databases (e.g., SQL databases), flat databases, excel spreadsheets, comma separated values, etc. If the storage 1540 is implemented using relational database technology, the storage 1540 may be configured to further store relationships between various data records. The storage 1540 may be implemented using various hardware of software technologies, such as solid state or hard disk drives, redundant arrays of independent disks, cloud storage, virtual storage devices, etc.

The external data interface unit 1502 may be configured for communication with one or more external systems and/or devices, such as wearable devices, weather/meteorological systems, facility security/access systems, self-reporting systems, etc. These systems may be configured to provide information in various forms, such as in data packets, analog signals and/or digital signals. In some embodiments, the information is streamed. In some embodiments, the information may be provided through batch, asynchronous and/or synchronous processes.

The information may provide various elements of information related to an individual and the individual's circadian functioning, such as the position, orientation, location, altitude, etc., of an individual, historical exposure to light and also other ancillary information, such as the amount and/or type of light present in ambient light and/or sunlight levels. Other personally-identifiable information may also be tracked by the control system.

Example sources of data include, for example, (i) one or more facility access databases, (ii) electronic calendar databases, (iii) tracked light exposure databases, (iv) location information databases, (v) work scheduling databases, (vi) indoor lighting schedules, (vi) outdoor lighting schedules, (vii) facial recognition platforms, (vii) travel record database, (viii) health records databases, (ix) fitness tracker databases and (x) outdoor light condition databases. Information from the different data sources may be weighted differently depending on various factors, such as data relevance, reliability scores, etc.

Where the control system is adapted to track evening exposure of "green" wavelengths, the storage 1540 may be further adapted to maintain electronic records tracking cumulative exposure (e.g., duration of exposure, intensity of exposure), the cumulative exposure being used to trigger a saturation point that may be tracked by circadian state analyzer unit 1504. For example, if evening exposure only has circadian effects up until a particular saturation point, there may be no need to prevent further exposure once a person is detected to have been exposed beyond the saturation point. Conversely, where a person is detected not to have been exposed beyond the saturation point, the control system may issue command instruction signals to various lighting devices detected to be in the vicinity or able to illuminate the person such that the person does not receive additional exposure to "green" wavelengths.

In some embodiments, the control system is adapted to track the directionality of light being incident on an individual. For example, the control system may be tap into a user profile established for an individual to access the individual's height, and estimate the individual's eye level. The control system may then apply different weightings related to exposure effects on that individual based on whether the light is provided above or below the individual's eye level, and in some embodiments, control lights at different levels accordingly, or, in further embodiments, move lights up and/or down to modify their post-weighting effects on the individual.

The lighting and/or circadian state information could be provided as portable document format files (PDF), comma-separated values (CSV), Microsoft Excel documents, extensible markup language (XML), hypertext markup language (HTML) or simply physical documents. In some embodiments, the control system obtains the information in a processed form (e.g., data indicative of desired circadian states and/or known exposure levels). In some embodiments, the control system is adapted to estimate and/or extract circadian state information based on known information that may not be simply exposure data, such as calendar records, activity records, etc. Where there are gaps and/or unknown exposure levels, the control system may interpolate and/or extrapolate levels based on reference data, or data having timestamps indicative of adjacent times.

Information may be provided over one or more networks 1550. The one or more networks 1550 may include the internet, intranets, point to point networks, etc. Networking technology may include technologies such as TCP/IP, UDP, WAP, etc. Information may also be provided through a multitude of current and legacy connection protocols including Bluetooth, Bluetooth low energy, USB, serial, infrared, NFC, WiFi, ANT+, etc. The interface, in some embodiments, may also be implemented using appropriate application programming interfaces (APIs).

The circadian state analyzer unit 1504 may be configured to determine various circadian information relevant to one or more individuals based on information stored in storage 1540. For example, the desired, current and/or future circadian state information may be determined.

Circadian state analyzer unit 1504 may provide state association and assign a circadian state to the individual based on the received electronic information (which may be provided in a pre-processed or processed state by the external data interface unit 1502. The circadian state analyser unit 1504 also tracks or estimates whereabouts within a particular circadian state a person is (e.g., towards the beginning of a day state, towards the end of an evening state) such that transition times are established. During the transition times, in some embodiments, the system gradually and/or smoothly transitions to another state by incrementally adjusting characteristics of lighting. In other embodiments, the system simply switches over to another setting when a transition time is noted between two states.

Circadian state analyzer unit 1504 is configured to extrapolate future circadian states based on the assigned circadian state (e.g., based on the current state, exposure levels, duration in the current state, when is the next state, what are the next states), etc. Future circadian states may include alternating day and night schedules, or in some embodiments, alternating day, early night and late night schedules. These schedules may be based off of a 24 hour clock, or any other type of clock. This information may be extrapolated and extracted based on estimations and/or approximations as derived from electronic information provided, such as a desired circadian rhythm (e.g., a person is travelling and wishes to have a sleep schedule entrained to reduce the effects of jet lag), etc.

The schedules may also vary over a period of time, for example, gradually entraining an individual's schedule to adapt gently to a changing schedule (e.g., modifying the schedule by a pre-determined amount each day, such as 10 minutes).

In some embodiments, these circadian states may include at least a biological night state. In some embodiments, the biological night state may be segregated and further classified between an evening state (e.g., biological early night state) and a late night state, identifying that each of these two night states may have differing circadian requirements for the individual. These circadian states assigned and/or determined for the individual may be stored on a database, such as one held in storage 1540.

The schedule generator unit 1506 may be configured for developing one or more identified circadian schedules, and may be associated with each of the one or more individuals that may be tracked by the control system. The circadian schedules may be used, for example, in determining how light provided by the lighting sources will be controlled by the light control interface unit 1510. The schedule generator unit 1506 may be configured to receive profile, circadian scheduling and/or high level exposure information from storage 1540, and transmit this information to the light control interface unit 1510.

The rules engine unit 1508 may be configured for the generation, adaptation, application, and/or modification of one or more rules that may govern the functioning of the control system. For example, logical rules, which may be implemented as logical instruction sets, may be used to prioritize, weigh various elements of information differently for analysis, or cause various effects on the operation and/or control of various light sources. In some embodiments, the rules engine unit 1508 may be configured to take into consideration the angle of incidence light provided by a light source will have on a particular individual, or a group of individuals. For example, the rules engine unit 1508 may be configured with a set of logical rules that may control the operation of light sources above the eye level of one or more individuals. Similarly, the rules engine unit may be configured with a set of logical rules that may control the operation of light sources below the eye level of one or more individuals.

In some embodiments, the rules engine unit 1508 is a standalone hardware chip where physical logic gates are provided that, for specific information inputs and high level control commands, causes the output of machine-level and machine-interpretable commands that are adapted for controlling the operation of the one or more light sources. In this example, the logic gates of the rules engine unit 1508 are adapted such that processing rules are hardwired into the operation of the hardware chip.

The light control interface unit 1510 may be configured for controlling the operation of one or more light sources. There is a lighting command encoding unit within the light control interface unit 1510 that receives the profile corresponding to the individual which may contain current circadian state, future circadian and/or desired state information. In some embodiments, such commands are provided in the form of source code, scheduling information, and/or instruction sets that may not be immediately process-able by the one or more light sources. Lights may be associated with control addresses, such as MAC addresses, short network addresses, group addresses, etc., and the light control interface unit 1510 may broadcast and/or otherwise provide control commands in a point to point manner. Where unknown light sources are added to the system, an automated discovery process may be initiated to register the unknown light source to the system in storage 1540.

The light control interface unit 1510 may encode and/or encapsulate specific machine-level control commands that are formulated based on the control parameters and inputs available to the one or more light sources. Such control commands may include, for example, voltage controls, amperage controls, controls to be provided to servomotors (e.g., to activate and/or deactivate specific components, such as filters, phosphors), electro-chromic filter controls, optical filter controls, etc. In some embodiments, machine-level the control commands include control commands for ancillary movement and/or rotation components, such as servomotors for moving light sources along tracks, guides, or rotating light sources to orient the light sources differently, etc. These machine-level control commands may, in some embodiments, take into account ambient or non-controllable lighting present in the environment when adjusting lighting of the controlled light sources.

The light control interface unit 1510 may be configured as a lighting command unit that controls how each of the one or more light sources operates. For example, light control interface unit 1510 may be a control bridge that relays control commands to endpoint light sources whose registered information is used to estimate the properties of the aggregate lighting provided to an individual by the endpoint light sources. Each of the endpoints may be registered, and where non-controllable lights (e.g., non-controllable circadian night-adapted lights) may be already present in the environment, these non-controllable lights may also need to be registered so that the light control interface unit 1510 is able to compensate for their light contributions when determining how machine-level control commands should be developed in view of desired circadian states/effects. For example, a sensor may detect that there is a level of light being provided through a window that enters the environment, and determine lighting levels and characteristics accordingly.

Control of operation may range from simply toggling various light sources on and off, to more granular control of operation, including commands to raise the intensity of a light source, to change the spectral composition of light provided by a light source, activating specific components such as violet light emitting sources, filters, phosphors, etc. Light sources may be programmatically registered with light control interface unit 1510 such that light control interface unit 1510 is able to determine what commands are available for operational control, such as control of color, brightness, hue, on/off, luminosity, additional components, etc. Further, for each command, an application interface and machine-level control protocols are identified and registered such that the application interface and machine-level control protocols are usable for control.

In some embodiments, when encoding and/or encapsulating specific machine-level control commands, the light control interface unit 1510 may need to utilize a combination of machine-level commands to modify the aggregate lighting provided by all of the light sources under its control. Depending on various parameters known regarding the light sources (e.g., distance, position, height, directionality), in some embodiments, various weights are applied to the contribution of each of the light sources in accordance to various output parameters, the weights determined such that the contribution of the light sources are proportional in their impact on the circadian functioning of an individual. The machine-level control commands are adapted such that the aggregate incident lighting provided by the one or more light sources provides light with a spectral power distribution having circadian-significant attenuation along a circadian active wavelength range during durations of time when the individual is in the biological night state. In some embodiments, the aggregate incident lighting provided by the one or more light sources has overall lighting characteristics within a pre-determined comparable range relative to the aggregate incident lighting provided by the one or more light sources when the one or more light sources are activated but not controlled to have circadian-significant attenuation along the circadian active wavelength range.

Where the directionality of the lighting may be a significant consideration, the light control interface unit 1510 may provide reduced weighting to light that is provided from below an eye level of an individual, or provide increased weighting to light that is provided from above the eye level of the individual. For example, the light control interface unit 1510 may classify each light source of the plurality of light sources as being above an eye level of the individual or below the eye level of the individual, the eye level of the individual being a horizontal cross-section if the individual is upright or a vertical cross-section if the individual is in a supine or prone position (e.g., such information may already be known regarding an individual, or estimated from workplace and/or activity information). Where there are multiple individuals, an average eye level may be estimated from height information extracted from user profiles (e.g., an offset based on average height), or in some embodiments, height information may be obtained from sensors worn by individuals (e.g., on a helmet).

In a simpler embodiment, the light control interface unit 1510 may simply be adapted to ignore the contribution of lights provided below the eye level of an individual. In some embodiments, the light control interface unit 1510 weights the lighting based on a factor applied based on their eye level, or distance from the individual, or a combination of both.

The light control interface unit 1510 may transmit adapted machine-level control commands to the one or more light sources. The machine-level control commands may be adapted in the form of machine-readable codes to lights having specific device identification numbers. In some embodiments, the lights are classified into specific clusters based on control properties, distances, or geographical positioning.

The light control interface unit 1510 may be provided information associated with the particular orientation and/or positioning of the light sources, as well as the options available in varying the particular characteristics of light provided by the one or more light sources. The light control interface unit 1510, for example, may be configured to also receive state information related to the operation of the light sources (e.g., a light source is faulty and is currently producing blue-enriched light despite instructions otherwise).

The light control interface unit 1510 may be controlled by the system to vary the lighting provided by the one or more light sources depending on the particular location, orientation, etc., of one or more individuals, as it relates to the positioning and orientation of the light sources. For example, the lights may be adjusted in a sub-area of a large room or even individually light by light depending who is in the illumination field of that light.

The light control interface unit 1510 may act as the part of the control system that communicates with the one or more light sources, and based on information about individuals' location and circadian status, uses schedule information associated with one or more individuals in conjunction with the application of one or more logical rules, and, though a data connection to the control boards in the lights (e.g., troffers) establishes the lighting condition appropriate to the individual or individuals being illuminated.

In some embodiments, the light control interface unit 1510 may be configured to control the positioning and/or movement of one or more light sources. For example, one or more light sources may be configured to be movable along a track, etc. The one or more light sources may then be configured to move such that the angle of incidence of light provided by the one or more light sources on one or more individuals is changed. For example, the angle of incidence may be changed from above eye level to below eye level.

In some embodiments, the light control interface unit 1510 may be configured to control the positioning, application and/or movement of one or more filter elements associated with the one or more light sources. For example, one or more filter elements may be configured to be applied to one or more light sources to attenuate light provided by the one or more light sources in various wavelength ranges. In some embodiments, the filter elements may be positioned such that only a portion of the light provided by the one or more light sources is impacted.

The light control interface unit 1510 may be adapted for encoding machine instructions that selectively activate light compensation components. These light compensation components include, for example, violet light emitting sources that are adapted to modify the spectral composition of light provided by the one or more light sources. For example, violet light emitting sources that emit light in a wavelength band selected from a group consisting of: between about 400 and about 440 nm, between about 400 and about 435 nm, between about 400 and about 430 nm, between about 400 and about 425 nm, and between about 400 and about 415 nm may be used in achieving a particular light profile that may be more amenable to the individual. The presence of these light emitting sources are a technical feature that alleviate deficiencies that may result in the aggregate output light, including undesirable coloration, intensity, color rendering, etc.

Further, these light emitting sources may be utilized to modify the output light such that when lights are switched and/or otherwise controlled between circadian states, the change of light is less easily perceived (or at least less perturbing) to an individual exposed to the light. For example, an individual may not wish to be alerted (or surprised) every time a circadian state shift is effected by the control system.

In some embodiments, the violet light emitting source provides an average irradiance greater than about four percent (4%), of the total irradiance from the light source in the visible light range. However, the amount of violet light may have an upper limit. As indicated through experimentation, when violet light is over expressed, an unnatural glow may be imposed on objects imposed by the light. In other embodiments, the violet light emitting sources emit light that, in respect of the aggregate incident lighting provided by the one or more light sources, provides an average irradiance selected from one of a group of percentage ranges including 10-15%, 15-20%, and 20-25% of the total irradiance from the light source in the visible light range. In a preferred embodiment, the violet light emitting sources provide 18% of the total irradiance from the light source in the visible light range.

Different average irradiance may be provided during the biological night state and in during states other than the biological night state. For example, the biological night state may be otherwise discolored due to the absence of blue and/or green wavelengths (attenuated for circadian protection). Violet light emitting sources within the light sources may be utilized to modify the color provided, and the amount of violet light may vary depending on the amount of attenuation and the wavelengths attenuated. For example, such variation may result in differences in amount of violet light being emitted in an early evening and a late evening state.

In some embodiments, the light control interface unit 1510 is adapted not only for providing machine-level commands to attenuate wavelengths within circadian active wavelengths and/or compensation thereof by adding compensatory wavelengths (e.g., violet light), but also for potentially attenuating non-circadian active wavelengths (e.g., those having longer wavelengths than blue and/or green) to aid in the tuning of aspects of the aggregate incident lighting. For example, non-circadian active wavelengths that are also attenuated include at least wavelengths between 490 nm and 700 nm, or non-circadian active wavelengths that are also attenuated include at least wavelengths between 560 nm and 700 nm.

The non-circadian active wavelengths being attenuated need not be uniformly attenuated. In some embodiments, specific "notch" filters may be utilized to attenuate the non-circadian active wavelengths unevenly or at specific wavelength ranges that are not consecutive with one another. Similarly, light propagating elements (e.g., violet light emitting sources) may proportionally be increased and/or decreased in view of such attenuation of non-circadian active wavelengths.

For example, the aggregate lighting may be provided that is detected by a light sensor or other type of feedback mechanism to be "too orange". The light control interface unit 1510 may then issue control commands that attenuate non-circadian active wavelengths such as those in various "orange" wavelengths to cause a shift of an overall coloration back towards a color that is not "too orange".

A feedback loop mechanism may be instituted to aid the light control interface unit 1510 in controlling the operation of the light sources. For example, tracked sensor information may indicate the presence of undesired characteristics of light (e.g., those outside specification) and encoding of machine-level commands and encapsulation may be modified in accordance of the tracked sensor information. Various types of feedback loop controllers may be used, such as a proportional controller, a proportional-integrative controller, and a proportional-integrative-derivative controller.

In some embodiments, the feedback loop mechanism may include biochemical or other type of biological sensor that may be directly or indirectly monitoring circadian responses of an individual (e.g., measuring melatonin stimulation levels). The biochemical or biological sensor may include sensors measuring chemical properties of tears, sweat, urine, blood, saliva, among others.

A feedback loop mechanism may include both biologically monitored circadian responses and The measurements may be tracked continuously, periodically, and may be normalized based on age, gender, weight, ethnicity, activity levels, etc. In some embodiments, these measurements are saved into a database and used for comparison to determine whether lighting effects at particular periods of time had desired effects, and if not, to generate a notification or corrective measure to either increase attenuation effects during states where the system is not particularly effective, or to notify a healthcare professional of an abnormality/abnormal reading.

Sensory data may be tracked, for example, and may be combined with various types of wearable device information, such as information stored and/or tracked using Fit-Bits™, smart scales, etc. The data may be aggregated together or provided in the form of a subscription service that may be configured to permit individuals to monitor their circadian data (and track the effectiveness of their lighting controls.

Example Embodiments

In some embodiments, an arrangement of lighting (e.g., positioning, orientation, type) in an electrically-illuminated environment may be performed, taking into account various natural and artificial light sources, the optics, the spectral reflectivity of surfaces and the properties of materials in the environment that fluoresce, and lighting in the environment. Light sources in the environment may be arranged and/or configured to illuminate individuals present in the environment in a manner that may be consistent with their desired or prescribed circadian treatments and/or circadian outcomes.

The light from the light sources may be arranged and/or configured such that light from the light sources reaches the individuals at various angles of incidence.

For example, light sources that may be configured to have an effect on the circadian functioning of one or more individuals, such as light sources having circadian-active spectral power distributions may be designed, positioned, controlled and/or installed such that light from the light sources is provided from a position above the eyes of individuals being illuminated.

Light sources adapted and/or configured to have minimal circadian effect (e.g., regardless of spectral power distribution) may be positioned, designed and/or installed such that light from the light sources may be provided from a position and angle that is below the eyes of individuals being illuminated.

In some embodiments, light sources providing light with circadian affecting characteristics (e.g., spectral power distributions having circadian significant power being provided in the blue and/or green wavelength ranges) may be installed and/or otherwise positioned such that light from the light sources is provided from below the eyes of the one or more individuals being illuminated.

In some embodiments, where lighting is controlled, and/or otherwise designed, the light provided to one or more individuals is provided taking into consideration whether the light sources are above/below the eyes of the one or more individuals, and also configured to correspond to various desired circadian effects.

Example Environments

These environments, may for example, include environments where individuals have limited mobility. For example, environments may include the cabin of a vehicle (e.g., an airplane, a car, heavy machinery, a truck), where the positioning of various lighting sources is known and the orientation and/or positioning of individuals may be known (e.g., an operator in an operator's seat). Dashboard lighting may be known to be around and/or below eye level for the operator, while lights positioned overhead and/or natural light may be known to be above eye level of the operator.

As another example, the cockpit of an airplane or a manufacturing facility may be considered where there may be light sources that are disposed at levels above (e.g., overhead lighting) and/or light sources that are disposed below (e.g., floor lighting) the eye level of various individuals. A control system as described in some embodiments may be integrated into the lighting control of the airplane, and may control, for example, properties of track lighting on the upper part of an airplane, emergency track lighting on the lower part of an airplane, etc.

In respect of passengers on an airplane, a flight manifest provides electronically extractable information that is indicative of destinations and origins. Especially for long flights that travel across multiple time zones, a control system as described in some embodiments may be helpful for entraining the circadian schedule of the passengers by coordinating lighting provided to the individuals through lighting throughout the airplane, such as on in-flight entertainment systems, in-plane lighting, etc. The lighting on an airplane may be readily modeled in view of airplane specifications and customizations (e.g., by airline, by plane model, by plane configuration), and lighting information may be registered into a computing system.

As passengers are generally fixed in their seats, their eye level is readily determined or estimated and the directionality of light can be taken into consideration in controlling the circadian-stimulating aspects of the light sources. The control system may adapt the changes to the lighting to subtly change the aggregate lighting to avoid startling or alarming the passengers, and such features may be especially helpful for passengers who are unable to sleep on long flights and are thus exposed to a high amount of ambient lighting during the flight. Accordingly, a circadian schedule may be established wherein passengers are provided with modified biological night (e.g., including "early night" and "late night" states) states that are derived based on time zone differentials between a point of origin and a point of arrival. The controllability of lighting based on circadian entrainment may be especially important to business and/or frequent travellers.

Figure 16:
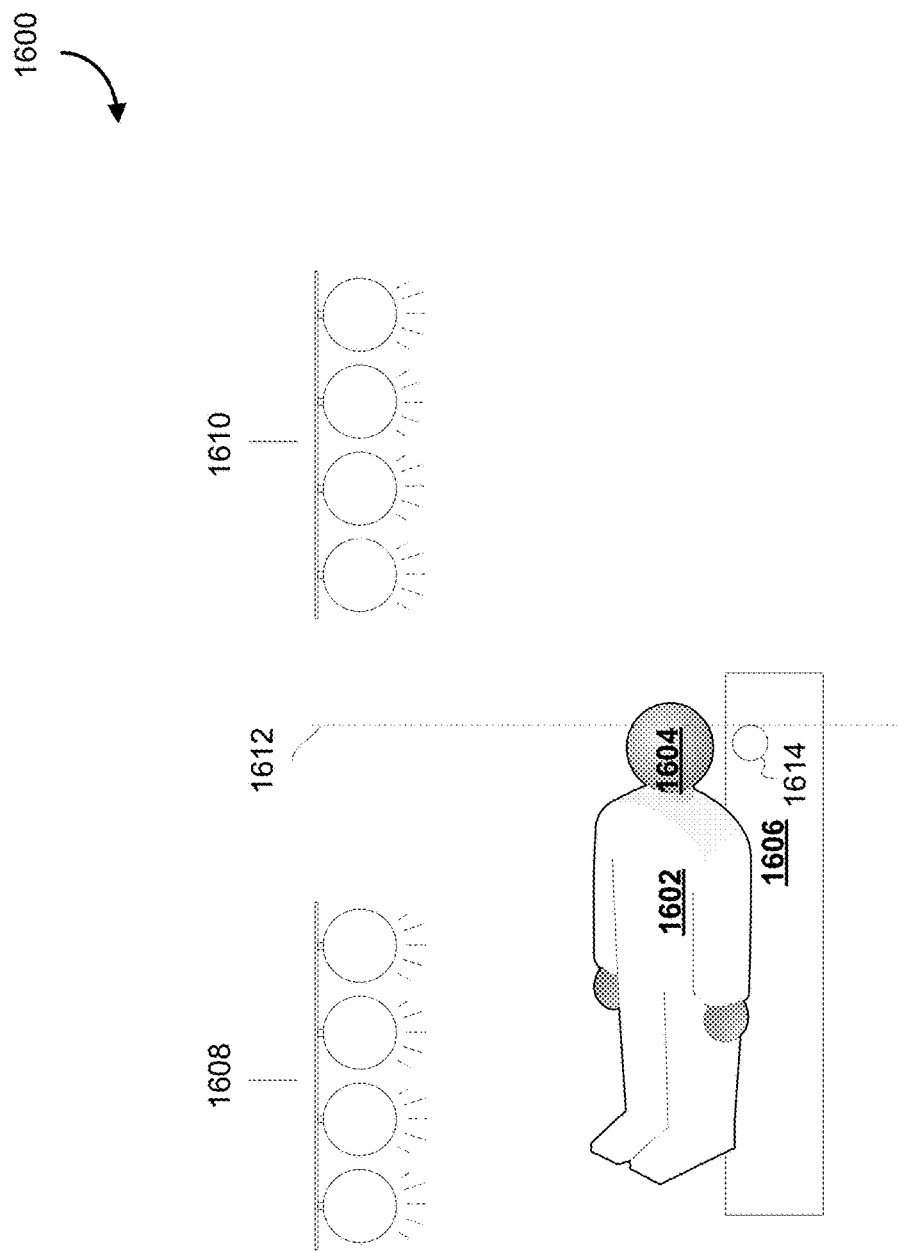
FIG. 16 is a sample illustration of an environment having an individual with limited mobility, according to some embodiments.

FIG. 16 is a sample illustration 1600 of an environment having an individual with limited mobility, according to some embodiments.

An individual having limited mobility 1602 is provided, the individual 1602 having a head 1604, resting on a surface 1606, while being illuminated by a first set of light sources 1608 and a second set of light sources 1610. The individual 1602's eye level 1612 is indicated by a dotted line extending from the individual's head 1604. The surface 1606 may also include a light sensor 1614.

The first set of light sources 1608 is positioned such that the light provided by the lights will have an angle of incidence to the individual's head lower than his/her eye level 1612.

The first set of second sources 1610 is positioned such that the light provided by the lights will have an angle of incidence to the individual's head lower than his/her eye level 1612.

As describe in some embodiments above, the light provided by the first set of light sources 1608 may have a reduced circadian impact on the individual 1602 as compared to similar light provided by the second set of light sources 1610.

Accordingly, the first set of light sources 1608 and the second set of light sources 1610 may be controlled differently in view of the differing levels of circadian impact that light from each set of light sources will have on the individual 1602's circadian functioning.

In some embodiments, the first set of light sources 1608 and the second set of light source 1610, while providing different levels of circadian impact, may be configured, arranged, and/or matched such that a comparable CCT, CRI and/or light intensity is provided. The characteristics of light may be comparable such that an individual of normal visual acuity may not be able to notice a significant difference. In some embodiments, the CIE 1931 chromaticity coordinates of the light provided by the first set of light sources 1608 and the second set of light source 1610 are within a 2 step MacAdam ellipse of each other and/or the difference between their CCT values is less than 5%. In some embodiments, their CCT values differ by 5K, 10K, 25K or 50K.

In some embodiments, the light sensor 1614 may include one or more sensors that may be configured to sense characteristics of light received by the light sensor 1614. For example, the light sensor 1614 may be positioned at a work area associated with the surface 1606 where one or more individuals may require light having various characteristics or sufficient characteristics such that the individual is able to perform various tasks.

Information from the light sensor 1614 may be used in the operation and/or control of the first set of light sources 1608 and/or the second set of light sources 1610.

Figure 17:
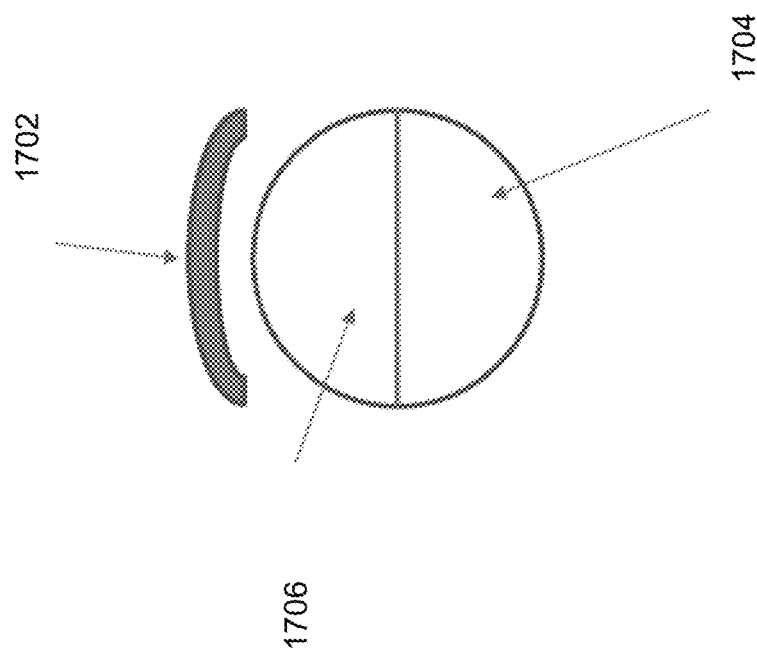
FIG. 17 is a sample illustration of the eye of an individual, indicating where the superior retina (upper portion of the eye) may be located, and the inferior retina (lower portion of the eye) may be located, according to some embodiments.

FIG. 17 is a sample illustration 1700 of the eyes of an individual (eyebrow 1702 is shown for spatial reference), indicating where the superior retina 1706 (upper portion of the eye) may be located, and the inferior retina 1704 (lower portion of the eye) may be located, according to some embodiments.

The term "eye level" as referenced throughout this specification may be used to distinguish between light falling on the superior retina 1706 (which may have less relative circadian effect, or may be circadian-ineffective) and inferior retina 1704 (which may have more relative circadian effect).

For example, for an eye looking forward at an 180 degree angle from the plane of the pupil, the superior retina 1706 is the half of the retina closest to the eyebrow 1702. The positions of the superior retina and inferior retina 1704 may be related to the orientation and position of the eye and/or head of the individual.

Example Wearable Device

Figure 18:
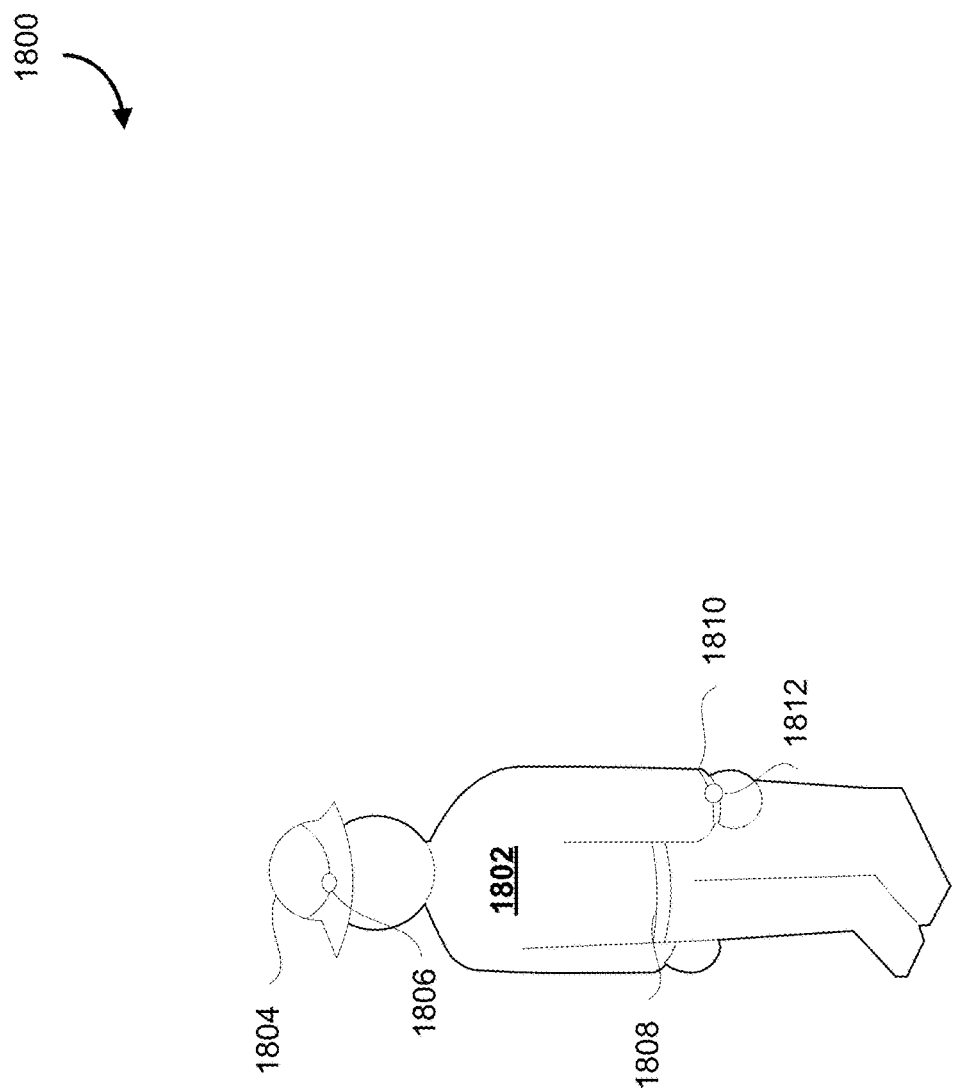
FIG. 18 is an illustration of an individual wearing devices configured to provide information to a control interface unit, according to some embodiments.

FIG. 18 is an illustration 1800 of an individual 1802 wearing devices configured to provide information to a control interface unit, according to some embodiments. The devices depicted include a helmet 1804 (e.g., having sensor 1806) and/or a watch 1810 (e.g., a smart watch having a sensor 1812), but may also include any other type of device having sensors, such as a sensor located on a belt 1808, a badge, etc. These devices may also track profile information, light exposure information (e.g., through the use of various light sensors), position, altitude, eye level, etc.).

Metabolism Embodiments

Some embodiments generally relate to mechanisms by which artificial light and lighting systems influence human appetite and feeding. These embodiments relate to the time of day that light exposure occurs, and the direction of the resulting change on these systems: either increasing appetite and feeding behavior, or decreasing them. These embodiments also specify the spectral characteristics of light that are the most biologically active wavelengths influencing the appetitive system. One embodiment is that artificial light sources that either emit or are devoid/have reduces of these biologically active wavelengths, and can be delivered at a time of day to stimulate or suppress appetite, such that appetite can be stimulated or suppressed at any time of day by the appropriate combination of wavelengths and time of light exposure. A use of artificial light sources created and applied in this manner is to augment or reduce appetite for individuals with particular dietary goals or in certain clinical situations where influencing appetite is desirable from a medical and health perspective.

In some embodiments, systems and methods may be provided for the control of lights in relation to how exposure to light may influence appetite and hunger, as well as accepted physiological markers associated with appetite and hunger.

As the influence of light on appetite and hunger may be wavelength specific, energy in the blue portion of the visible light spectrum may be biologically significant in influencing hunger and appetite. For example, the specific wavelengths within the blue portion of the visible light spectrum may include light having wavelengths between 450 to 490 nm.

The influence of light on appetite and hunger may be time-dependent. Light exposure in the morning decreases appetite and hunger. The morning hours include the approximate time many people eat breakfast, 0-2 hours after awakening. Light exposure in the morning increases circulating levels of leptin, which is a hormonal marker of satiety.

Light exposure in the morning decreases ghrelin, which may be indicative of reduced hunger. Light exposure in the evening may increase appetite and hunger. The evening hours include the approximate time many individuals eat dinner, 10-12 hours after the time the individuals wake from sleep.

Light exposure in the evening decreases circulating levels of leptin, which is a hormonal marker of satiety. Light exposure in the evening increases circulating levels of ghrelin, which is indicative of increased hunger.

Artificial light sources that specifically emit or are enhanced with blue wavelengths, or that are specifically devoid of blue wavelengths, can be used at the appropriate time of day, as specified above, to provide a tailored approach to stimulate or suppress appetite by altering the indoor lighting characteristics.

Artificial light sources used in the morning hours that specifically emit or are enhanced with blue wavelengths, combined with artificial light sources used in the evening that are devoid of blue wavelengths can be employed as an appetite-suppressing light regimen.

Artificial light sources used in the morning that substantially attenuate and/or are devoid of blue wavelengths, combined with artificial light sources used in the evening that specifically emit or are enhanced with blue wavelengths can be employed as an appetite-stimulating light regimen.

Other Applications

The following section describes potential applications that may be practiced in regards to some embodiments. There may be other, different, modifications, etc. of the below potential applications, and it should be understood that the description is provided as non-limiting, illustrative examples only. For example, there may be additions, omissions, modifications, and other applications may be considered.

In some embodiments, a light tracking system may be used to monitor light exposure and/or determine when an individual has reached a threshold of exposure to light having particular characteristics. For example, the light tracking system may be configured to track and/or identify when an individual has been exposed to a prolonged exposure of light having circadian disruptive effects for a period of time.

The information may be used, for example, to cause a notification to be sent to indicate that the individual should be removed and/or replaced as the individual has reached a maximum exposure.

There may be applications related to individuals having very long working hours and/or jobs requiring attentiveness and dexterity. If an individual is identified has being circadian-disrupted for a prolonged period of time, the individual may not be able to function effectively or properly in carrying out his/her activities. In the context of a surgeon at a hospital, there may be severe and/or dangerous ramifications to the health of patients.

In some embodiments, the control system may be used in conjunction with and/or as an addition to various home and/or facility automation products, such as Google's Nest™ system, Internet of Things enabled appliances, facility access and/or security systems, etc. The control system may be configured for communication through various protocols, such as Wifi, ZigBee™, Z-Wave™, Insteon™, Z-Wave™, etc., and may also utilize information associated with the location, schedule and/or calendar of one or more individuals in controlling the operation of one or more light sources.

For example, upon detecting that an individual is about to enter his/her home after working, the system may be configured such that the circadian lighting environment provided to the individual may already be provisioned in advance of the entrance of the individual.

Similarly, for suitably configured appliances, lighting provided by these appliances (e.g., a stove light, a refrigerator light) may be controlled such that the lighting is circadian-appropriate for an individual.

In some embodiments, certain groups of people working irregular hours or night shifts or rotating shiftwork schedules may have chronically damped (low amplitude) circadian rhythms, with for example chronically suppressed melatonin levels. These people may need a stronger more powerful entraining regimen with higher contrast between day (blue) and night (no blue) conditions for a period of time to re-establish their circadian rhythm amplitude and nocturnal melatonin levels over a period of time.

In some embodiments, the system may be used in conjunction with a "smart temporary accommodation system", for temporary accommodations such as hotels, hostels, barracks, camps, etc., where there may be individuals residing who may have specific circadian needs. For example, the individuals may have travelled across various time zones and require adjustment and/or entrainment of their circadian systems. These individuals may benefit from a system that recognizes their origin and destination locations and/or time zones and/or controls the lighting in their room or any other environment accordingly.

General

Some embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface. Program code may be applied to input data to perform some of the functions described herein and to generate output information. The output information may be applied to one or more output devices.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The foregoing discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

"Circadian rhythm" is a broad term and is used herein in its ordinary sense, and, for example, generally refers to the cycle of approximately 24 hours in the physiological processes of living organisms. As discussed above, the master circadian clock in mammals is located in the Suprachiasmatic Nuclei (SCN), a group of cells located in the hypothalamus. The SCN receives information about illumination through the eyes. The retina of each eye contains special photoresponsive retinal ganglion cells (RGCs) along with traditional photoresponsive rods and cones. These RGCs contain a photo pigment called melanopsin, and follow a pathway called the retinohypothalamic tract, leading to the SCN. Recently, evidence has emerged that circadian rhythms are found in cells in the body outside the SCN master clock, in other words the expression of genes in various tissues throughout the body also follows a circadian rhythm pattern. In the context of the present disclosure, a "clock gene" is a broad term and is used herein in its ordinary sense, and, for example, generally refers to a gene that follows such an expression pattern and is responsible for maintaining circadian oscillations in a specific cellular physiology. It is estimated that about 25% of the human genome shows such a periodicity in expression. There may be various states involved in a circadian rhythm, such as a day state, a night state, and/or other transitional states in between.

In the context of the present disclosure, "maintaining the circadian rhythm and/or state" of an individual is a broad term and is used herein in its ordinary sense, and, for example, generally refers to maintaining the amplitude and periodicity of the circadian oscillations observed in physiological processes including, but not limited to, melatonin and cortisol secretion and clock gene expression that would be present in the subject exposed to the geophysical light/dark cycle.

In reference to the present disclosure, the "individual" is a broad term and is used herein in its ordinary sense, and, for example, generally is a mammal, preferably a human. There may be particular advantages conferred where the subject is a female human subject and even more advantages where the subject is pregnant.

"About" is a broad term and is used herein in its ordinary sense, and, for example, generally in the context of wavelength ranges refers to +/−5 nm. For example, a skilled person would understand that about 430 nm may also mean 429 nm or 431 nm.

"Approximately" is a broad term and is used herein in its ordinary sense, and, for example, generally in the context of wavelength ranges refers to +/−5 nm. For example, a skilled person would understand that approximately 430 nm may also mean 429 nm or 431 nm.

In the context of the present disclosure, a "filter" is a broad term and is used herein in its ordinary sense, and, for example, generally is a device that substantially blocks a range of non-transmitted wavelengths of light.

"Retinal exposure" is a broad term and is used herein in its ordinary sense, and, for example, generally refers to light impingement upon the retina of a subject.

"Night" is a broad term and is used herein in its ordinary sense, and, for example, generally refers to the natural hours of darkness and, more specifically, to the dark phase of the geophysical light/dark cycle. In summer, in peri-equatorial latitudes, this is roughly equivalent to about 2100 hr (9 pm) to about 0600 hr (6 am), which are the peak hours of melatonin production. "During the night" is a broad term and is used herein in its ordinary sense, and, for example, generally refers to any time during this period. In the case of methods for minimizing circadian disruption in blue and/or blue green-light, preferably, the method may be practiced during the night and/or evening.

"Pump" is a broad term and is used herein in its ordinary sense, and, for example, generally refers to a quality of the light to produce a high intensity spike of light within a defined range within the spectrum of light.

The term "connected" or "coupled to" may include both direct coupling (in which two elements that are coupled to each other contact each other) and indirect coupling (in which at least one additional element is located between the two elements).

Figure 19:
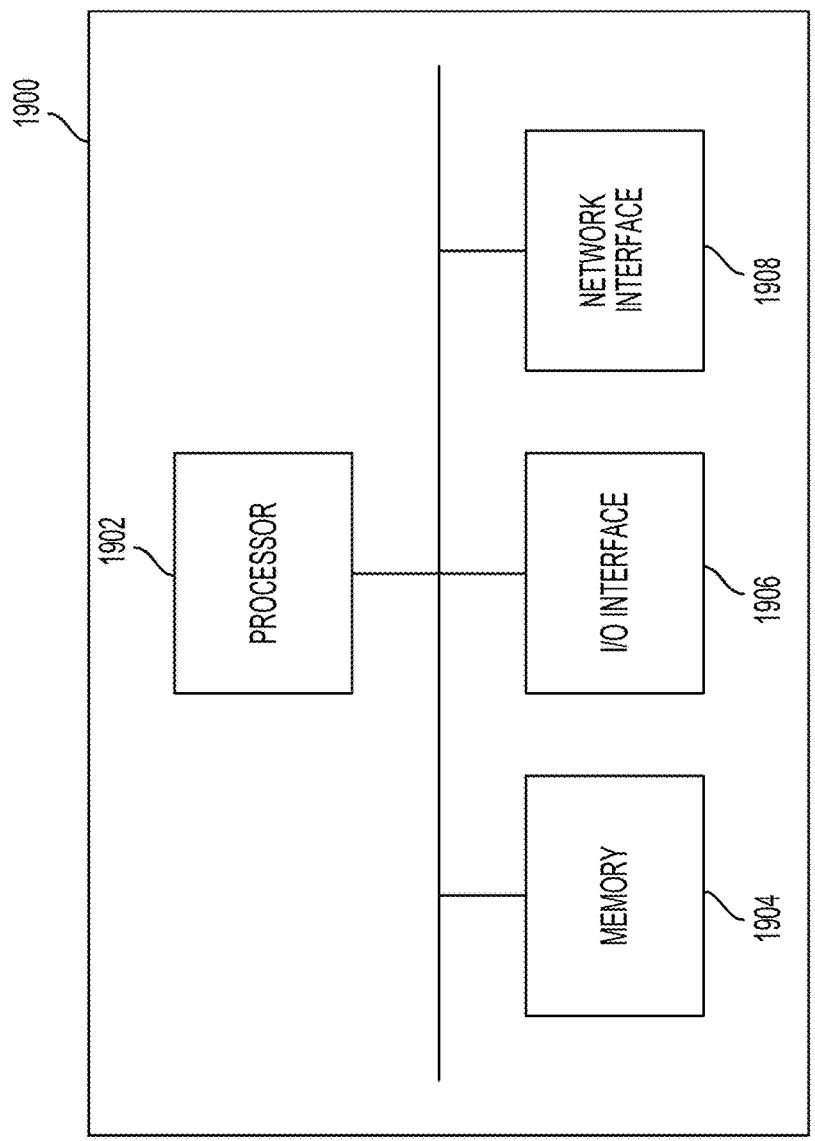
FIG. 19 is a schematic diagram of computing device, exemplary of an embodiment.

FIG. 19 is a schematic diagram 1900 of computing device 1900, exemplary of an embodiment. As depicted, computing device includes at least one processor 1902, memory 1904, at least one I/O interface 1906, and at least one network interface 1908.

Each processor 1902 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory 1904 may include a suitable combination of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 1906 enables computing device 1900 to interconnect with one or more input devices, such as a keyboard, mouse, camera, touch screen and a microphone, or with one or more output devices such as a display screen and a speaker.

Each network interface 1908 enables computing device 1900 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. WMAX), SS7 signaling network, fixed line, local area network, wide area network, and others, including combinations of these.

Computing device 1900 is operable to register and authenticate users (using a login, unique identifier, and password for example) prior to providing access to applications, a local network, network resources, other networks and network security devices. Computing devices 1900 may serve one user or multiple users.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

Some embodiments described herein may be implemented by physical computer hardware, including computing devices, servers, receivers, transmitters, processors, memory, displays, and networks. Some embodiments provide useful physical machines and particularly configured computer hardware arrangements. Some embodiments provide are directed to electronic machines and methods implemented by electronic machines adapted for processing and transforming electromagnetic signals which represent various types of information.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

What is claimed is:

1. A system for operating one or more light sources providing illumination to an individual, the system comprising:
   a data receiver unit configured to receive electronic information indicative of a circadian state of an individual from one or more data sources;
   a circadian state association unit configured to assign a circadian state to the individual based on the received electronic information, configured to extrapolate future circadian states based on the assigned circadian state, and configured to update a profile corresponding to the individual with the assigned circadian state and the extrapolated future circadian states, the assigned circadian state or the extrapolated future circadian states including at least a biological night state;
   a lighting command encoding unit receiving the profile corresponding to the individual and encoding machine-level control commands that control the operation of the one or more light sources; and
   a lighting command unit configured to transmit the machine-level control commands to the one or more light sources, the machine-level control commands adapted such that the aggregate incident lighting provided by the one or more light sources provides light with a spectral power distribution having circadian-significant attenuation along a circadian active wavelength range during durations of time when the individual is in the biological night state, and the aggregate incident lighting provided by the one or more light sources has overall lighting characteristics within a pre-determined comparable range relative to the aggregate incident lighting provided by the one or more light sources when the one or more light sources are activated but not controlled to have circadian-significant attenuation along the circadian active wavelength range;

wherein the circadian active wavelength range includes wavelengths of blue light and green light;

wherein the biological night state further includes (i) a biological early night state, and (ii) a biological late night state;

wherein for the biological early night state, the lighting command encoding unit encodes machine-level control commands such that the aggregate incident lighting provided by the one or more light sources provides light with a spectral power distribution having circadian-significant attenuation along both the blue and green wavelength ranges during durations of time when the individual is in the at least one biological early night state; and wherein for the biological late night state the lighting command encoding unit encodes machine-level control commands such that the aggregate incident lighting provided by the one or more light sources provides light with a spectral power distribution having circadian-significant attenuation along the blue wavelength range during durations of time when the individual is in the at least one biological late night state, while substantially transmitting light along the green wavelength range.

2. The system of claim 1, wherein the circadian active wavelength range includes wavelengths of blue light.

3. The system of claim 2, wherein the circadian active wavelength range includes wavelengths of blue light provided between about 430 nm to about 490 nm.

4. The system of claim 2, wherein the circadian active wavelength range includes wavelengths of blue light selected from a group consisting of wavelength band ranges of: about 430 nm to about 500 nm, about 430 nm to about 490 nm, about 430 nm to about 480 nm, about 430 nm to about 470 nm, about 435 nm to about 500 nm, about 435 nm to about 490 nm, about 435 nm to about 480 nm, about 435 nm to about 470 nm, about 440 nm to about 500 nm, about 440 nm to about 490 nm, about 440 nm to about 480 nm, about 440 nm to about 470 nm, about 450 nm to about 500 nm, about 450 nm to about 490 nm, and about 460 nm to about 500 nm.

5. The system of claim 2, wherein the aggregate incident lighting provided in the circadian active wavelength range is attenuated to a percentage of an overall spectral power in a visible light wavelength range, selected from the group of percentages consisting of equal to or less than 10%, equal to or less than 5%, equal to or less than 3%, equal to or less than 1%, equal to or less than 0.5% and equal to or less than 0.1%.

6. The system of claim 1, wherein the circadian active wavelength range includes wavelengths of green light selected from a group consisting of wavelength band ranges of: about 470 nm to about 560 nm, about 480 nm to about 550 nm, about 490 nm to about 555 nm, about 490 nm to about 560 nm, about 490 nm to about 565 nm, and about 490 nm to about 570 nm.

7. The system of claim 1, wherein the one or more light sources include a plurality of light sources, the plurality of light sources each provide illumination to the individual, and wherein the lighting command unit is configured to track characteristics of the aggregate incident lighting provided by the plurality of light sources to the individual:

wherein the lighting command encoding unit is configured to classify each light source of the plurality of light sources as being above an eye level of the individual or below the eye level of the individual, the eye level of the individual being a horizontal cross-section through a middle of the eye if the individual is upright or a vertical cross-section through the middle of the eye if the individual is in a supine or prone position; and wherein the lighting command unit is configured to only transmit the machine-level control commands to the one or more light sources that are classified as being above the eye level of the individual.

8. A method for operating one or more light sources providing illumination to an individual, the method comprising:

receiving electronic information indicative of a circadian state of an individual from one or more data sources;

assigning a circadian state to the individual based on the received electronic information, configured to extrapolate future circadian states based on the assigned circadian state, and configured to update a profile corresponding to the individual with the assigned circadian state and the extrapolated future circadian states, the assigned circadian state or the extrapolated future circadian states including at least a biological night state;

receiving the profile corresponding to the individual and encoding machine-level control commands that control the operation of the one or more light sources; and transmitting the machine-level control commands to the one or more light sources, the machine-level control commands adapted such that the aggregate incident lighting provided by the one or more light sources provides light with a spectral power distribution having circadian-significant attenuation along a circadian active wavelength range during durations of time when the individual is in the biological night state, and the aggregate incident lighting provided by the one or more light sources having overall lighting characteristics within a pre-determined comparable range relative to the aggregate incident lighting provided by the one or more light sources when the one or more light sources are activated but not controlled to have circadian-significant attenuation along the circadian active wavelength range;

wherein the circadian active wavelength range includes wavelengths of blue light and green light;

wherein the biological night state further includes (i) a biological early night state, and (ii) a biological late night state;

wherein for the biological early night state, the machine-level control commands are encoded such that the aggregate incident lighting provided by the one or more light sources provides light with a spectral power distribution having circadian-significant attenuation along both the blue and green wavelength ranges during durations of time when the individual is in the at least one biological early night state; and wherein for the biological late night state the machine-level control commands are encoded such that the aggregate incident lighting provided by the one or more light sources provides light with a spectral power distribution having circadian-significant attenuation along the blue wavelength range during durations of time when the individual is in the at least one biological late night state, while providing for substantial transmission along the green wavelength range.

9. The method of claim 8, wherein the circadian active wavelength range includes wavelengths of blue light.

10. The method of claim 9, wherein the circadian active wavelength range includes wavelengths of blue light provided between about 430 nm to about 490 nm.

11. The method of claim 9, wherein the circadian active wavelength range includes wavelengths of blue light selected from a group consisting of wavelength band ranges of: about 430 nm to about 500 nm, about 430 nm to about 490 nm, about 430 nm to about 480 nm, about 430 nm to about 470 nm, about 435 nm to about 500 nm, about 435 nm to about 490 nm, about 435 nm to about 480 nm, about 435 nm to about 470 nm, about 440 nm to about 500 nm, about 440 nm to about 490 nm, about 440 nm to about 480 nm, about 440 nm to about 470 nm, about 450 nm to about 500 nm, about 450 nm to about 490 nm, and about 460 nm to about 500 nm.

12. The method of claim 9, wherein the aggregate incident lighting provided in the circadian active wavelength range is attenuated to a percentage of an overall spectral power in a visible light wavelength range, selected from the group of percentages consisting of equal to or less than 10%, equal to or less than 5%, equal to or less than 3%, equal to or less than 1%, equal to or less than 0.5% and equal to or less than 0.1%.

13. The method of claim 8, wherein the circadian active wavelength range includes wavelengths of green light selected from a group consisting of wavelength band ranges of: about 470 nm to about 560 nm, about 480 nm to about 550 nm, about 490 nm to about 555 nm, about 490 nm to about 560 nm, about 490 nm to about 565 nm, and about 490 nm to about 570 nm.

14. The method of claim 8, wherein the one or more light sources include a plurality of light sources, the plurality of light sources each provide illumination to the individual, and further comprising tracking characteristics of the aggregate incident lighting provided by the plurality of light sources to the individual, wherein the method further comprises:

classifying each light source of the plurality of light sources as being above an eye level of the individual or below the eye level of the individual, the eye level of the individual being a horizontal cross-section through a middle of the eye if the individual is upright or a vertical cross-section through the middle of the eye if the individual is in a supine or prone position; and transmitting the machine-level control commands to the one or more light sources includes only transmitting the machine-level control commands to the one or more light sources that are classified as being above the eye level of the individual.

\* \* \* \* \*

UNITED STATES PATENT AND TRADEMARK OFFICE
CERTIFICATE OF CORRECTION

| | |
|---|---|
| PATENT NO. | : 10,471,231 B2 |
| APPLICATION NO. | : 15/556793 |
| DATED | : November 12, 2019 |
| INVENTOR(S) | : Martin Moore-Ede et al. |

It is certified that error appears in the above-identified patent and that said Letters Patent is hereby corrected as shown below:

In the Specification

In Column 1, at Line 15, insert the following subtitle and paragraph:
--STATEMENT OF GOVERNMENT SUPPORT
This invention was made with Government support under grant number HL110769 awarded by the National Institutes of Health. The Government has certain rights in the invention.--

Signed and Sealed this
Twentieth Day of December, 2022

Katherine Kelly Vidal
*Director of the United States Patent and Trademark Office*